United States Patent
Wang

(10) Patent No.: US 11,353,533 B2
(45) Date of Patent: Jun. 7, 2022

(54) METHODS AND DEVICES FOR CONTRAST AGENT MAGNETIC RESONANCE IMAGING

(71) Applicant: OHIO STATE INNOVATION FOUNDATION, Columbus, OH (US)

(72) Inventor: Jinghua Wang, Mason, OH (US)

(73) Assignee: Ohio State Innovation Foundation, Columbus, OH (US)

(*) Notice: Subject to any disclaimer, the term of this patent is extended or adjusted under 35 U.S.C. 154(b) by 693 days.

(21) Appl. No.: 16/079,681

(22) PCT Filed: Feb. 24, 2017

(86) PCT No.: PCT/US2017/019347
§ 371 (c)(1),
(2) Date: Aug. 24, 2018

(87) PCT Pub. No.: WO2017/147418
PCT Pub. Date: Aug. 31, 2017

(65) Prior Publication Data
US 2019/0056470 A1 Feb. 21, 2019

Related U.S. Application Data

(60) Provisional application No. 62/299,077, filed on Feb. 24, 2016.

(51) Int. Cl.
*G01R 33/56* (2006.01)
*A61B 5/00* (2006.01)
(Continued)

(52) U.S. Cl.
CPC ........ *G01R 33/5601* (2013.01); *A61B 5/0037* (2013.01); *A61B 5/055* (2013.01); *G01R 33/5608* (2013.01); *A61B 8/481* (2013.01)

(58) Field of Classification Search
CPC .... A61B 5/037; A61B 5/055; G01R 33/5601; G01R 33/5608
See application file for complete search history.

(56) References Cited

U.S. PATENT DOCUMENTS 5,031,620 A * 7/1991 Oe .................... H05G 1/60
600/425
6,505,064 B1 1/2003 Liu et al.
(Continued)

FOREIGN PATENT DOCUMENTS

EP 1784227 10/2011
WO 2003/007010 1/2003
(Continued)

OTHER PUBLICATIONS

Wang, Jinghua, Lili He, Hairong Zheng, and Zhong-Lin Lu. "Optimizing the magnetization-prepared rapid gradient-echo (MP-RAGE) sequence." PloS one 9, No. 5 (2014): e96899.*
(Continued)

*Primary Examiner* — Carolyn A Pehlke
(74) *Attorney, Agent, or Firm* — Meunier Carlin & Curfman LLC

(57) ABSTRACT

A method for detecting lesion tissue using contrast agent MRI includes receiving scanner settings; receiving MR parameters for lesion tissue with or without contrast agent; and simulating relationships between an image quality metric and imaging parameters. The method includes selecting a first set of imaging parameters to optimize an image quality metric of a first image acquired before contrast agent administration; selecting a second set of imaging parameters to optimize a lesion enhancement metric of a second image acquired after contrast agent administration; and selecting an image acquisition time for the second image to maximize the lesion enhancement metric. The method includes acquiring the first and second images using the selected first and
(Continued)

second sets of imaging parameters, respectively; and generating a combined image from the first and second images.

20 Claims, 18 Drawing Sheets

(51) Int. Cl.
*A61B 5/055* (2006.01)
*A61B 8/08* (2006.01)

(56) References Cited

U.S. PATENT DOCUMENTS

| | | | |
|---|---|---|---|
| 7,567,832 | B2 | 7/2009 | Schmainda et al. |
| 7,738,683 | B2 | 6/2010 | Cahill |
| 8,090,429 | B2 | 1/2012 | Vija et al. |
| 8,175,678 | B2 | 5/2012 | Dahnke et al. |
| 8,337,813 | B2 | 12/2012 | Schultz et al. |
| 8,428,323 | B2 | 4/2013 | Kim et la. |
| 8,463,358 | B2 | 6/2013 | Lamerichs et al. |
| 8,472,684 | B1 | 6/2013 | Periaswamy |
| 8,475,768 | B2 | 7/2013 | Axelsson et al. |
| 8,540,966 | B2 | 9/2013 | Aime et al. |
| 8,568,690 | B2 | 10/2013 | Lu et al. |
| 8,655,041 | B2 | 2/2014 | John et al. |
| 8,784,778 | B2 | 7/2014 | Aime et al. |
| 8,818,057 | B2 | 8/2014 | Bond et al. |
| 9,002,430 | B2 | 4/2015 | Riederer et al. |
| 9,053,213 | B2 | 6/2015 | Wenzel et al. |
| 9,056,138 | B2 | 6/2015 | Fan et al. |
| 9,521,985 | B2 | 12/2016 | Liao et al. |
| 2003/0028101 | A1 | 2/2003 | Caravan et al. |
| 2003/0125617 | A1 | 7/2003 | Bjornerud et al. |
| 2004/0242994 | A1 | 12/2004 | Brady et al. |
| 2007/0073141 | A1 | 3/2007 | Iwadate et al. |
| 2008/0091100 | A1* | 4/2008 | Assmann .............. G06T 7/0012 |
| | | | 600/410 |
| 2008/0193384 | A1 | 8/2008 | Willard |
| 2008/0200799 | A1 | 8/2008 | Willard et al. |
| 2008/0305049 | A1 | 12/2008 | Degani et al. |
| 2009/0080741 | A1* | 3/2009 | Shinagawa .......... G06K 9/4609 |
| | | | 382/131 |
| 2009/0191131 | A1 | 7/2009 | Fossheim et al. |
| 2009/0196830 | A1 | 8/2009 | Lamerichs et al. |
| 2009/0238768 | A1 | 9/2009 | Axelsson et al. |
| 2009/0245606 | A1* | 10/2009 | Prince ..................... G06T 5/50 |
| | | | 382/130 |
| 2010/0056787 | A1 | 3/2010 | Wadsworth et al. |
| 2010/0198054 | A1 | 8/2010 | Ewing et al. |
| 2010/0215581 | A1 | 8/2010 | Hoffmann |
| 2011/0133735 | A1 | 6/2011 | Yokosawa et al. |
| 2011/0200536 | A1 | 8/2011 | Wadsworth et al. |
| 2012/0099768 | A1 | 4/2012 | Helm et al. |
| 2013/0096420 | A1 | 4/2013 | Aime et al. |
| 2013/0211230 | A1 | 8/2013 | Sperling |
| 2013/0274589 | A1 | 10/2013 | Gross et al. |
| 2013/0279785 | A1 | 10/2013 | Gross et al. |
| 2013/0310678 | A1 | 11/2013 | Balbi et al. |
| 2014/0064589 | A1 | 3/2014 | Dale |
| 2014/0107469 | A1 | 4/2014 | Gjesdal et al. |
| 2014/0169658 | A1 | 6/2014 | Kowalevicz et al. |
| 2014/0205204 | A1 | 7/2014 | Jiang et al. |
| 2014/0205545 | A1 | 7/2014 | Fan et al. |
| 2014/0354642 | A1 | 12/2014 | Wiemker et al. |
| 2015/0017102 | A1 | 1/2015 | Frank et al. |
| 2015/0036948 | A1 | 2/2015 | Wenzel et al. |
| 2015/0037261 | A1 | 2/2015 | Beltrami et al. |
| 2015/0042329 | A1 | 2/2015 | Zhang et al. |
| 2015/0071514 | A1 | 3/2015 | Wang et al. |
| 2015/0247909 | A1 | 9/2015 | Wawro et al. |
| 2018/0045799 | A1 | 2/2018 | Wang et al. |

FOREIGN PATENT DOCUMENTS

| | | |
|---|---|---|
| WO | 2006/114738 | 11/2006 |
| WO | 2006/114765 | 11/2006 |
| WO | 2008/138822 | 11/2008 |
| WO | 2010/125088 | 11/2010 |
| WO | 2014/107722 | 7/2014 |

OTHER PUBLICATIONS

Gharagouzloo, Codi Amir, Patrick N. McMahon, and Srinivas Sridhar. "Quantitative contrast-enhanced MRI with superparamagnetic nanoparticles using ultrashort time-to-echo pulse sequences." Magnetic resonance in medicine 74, No. 2 (2015): 431-441.*
Stevenson, Jeffrey, Edmond A. Knopp, and Andrew W. Litt. "MP-RAGE subtraction venography: A new technique." Journal of Magnetic Resonance Imaging 5, No. 2 (1995): 239-241.*
International Preliminary Report on Patentability issued for Application No. PCT/US17/19347, dated Sep. 7, 2018.
Abernethy L, Avula S, Hughes G, Wright E, Mallucci C. Intra-operative 3-T MRI for paediatric brain tumours: challenges and perspectives. Pediatric radiology. 2012;42(2):147-57.
Adin ME et al. Hyperintense dentate nuclei on T1-weighted MRI: relation to repeat gadolinium administration. AJNR Am J Neuroradiol. 2015; 36: 1859-1865.
Aime, S., et al., Pushing the sensitivity envelope of lanthanide-based magnetic resonance imaging (MRI) contrast agents for molecular imaging applications. Acc Chem Res, 2009. 42(7): p. 822-31.
Alsop DC. The sensitivity of low flip angle RARE imaging. Magnetic resonance in medicine. 1997;37(2):176-84.
Anzalone, N., et al., Optimizing contrast-enhanced magnetic resonance imaging characterization of brain metastases: relevance to stereotactic radiosurgery. Neurosurgery, 2013. 72(5): p. 691-701.
Aronen, H.J., et al., The effect of paramagnetic contrast media on T1 relaxation times in brain tumors. Acta Radiol, 1998. 39(5): p. 474-81.
Artzi M, Liberman G, Nadav G, Blumenthal DT, Bokstein F, Aizenstein O, et al. Optimization of DCE-MRI protocol for the assessment of patients with brain tumors. Magnetic resonance imaging. 2016;34(9):1242-7.
Atri M. New technologies and directed agents for applications of cancer imaging. Journal of Clinical Oncology. 2006;24(20):3299-308.
Beiderwellen K, Kraff O, Laader A, Maderwald S, Orzada S, Ladd ME, et al. Contrast enhanced renal MR angiography at 7 Tesla: How much gadolinium do we need? Eur J Radiol. 2017;86:76-82.
Bellin, M.-F. and A.J. Van Der Molen, Extracellular gadolinium-based contrast media: An overview. Eur J Radiol, 2008. 66(2): p. 160-167.
Bellin, M.-F., MR contrast agents, the old and the new. Eur J Radiol, 2006. 60(3): p. 314-323.
Bhargava R, Hahn G, Hirsch W, Kim M-J, Mentzel H-J, Olsen ØE, et al. Contrast-Enhanced Magnetic Resonance Imaging in Pediatric Patients: Review and Recommendations for Current Practice. Magnetic resonance insights. 2013;6:95.
Biswas J, Nelson CB, Runge VM, Wintersperger BJ, Baumann SS, Jackson CB, et al. Brain tumor enhancement in magnetic resonance imaging: comparison of signal-to-noise ratio (SNR) and contrast-to-noise ratio (CNR) at 1.5 versus 3 tesla. Invest Radiol. 2005;40(12):792-7.
Bogdanov A, Jr., Mazzanti ML. Molecular magnetic resonance contrast agents for the detection of cancer: past and present. Semin Oncol. 2011;38(1):42-54.
Bolbos, R.I., et al., Relationship between trabecular bone structure and articular cartilage morphology and relaxation times in early OA of the knee joint using parallel MRI at 3.0 T. Osteoarthritis and Cartilage, 2008. 16(10): p. 1150-1159.
Busse RF. Reduced RF power without blurring: correcting for modulation of refocusing flip angle in FSE sequences. Magnetic resonance in medicine. 2004;51(5):1031-7.

(56) References Cited

OTHER PUBLICATIONS

Caravan, P., Strategies for increasing the sensitivity of gadolinium based MRI contrast agents. Chemical Society Reviews, 2006. 35(6): p. 512-523.
Castillo, M., History and evolution of brain tumor imaging: insights through radiology. Radiology, 2014. 273(2 Suppl): p. S111-25.
Chappell PM, Pelc NJ, Foo TK, Glover GH, Haros SP, Enzmann DR. Comparison of lesion enhancement on spin-echo and gradient-echo images. AJNR American journal of neuroradiology. 1994;15(1):37-44.
Cheong BYC, Duran C, Preventza OA, Muthupillai R. Comparison of Low-Dose Higher-Relaxivity and Standard-Dose Lower-Relaxivity Contrast Media for Delayed-Enhancement MRI: A Blinded Randomized Crossover Study. American Journal of Roentgenology. 2015;205(3):533-9.
Colosimo C et al. Comparison of gadobenate dimeglumine (Gd-BOPTA) with gadopentetate dimeglumine (Gd-DTPA) for enhanced MR imaging of brain and spine tumours in children. Pediatr Radiol. 2005;35(5):501-10.
Colosimo C, Ruscalleda J, Korves M, La Ferla R, Wool C, Pianezzola P, et al. Detection of intracranial metastases: a multicenter, intrapatient comparison of gadobenate dimeglumine-enhanced MRI with routinely used contrast agents at equal dosage. Investigative radiology. 2001;36(2):72-81.
Colosimo, C., et al., Contrast-enhanced MR imaging of the spine: when, why and how? How to optimize contrast protocols in MR imaging of the spine. Neuroradiology, 2006. 48 Suppl 1: p. 18-33.
De Stasio G, Casalbore P, Pallini R, Gilbert B, Sanita F, Ciotti MT, et al. Gadolinium in human glioblastoma cells for gadolinium neutron capture therapy. Cancer research. 2001;61(10):4272-7.
Derakhshan, J.J. and J.L. Duerk, Update to pulse sequences for interventional MR imaging. Magn Reson Imaging Clin N Am, 2005. 13(3): p. 415-29.
Elster A. How much contrast is enough? Eur Radiol. 1997;7(5) S276-280.
Errante Y, Cirimele V, Mallio CA, et al. Progressive increase of T1 signal intensity of the dentate nucleus on unenhanced magnetic resonance images is associated with cumulative doses of intravenously administered gadodiamide in patients with normal renal function, suggesting dechelation. Invest Radiol. 2014; 49: 685-690.
Essig M, Anzalone N, Combs S, Dörfler À, Lee S-K, Picozzi P, et al. MR imaging of neoplastic central nervous system lesions: review and recommendations for current practice. American journal of neuroradiology. 2012;33(5):803-17.
Essig M, Weber M-A, von Tengg-Kobligk H, Knopp MV, Yuh WT, Giesel FL. Contrast-enhanced magnetic resonance imaging of central nervous system tumors agents, mechanisms, and applications. Topics in Magnetic Resonance Imaging. 2006;17(2):89-106.
Essig, M., J. Dinkel, and J.E. Gutierrez, Use of contrast media in neuroimaging. Magn Reson Imaging Clin N Am, 2012. 20(4): p. 633-48.
Essig, M., MR imaging of CNS tumors: are all contrast agents created the same? Neuroradiology, 2006. 48 Suppl 1: p. 3-8.
Essig, M., Protocol design for high relaxivity contrast agents in MR imaging of the CNS. Eur Radiol, 2006. 16 Suppl 7: p. M3-7.
Fakhran S et al. Assessment of rates of acute adverse reactions to gadobenate dimeglumine: review of more than 130,000 administrations in 7.5 years. AJR Am J Roentgenol. 2015;204:703-706.
Ferré J-C, Shiroishi MS, Law M. Advanced Techniques Using Contrast Media in Neuroimaging. Magn Reson Imaging Clin N Am. 2012;20(4):699-713.
Flood TF, Stence NV, Maloney JA, Mirsky DM. Pediatric Brain: Repeated Exposure to Linear Gadolinium-based Contrast Material Is Associated with Increased Signal Intensity at Unenhanced T1-weighted MR Imaging. Radiology. 2017;282(1):222-8.
Giesel, F.L., A. Mehndiratta, and M. Essig, High-relaxivity contrast-enhanced magnetic resonance neuroimaging: a review. Eur Radiol, 2010. 20(10): p. 2461-74.

Grobner T. Gadolinium—a specific trigger for the development of nephrogenic fibrosing dermopathy and nephrogenic systemic fibrosis? Nephrol Dial Transplant 2006;21:1104-1108.
Grosu A-L, Oehlke O, Nieder C. Brain Tumors. Target Volume Definition in Radiation Oncology: Springer; 2015. p. 1-21.
Gruber S et al. Dynamic contrast-enhanced magnetic resonance imaging of breast tumors at 3 and 7 T: a comparison. Invest Radiol. 2014;49(5):354-62.
Guglielmo FF, Mitchell DG, Roth CG, Deshmukh S. Hepatic MR Imaging Techniques, Optimization, and Artifacts. Magn Reson Imaging Clin N Am. 2014;22(3):263-82.
Guglielmo, F.F., D.G. Mitchell, and S. Gupta, Gadolinium contrast agent selection and optimal use for body MR imaging. Radiol Clin North Am, 2014. 52(4): p. 637-56.
Gutierrez JE, Rosenberg M, Seemann J, Breuer J, Haverstock D, Agris J, et al. Safety and Efficacy of Gadobutrol for Contrast-enhanced Magnetic Resonance Imaging of the Central Nervous System: Results from a Multicenter, Double-blind, Randomized, Comparator Study. Magnetic resonance insights. 2015;8:1.
Gutierrez, J.E., S. Koenig, and J. Breuer, Overview on the efficacy and safety of gadobutrol: an MRI contrast agent for the CNS, body and vessels. Imaging in Medicine, 2012. 4(1): p. 25-40.
Hamilton, B.E., et al., Comparative analysis of ferumoxytol and gadoteridol enhancement using T1- and T2-weighted MRI in neuroimaging. AJR Am J Roentgenol, 2011. 197(4): p. 981-8.
Hao, D., et al., MRI contrast agents: basic chemistry and safety. J Magn Reson Imaging, 2012. 36(5): p. 1060-71.
He L, Wang J, Lu ZL, and Parikh NA. Optimization of magnetization-prepared rapid gradient echo (MP-RAGE) sequence for neonatal brain MRI. Aug. 2018;48(8): 1139-1151.
Hendrick RE. High-quality breast MRI. Radiol Clin North Am. 2014;52(3):547-62.
Hennig J, Weigel M, Scheffler K. Calculation of flip angles for echo trains with predefined amplitudes with the extended phase graph (EPG)-algorithm: principles and applications to hyperecho and TRAPS sequences. Magnetic resonance in medicine. 2004;51(1):68-80.
Hennig J. Echoes—how to generate, recognize, use or avoid them in MR-imaging sequences. Part II: Echoes in imaging sequences. Concepts in Magnetic Resonance. 1991;3(4):179-92.
James AP, Dasarathy BV. Medical image fusion: A survey of the state of the art. Information Fusion. 2014;19:4-19.
Jeon J-Y, Choi JW, Roh HG, Moon W-J. Effect of Imaging Time in the Magnetic Resonance Detection of Intracerebral Metastases Using Single Dose Gadobutrol. Korean Journal of Radiology. 2014;15(1):145-50.
Kammer N et al. Comparison of contrast-enhanced modified T1-weighted 3D TSE black-blood and 3D MP-RAGE sequences for the detection of cerebral metastases and brain tumours. European radiology. 2016, 1818-1825.
Kanal, E., Gadolinium-Based Magnetic Resonance Contrast Agents for Neuroradiology: An Overview. Magn Reson Imaging Clin N Am, 2012. 20(4): p. 625-631.
Kanda T et al. Gadolinium-based Contrast Agent Accumulates in the Brain Even in Subjects without Severe Renal Dysfunction: Evaluation of Autopsy Brain Specimens with Inductively Coupled Plasma Mass Spectroscopy. Radiology. (2015) vol. 276, Issue: 1, pp. 228-232.
Kanda T et al. High signal intensity in dentate nucleus on unenhanced T1-weighted MR images: association with linear versus macrocyclic gadolinium chelate administration. Radiology. 2015; 275: 803-809.
Kanda T, Ishii K, Kawaguchi H, et al. High signal intensity in the dentate nucleus and globus pallidus on unenhanced T1-weighted MR images: relationship with increasing cumulative dose of a gadolinium-based contrast material. Radiology. 2014; 270: 834-841.
Kanda T, Matsuda M, Oba H, Toyoda K, Furui S. Gadolinium Deposition after Contrast-enhanced MR Imaging. Radiology. 2015;277(3):924-5.
Khant ZA, Hirai T, Kadota Y, Masuda R, Yano T, Azuma M, et al. T1 Shortening in the Cerebral Cortex after Multiple Administrations of Gadolinium-based Contrast Agents. Magnetic resonance in medical sciences, Magn Reson Med Sci. 2017;16(1): 84-86.

(56) References Cited

OTHER PUBLICATIONS

Kim, B.-s. and J.E. Gutierrez, Contrast-Enhanced MR Imaging in Neuroimaging. Magn Reson Imaging Clin N Am, 2012, 20(4): p. 649-685.

Knauth M, Aras N, Wirtz CR, Dörfler A, Engelhorn T, Sartor K. Surgically induced intracranial contrast enhancement: potential source of diagnostic error in intraoperative MR imaging. American journal of neuroradiology. 1999;20(8):1547-53.

Krautmacher C et al. Brain tumors: full- and half-dose contrast-enhanced MR imaging at 3.0 T compared with 1.5 T—Initial Experience. Radiology. 2005;237(3):1014-9.

Kushnirsky M, Nguyen V, Katz JS, Steinklein J, Rosen L, Warshall C, et al. Time-delayed contrast-enhanced MRI improves detection of brain metastases and apparent treatment volumes. Journal of neurosurgery. 2016;124(2):489-95.

Landis CS, Li X, Telang FW, Coderre JA, Micca PL, Rooney WD, et al. Determination of the MRI contrast agent concentration time course in vivo following bolus injection: effect of equilibrium transcytolemmal water exchange. Magnetic resonance in medicine. 2000;44(4):563-74.

Lavdas, E., et al., Evaluation of fat saturation and contrast enhancement on T1-weighted FLAIR sequence of the spine at 3.0 T. Clin Imaging, 2014. 38(4): p. 428-33.

Ledger, A.E., et al., Investigating the influence of flip angle and k-space sampling on dynamic contrastenhanced MRI breast examinations. Acad Radiol, 2014. 21(11): p. 1394-401.

Lescher S, Schniewindt S, Jurcoane A, Senft C, Hattingen E. Time window for postoperative reactive enhancement after resection of brain tumors: less than 72 hours. Neurosurgical focus. 2014;37(6):E3.

Li D, Haacke EM, Tarr RW, Venkatesan R, Lin W, Wielopolski P. Magnetic resonance imaging of the brain with gadopentetate dimeglumine-DTPA: comparison of T1-weighted spin-echo and 3D gradient-echo sequences. J Magn Reson Imaging. 1996;6(3):415-24.

Li, X., et al., In vivo T1ρ and T2 mapping of articular cartilage in osteoarthritis of the knee using 3 T MRI. Osteoarthritis and Cartilage, 2007. 15(7): p. 789-797.

Lim H, Lee J, Hyun D, Park J, Kim J, Lee H, et al. MR diagnosis of facial neuritis diagnostic performance of contrast-enhanced 3D-FLAIR technique compared with contrast-enhanced 3D-T1-fast-field echo with fat suppression. American journal of neuroradiology. 2012;33(4):779-83.

Lin SP, Brown JJ. MR contrast agents: physical and pharmacologic basics. Journal of Magnetic Resonance Imaging. 2007;25(5):884-99.

Lohrke J, Frenzel T, Endrikat J, Alves FC, Grist TM, Law M, et al. 25 Years of Contrast-Enhanced MRI: Developments, Current Challenges and Future Perspectives. Advances in therapy. 2016;33(1):1-28.

Louie A. Magnetic resonance imaging contrast agents in the study of development. Current topics in developmental biology. 2005;70:35-56.

Lukzen N et al. The generating functions formalism for the analysis of spin response to the periodic trains of RF pulses. Echo sequences with arbitrary refocusing angles and resonance offsets. Journal of Magnetic Resonance. 2009;196(2):164-9.

Majigsuren M, Abe T, Kageji T, Matsuzaki K, Takeuchi M, Iwamoto S, et al. Comparison of Brain Tumor Contrast-enhancement on T-CUBE and 3D-SPGR Images. Magnetic resonance in medical sciences : MRMS : an official journal of Japan Society of Magnetic Resonance in Medicine. 2015, 34-40.

Maki JH et al. Patient-specific timing for bolus-chase peripheral MR angiography. Journal of Magnetic Resonance Imaging. 2016;43(1):249-60.

Malayeri AA, Brooks KM, Bryant LH, Evers R, Kumar P, Reich DS, et al. National Institutes of Health Perspective on Reports of Gadolinium Deposition in the Brain. Journal of the American College of Radiology. 2016;13(3):237-41.

Martin DR. Nephrogenic system fibrosis: a radiologist's practical perspective. Eur J Radiol. 2008;66(2):220-4.

Masi, J.N., et al., Optimization of gadodiamide concentration for MR arthrography at 3 T. American Journal of Roentgenology, 2005. 184(6): p. 1754-1761.

McDonald RJ, McDonald JS, Kallmes DF, et al. Intracranial gadolinium deposition after contrast-enhanced MR imaging. Radiology. 2015; 275: 772-782.

Mitsumori, L.M., et al., Magnetic resonance imaging using gadolinium-based contrast agents. Top Magn Reson Imaging, 2014. 23(1): p. 51-69.

Mugler, J.P., 3rd and J.R. Brookeman, Theoretical analysis of gadopentetate dimeglumine enhancement in T1-weighted imaging of the brain: comparison of two-dimensional spin-echo and three-dimensional gradient-echo sequences. J Magn Reson Imaging, 1993. 3(5): p. 761-9.

Natalin RA, Prince MR, Grossman ME, Silvers D, Landman J. Contemporary applications and limitations of magnetic resonance imaging contrast materials. J Urol. 2010;183(1):27-33.

Nissi, M.J., et al., Estimation of mechanical properties of articular cartilage with MRI—dGEMRIC, T2 and T1 imaging in different species with variable stages of maturation. Osteoarthritis Cartilage, 2007. 15(10): p. 1141-8.

Nobauer-Huhmann, I.M., et al., Magnetic resonance imaging contrast enhancement of brain tumors at 3 tesla versus 1.5 tesla. Invest Radiol, 2002. 37(3): p. 114-9.

Noebauer-Huhmann, I.M., et al., Brain tumours at 7T MRI compared to 3T-contrast effect after half and full standard contrast agent dose: initial results. Eur Radiol, 2015. 25(1): p. 106-12.

Obermeier B, Daneman R, Ransohoff RM. Development, maintenance and disruption of the blood-brain barrier. Nature medicine. 2013;19(12):1584-96.

Oliveira FP, Tavares JMR. Medical image registration: a review. Computer methods in biomechanics and biomedical engineering. 2014;17(2):73-93.

Padhani AR, Husband JE. Dynamic contrast-enhanced MRI studies in oncology with an emphasis on quantification, validation and human studies. Clinical radiology. 2001;56(8):607-20.

Pedersen M. Safety update on the possible causal relationship between gadolinium-containing MRI agents and nephrogenic systemic fibrosis. J Magn Reson Imaging. 2007;25(5):881-3.

Pham DL, Xu C, Prince JL. Current methods in medical image segmentation 1. Annual review of biomedical engineering. 2000;2(1):315-37.

Prastawa M, Bullitt E, Gerig G. Simulation of brain tumors in MR images for evaluation of segmentation efficacy. Medical image analysis. 2009;13(2):297-311.

Quattrocchi CC et al. Gadodiamide and dentate nucleus T1 hyperintensity in patients with meningioma evaluated by multiple follow-up contrast-enhanced magnetic resonance examinations with no systemic interval therapy. Invest Radiol. 2015; 50: 470-472.

Radbruch A et al. Gadolinium retention in the dentate nucleus and globus pallidus is dependent on the class of contrast agent. Radiology. 2015; 275: 783-791.

Ramalho J et al. High signal intensity in globus pallidus and dentate nucleus on unenhanced T1-weighted MR images: evaluation of two linear gadolinium-based contrast agents. Radiology Jun. 16, 2015:150872.

Reeder SB, Smith MR, Hernando D. Mathematical optimization of contrast concentration for T1-weighted spoiled gradient echo imaging. Magn Reson Med. 2016;75(4):1556-64.

Rinck, P.A. and R.N. Muller, Field strength and dose dependence of contrast enhancement by gadolinium-based MR contrast agents. Eur Radiol, 1999. 9(5): p. 998-1004.

Robert P et al. T1-weighted hypersignal in the deep cerebellar nuclei after repeated administrations of gadolinium-based contrast agents in healthy rats: difference between linear and macrocyclic agents. Invest Radiol Jun. 22, 2015, 50(8): 473-480.

Roberts, T.P., N. Chuang, and H.C. Roberts, Neuroimaging: do we really need new contrast agents for MRI? Eur J Radiol, 2000. 34(3): p. 166-78.

Rohrer, M., et al., Comparison of magnetic properties of MRI contrast media solutions at different magnetic field strengths. Invest Radiol, 2005. 40(11): p. 715-24.

(56) References Cited

OTHER PUBLICATIONS

Runge VM, Bronen RA, Davis KR. Efficacy of gadoteridol for magnetic resonance imaging of the brain and spine. Invest Radiol. 1992;27 Suppl 1:S22-32.
Runge VM. Current technological advances in magnetic resonance with critical impact for clinical diagnosis and therapy. Investigative radiology. 2013;48(12):869-77.
Runge, V.M., Gd-DTPA: an i.v. contrast agent for clinical MRI. Int J Rad Appl Instrum B, 1988. 15(1): p. 37-44.
Sardanelli F, Schiavoni S, Iozzelli A, Fausto A, Aliprandi A, Mancardi GL, et al. The value of chemical fat-saturation pulse added to T1-weighted spin-echo sequence in evaluating gadolinium-enhancing brain lesions in multiple sclerosis. Radiol Med. 2007;112(8):1244-51.
Schörner W, Laniado M, Niendorf H, Schubert C, Felix R. Time-dependent changes in image contrast in brain tumors after gadolinium-DTPA. American journal of neuroradiology. 1986;7(6):1013-20.
Shah KB, Guha-Thakurta N, Schellingerhout D, Madewell JE, Kumar AJ, Costelloe CM. Comparison of gadolinium-enhanced fat-saturated T1-weighted FLAIR and fast spin-echo MRI of the spine at 3 T for evaluation of extradural lesions. AJR Am J Roentgenol. 2011;197(3):697-703.
Shellock FG, Spinazzi A. MRI safety update 2008: part 1, MRI contrast agents and nephrogenic systemic fibrosis. AJR Am J Roentgenol. 2008;191(4):1129-39.
Shokrollahi, H., Contrast agents for MRI. Mater Sci Eng C Mater Biol Appl, 2013. 33(8): p. 4485-97.
Sourbron SP, Buckley DL. Classic models for dynamic contrast-enhanced MRI. NMR Biomed. 2013;26(8):1004-27.
Steen, R.G., et al., Effect of a gadodiamide contrast agent on the reliability of brain tissue T1 measurements. Magn Reson Imaging, 1999. 17(2): p. 229-35.
Strijkers, G.J., et al., MRI contrast agents: current status and future perspectives. Anticancer Agents Med Chem, 2007. 7(3): p. 291-305.
Su MY, Mühler A, Lao X, Nalcioglu O. Tumor characterization with dynamic contrast-enhanced MRI using mr contrast agents of various molecular weights. Magnetic resonance in medicine. 1998;39(2):259-69.
Sussman, M.S., et al., Optimizing contrast agent concentration and spoiled gradient echo pulse sequence parameters for catheter visualization in MR-guided interventional procedures: an analytic solution. Magn Reson Med, 2013. 70(2): p. 333-40.
Taylor, C., et al., Comparison of quantitative imaging of cartilage for osteoarthritis: T2, T1rho, dGEMRIC and contrast-enhanced computed tomography. Magn Reson Imaging, 2009. 27(6): p. 779-84.
Thomsen HS. Contrast media safety—an update. Eur J Radiol. 2011;80(1):77-82.
Trattnig, S., et al., MR contrast agent at high-field MRI (3 Tesla). Top Magn Reson Imaging, 2003. 14(5): p. 365-75.
Trattnig, S., et al., T1(Gd) gives comparable information as Delta T1 relaxation rate in dGEMRIC evaluation of cartilage repair tissue. Invest Radiol, 2009. 44(9): p. 598-602.
Trattnig, S., et al., The optimal use of contrast agents at high field MRI. Eur Radiol, 2006. 16(6): p. 1280-7.
Van der Molen AJ, Bellin M-F. Extracellular gadolinium-based contrast media: Differences in diagnostic efficacy. European journal of radiology. 2008;66(2):168-74.
Vargas HA, Wassberg C, Akin O, Hricak H. MR imaging of treated prostate cancer. Radiology. 2012;262(1):26-42.
Villringer K, Sanz Cuesta BE, Ostwaldt AC, Grittner U, Brunecker P, Khalil AA, et al. DCE-MRI blood-brain barrier assessment in acute ischemic stroke. Neurology. 2016.
Von Tengg-Kobligk, H., A. Mehndiratta, and F.L. Giesel, Contrast agents in radiology, in Medical Imaging in Clinical Trials 2014, Springer, p. 327-357.
Wang J, He L, Lu ZL. Optimization of Magnetization-prepared Rapid Gradient-echo (MP-RAGE) Sequence at 3.0 T. PLOS ONE. 2014;9: e96899.
Warmuth-Metz M, Bison B, Leykamm S. Neuroradiologic review in pediatric brain tumor studies. Clinical Neuroradiology. 2009;19(4):263-73.
Warntjes, J.B., et al., Effects of gadolinium contrast agent administration on automatic brain tissue classification of patients with multiple sclerosis. AJNR Am J Neuroradiol, 2014. 35(7): p. 1330-6.
Watanabe, A., et al., Effect of multislice acquisition on T1 and T2 measurements of articular cartilage at 3T. J Magn Reson Imaging, 2007. 26(1): p. 109-17.
Weigel M, Helms G, Hennig J. Investigation and modeling of magnetization transfer effects in two-dimensional multislice turbo spin echo sequences with low constant or variable flip angles at 3 T. Magnetic resonance in medicine. 2010;63(1):230-4.
Weinmann H-J et al. Tissue-specific MR contrast agents. European journal of radiology. 2003;46(1):33-44.
Weinmann, H.-J., et al., Characteristics of gadolinium-DTPA complex: a potential NMR contrast agent. American Journal of Roentgenology, 1984. 142(3): p. 619-624.
Weng JC, Wu SK, Yang FY, Lin WL, Tseng WYI. Pulse sequence and timing of contrast-enhanced MRI for assessing blood-brain barrier disruption after transcranial focused ultrasound in the presence of hemorrhage. Journal of Magnetic Resonance Imaging. 2010;31(6):1323-30.
Wesolowski JR, Kaiser A. Alternatives to GBCA: Are We There Yet? Topics in magnetic resonance imaging : TMRI. 2016;25(4):171-5.
Yamada, K., et al., Effect of intravenous gadolinium-DTPA on diffusion-weighted images: evaluation of normal brain and infarcts. Stroke, 2002. 33(7): p. 1799-802.
Yi Ca, Shin KM, Lee KS, Kim B-T, Kim H, Kwon OJ, et al. Non-Small Cell Lung Cancer Staging: Efficacy Comparison of Integrated PET/CT versus 3.0-T Whole-Body MR Imaging 1. Radiology. 2008;248(2):632-42.
Yuh W, Tali ET, Nguyen HD, Simonson TM, Mayr NA, Fisher DJ. The effect of contrast dose, imaging time, and lesion size in the MR detection of intracerebral metastasis. American journal of neuroradiology. 1995;16(2):373-80.
Zakaria R, Das K, Bhojak M, Radon M, Walker C, Jenkinson MD. The role of magnetic resonance imaging in the management of brain metastases: diagnosis to prognosis. Cancer Imaging. 2014;14(1):8.

\* cited by examiner

Figure 11A Optimal Pre-contrast
Figure 11B Optimal Post-contrast (Fused Image)

METHODS AND DEVICES FOR CONTRAST AGENT MAGNETIC RESONANCE IMAGING

CROSS-REFERENCE TO RELATED APPLICATIONS

This application is a national stage application filed under 35 U.S.C. § 371 of PCT/US2017/019347 filed Feb. 24, 2017, which claims the benefit of U.S. Provisional Patent Application No. 62/299,077, filed on Feb. 24, 2016, entitled "METHODS AND DEVICES FOR CONTRAST AGENT MAGNETIC RESONANCE IMAGING," the disclosures of which are expressly incorporated herein by reference in their entireties.

BACKGROUND

Magnetic Resonance Imaging ("MRI") is one of the most important modern medical imaging modalities. It has far less risk of side effects than most other imaging modalities such as radioscopy with x-rays or computed tomography because patient and medical personnel are not subjected to ionizing radiation exposure in the procedure. The use of MRI has grown very fast. Every year, more than 30 million MRI scans are performed in the United States; more than 60 million MRI scans are performed worldwide. Doctors often recommend MRI for the diagnoses of various diseases, such as tumors, strokes, heart problems, and spine disease. A high-quality scan is important for maximizing diagnostic sensitivity and making the right diagnosis. Generally, a high quality image requires high signal-to-noise ratio ("SNR"), high contrast between normal and pathological tissues, low levels of artifact, and reasonable and acceptable spatial-temporal resolution.

In order to obtain a detectable MR signal, the object examined is positioned in a homogeneous static magnetic field so that the object's nuclear spins generate net magnetization oriented along the static magnetic field. The net magnetization is rotated away from the static magnetic field using a radio frequency ("RF") excitation field with the same frequency as the Larmor frequency of the nucleus. The rotated angle is determined by the field strength of the RF excitation pulse and its duration. In the end of the RF excitation pulse, the nuclei, in relaxing to their normal spin conditions, generate a decaying signal (the "MR signal") at the same radio frequency as that used for excitation. The MR signal is picked up by a receive coil, amplified and processed. The acquired measurements are digitized and stored as complex numerical values in a "k-space" matrix. An associated MR image can be reconstructed from the k-space data, for example, by an inverse 2D or 3D fast Fourier transform ("FFT") from raw data, which are collected in the spatial frequency domain (the "k-space").

The MR signal is influenced by a number of parameters that can be divided into two general categories: inherent tissue parameters and user-selectable imaging parameters. Inherent tissue MR parameters that affect MR signal intensity of a particular tissue include the proton density, i.e., hydrogen nuclei density of the tissue and its inherent $T_1$ and $T_2$ relaxation times. MR signal intensity is also influenced by other factors, such as tissue susceptibility difference, flow and chemical shift. The contrast (i.e., the difference of signal intensity) between two tissues, e.g., a tumor and normal tissue, can be maximized by proper use of user-selectable parameters, including the choice of pulse sequences, flip angles, echo time, repetition time and the use of contrast agents.

However, MRI measurements in general are limited by low sensitivity. Typical clinical MRI scanners only receive information from 1 in 200,000 molecules that are present in the human body. The low sensitivity of the measurements can prevent the clinical observation of the complex biochemistry in the human body. This low sensitivity means that opportunities may be missed for observing reaction intermediates, studying reaction mechanisms, and studying reaction kinetics. Sometimes MRI contrast between different tissues is not sufficient to obtain satisfactory clinical information, and therefore, MRI contrast agent is used to improve contrast. Contrast agents are an integral part of MR today, providing increased sensitivity and specificity critical to improving diagnosis, therapy and outcome. Contrast agent MRI are introduced to work by effecting the $T_1$, $T_2$ and/or $T_2^*$ relaxation times and thereby enhancing the contrast in the images.

Advances in contrast agent and the technical capabilities of MRI have increased the accuracy and utility of contrast-enhanced-MRI. Contrast agent MRI is a valuable and established diagnostic imaging tool worldwide, used annually in approximately 30 million procedures, which are around 40-50% of total MRI examinations worldwide. More than 300 million procedures have been performed to date [Lohrke J, et al. Advances in therapy. 2016; 33(1):1-28.]. Contrast agent MRI offers definitive diagnostic imaging, treatment guidance, and monitoring for a wide range of conditions. The administration of contrast agent can increase the contrast between normal tissue and pathological structures, to speed up image acquisitions and to provide additional information on the tissues and organs. The most commonly used contrast agent in clinical MRI is gadolinium-based (Gd-based) contrast agent due to its low cost, wide availability, efficacy, and general low-risk profiles. The first Gd-based contrast agent (Magnevist), became available for clinical use globally in 1988. Today, contrast-enhanced ("CE") MRI is an integral part of MR, providing increased sensitivity and specificity critical to improving diagnosis, therapy, and outcome. Studies shown that $T_1$ in brain tumors reduced on the order of 50% in the tumors with only marginal effects on gray and white matter $T_1$ values, while $T_2$ value of brain tumor reduced by around 4%. The $T_2$ effect from Gd-based contrast agent is generally negligible compared to $T_1$ changes, though $T_2$-darkening of signal can be found in regions of high Gd concentration. Therefore, $T_1$-weighted sequences are used after the administration of contrast agent [Aronen et al. Acta Radiol 1998; 39:474-481]. The role of CE-MRI will continue to grow in the future as new imaging techniques are integrated into clinical practice. The close relationship between clinical diagnosis and the monitoring of increasingly specific therapies is one of the most important areas for CE-MRI use, along with research into new MRI contrast agents.

Contrast agent MRI procedures have been performed for a wide range of diseases across human body. For example, contrast agent MRI is used: (1) to visualize lesions of patients with abnormal blood brain barrier or abnormalities of the brain, spine and associated tissues in Central Nervous System ("CNS"), such as brain tumor, multiple sclerosis and abscesses; (2) to visualize lesions of patients with liver structural abnormalities; and/or (3) to visualize of lesions with abnormalities in body, such as the thoracic, abdominal, and pelvic cavities. For example, contrast agent MRI is the diagnostic "gold standard" for multiple sclerosis (McDonald evaluation criteria). Furthermore, contrast agent MRI could improve the diagnostic efficacy of MRI, providing better visualization of the lesions and improving diagnosis in up to 40% of patients [van der Molen A J and Bellin M F. Eur J Radiol. 2008; 66(2):168-174.].

A number of challenges for contrast agent MRI are described below. The contrast change strongly depends on the concentration and relaxivity of the contrast agents on its bio-distribution. Generally, high doses and high relaxivity of contrast agent will bring better lesion-to-tissue contrast and improved lesion detection sensitivity. However, unnecessary high doses of contrast agents may lead to possible risk for health. Therefore, choice of contrast agent concentration is one of major issues for contrast agent MRI. Longer acquisition time for 3D acquisition restricts its application in clinic. It is desirable to finish the MRI protocol in the shortest amount of time because of patient comfort and economics. Additionally, the fast acquisition techniques can reduce the effect of patient and organ motion on image quality. It is important to catch the lesion-tissue contrast when contrast concentration is maximal in a lesion and complete the acquisition before contrast agent washout [De Stasio G, et al. Cancer research. 2001; 61(10):4272-7; Biswas J et al. Invest Radiol. 2005; 40(12):792-7; Essig M. Neuroradiology. 2006; 48 Suppl 1:3-8.]. The contrast agent could change the signal contrast of not only lesion vs. normal tissue, but also non-lesion area (normal tissue vs. normal tissue). Even in the absence of leakage, the presence of Gd in the capillary network of the brain parenchyma may slightly reduce $T_1$ relaxation of the brain tissue. The non-lesion enhancement and other artifacts (such as fat signal) can affect the visualization of lesion enhancement and lesion detection [Shah et al. AJR Am J Roentgenol. 2011; 197(3): 697-703.]. The suppression of these unnecessary signals and increase the visualization of lesion enhancement is important for the application of contrast agent MRI.

SUMMARY

This disclosure describes techniques to optimize imaging protocols for both 2D and 3D acquisitions to 1) minimize contrast agent concentration required to achieve clinical goals; 2) optimize acquisition time to keep maximal contrast concentration or lesion enhancement in lesion tissue; 3) suppress the healthy tissue enhancement and improve the detection sensitivity of contrast agent MRI; 4) optimize acquisition duration time of image acquisition and delayed acquisition to catch maximal lesion enhancement in lesion tissue after the administration of contrast agent. It should be understood that this disclosure contemplates using contrast agents other than Gd-based contrast agents, which are provided as an example only, with the techniques described herein. As a result, this disclosure makes contrast agent MRI safer, faster, and more effective for all research and, medical applications.

An example method for detecting lesion tissue using contrast agent magnetic resonance imaging ("MRI") is described herein. The example method can include simulating a plurality of relationships between an image quality metric and one or more imaging parameters. As discussed herein, relationships between the image quality metric and imaging parameters can be numerically simulated, for example, using Bloch Equations or other approximation. In addition, the method can include selecting a first set of imaging parameters to optimize an image quality metric of a first image that is acquired before administration of contrast agent; selecting a second set of imaging parameters to optimize a lesion enhancement metric or a detection sensitivity metric of a second image that is acquired after administration of contrast agent; and selecting an image acquisition time for the second image to maximize contrast agent concentration or the lesion enhancement metric or a detection sensitivity metric. The method can further include acquiring the first image before administration of contrast agent using the selected first set of imaging parameters; acquiring the second image after administration of contrast agent at the selected image acquisition time using the selected second set of imaging parameters; and generating a combined image from the first image and the second image.

Another example method for detecting lesion tissue using contrast agent magnetic resonance imaging ("MRI") is described herein. The example method can include simulating a plurality of relationships between an image quality metric and one or more imaging parameters. As discussed herein, relationships between the image quality metric and imaging parameters can be numerically simulated, for example, using Bloch Equations or other approximation. In addition, the method can include selecting a set of imaging parameters to optimize a lesion enhancement metric or a detection sensitivity metric of an image that is acquired after administration of contrast agent; and selecting an image acquisition time for the image to maximize the lesion enhancement metric or a detection sensitivity metric. The method can further include acquiring the image after administration of contrast agent at the selected image acquisition time using the selected set of imaging parameters.

As described herein, a lesion enhancement metric is used to describe the change in signal intensity of a lesion (also referred to herein as lesion tissue) in images, for example, in images acquired before and after the administration of contrast agent, respectively (e.g., the first and second images). In some cases (e.g., for $T_1$ contrast agent), signal intensity increases after administration of contrast agent. In other cases (e.g., for $T_2^*$ contrast agent), signal intensity decreases after administration of contrast agent. Accordingly, the lesion enhancement metric is an absolute change in signal intensity of a lesion in images acquired before and after administration of contrast agent.

As described herein, a detection sensitivity metric can optionally be a contrast metric. The contrast metric can optionally be one of contrast or contrast efficiency between lesion tissue and healthy tissue, contrast-to-noise ratio ("CNR") or CNR efficiency between lesion tissue and healthy tissue. It should be understood that in some cases administration of contrast agent does not result in lesion enhancement (i.e., change in signal intensity of a lesion). Accordingly, in these cases, imaging parameters can be selected to optimize detection sensitivity.

Optionally, the first set of imaging parameters can be the same as the second set of imaging parameters. Alternatively, the first set of imaging parameters can optionally be different than the second set of imaging parameters.

Alternatively or additionally, the first image and the second image can optionally be acquired using the same MRI sequence. Alternatively or additionally, the first image and the second image can optionally be acquired using different MRI sequences.

Alternatively or additionally, the one or more imaging parameters can include at least one of a repetition time ("TR"), echo time ("TE"), variable flip angle, variable refocusing angle, magnetization preparation pulses, fat saturation pulses, inversion times, radiofrequency ("RF") bandwidth, echo train length, echo space time, slab number, or readout radiofrequency ("RF") number.

Alternatively or additionally, the method can further include receiving one or more MRI scanner settings, and receiving one or more magnetic resonance ("MR") parameters for lesion tissue with and/or without contrast agent. The simulation of the plurality of relationships between the image quality metric and the one or more imaging parameters can be performed using at least one of the one or more MRI scanner settings or the one or more MR parameters. In other words, the MRI scanner setting(s) and/or the MR parameter(s) can be input into the simulation (e.g., the Bloch equations or other approximation). Alternatively or additionally, the one or more MRI scanner settings can include at least one of MRI sequence, static field strength, spatial-resolution, radiofrequency ("RF") bandwidth, echo space time, parallel acquisition, saturation, or magnetization preparation.

Alternatively or additionally, the image quality metric can include at least one of lesion location, lesion border delineation, lesion morphology, contrast or contrast efficiency between lesion tissue and healthy tissue, contrast-to-noise ratio ("CNR") or CNR efficiency between lesion tissue and healthy tissue, signal intensity, signal intensity efficiency, or image artifact.

Alternatively or additionally, the image artifact can include at least one of susceptibility artifact, geometry distortion, signal inhomogeneity, cross excitation, cross-talk artifact, motion, chemical shift artifact, or contrast agent leakage into healthy tissue.

In some implementations, the method can optionally further include estimating the image quality metric from at least one image. For example, the image quality metric can be estimated from a single images such as the first image or the second image individually. Alternatively, the image quality metric can be estimated from multiple images such as both the first and second images.

In some implementations, optimizing the image quality metric includes at least one of optimizing a contrast metric and/or detection sensitivity metric; minimizing image artifact; or optimizing a signal intensity of lesion tissue. Optionally, in some implementations, optimizing the lesion enhancement metric includes maximizing the lesion enhancement metric.

In some implementations, the method can include optimizing a k-space strategy for acquiring the first image or the second image. Techniques for optimizing k-space strategy are described in U.S. Pat. No. 9,339,239 to Wang et al., issued May 17, 2016, entitled "Methods and Devices for Optimization of Magnetic Resonance Imaging Protocols."

In some implementations, the method can include optimizing an acquisition train length of an MRI sequence for acquiring the first image or the second image. Techniques for optimizing an acquisition train length of an MRI sequence are described in WO 2016/145355 to Wang et al., filed Mar. 11, 2016, entitled "Methods and Devices for Optimizing Magnetic Resonance Imaging Protocols."

In some implementations, the method can include using the combined image for medical diagnostics or medical treatment. For example, medical treatment can optionally include at least one of a diagnostic procedure, an intervention procedure, or a therapeutic procedure. Alternatively or additionally, using the combined image for medical diagnostics or medical treatment can optionally include providing a visualization and localization of healthy tissue adjacent to lesion tissue to avoid damaging the healthy tissue during the medical treatment.

Alternatively or additionally, in some implementations, the method can optionally include at least one of diagnosing a disease, monitoring disease therapy, or staging a disease.

Alternatively or additionally, in some implementations, the method can further include using the combined image for medical diagnostics or medical treatment such as, for example, providing a visualization and localization of healthy tissue adjacent to lesion tissue to avoid damaging the healthy tissue during treatment. Medical treatment can include, but is not limited to, a diagnostic procedure, an intervention procedure, or a therapeutic procedure.

Alternatively or additionally, in some implementations, the image acquisition time can optionally be a start time of acquisition and an acquisition duration time.

Alternatively or additionally, in some implementations, the lesion tissue can optionally be at least one of tumor, multiple sclerosis, inflammation disease, infection disease, stroke, traumatic nerve injury, stroke, vascular disease, musculoskeletal disease, or MR angiography.

Alternatively or additionally, in some implementations, the contrast agent can optionally be at least one physiologically acceptable paramagnetic substance, superparamagnetic substance, or ferromagnetic substance.

Alternatively or additionally, in some implementations, the contrast agent can optionally be at least one of a magnetic small-molecule-based compound, a magnetic large-molecule-based compound, or a magnetic nanoparticle-based compound. Optionally, the contrast agent is administered by injection or orally.

Alternatively or additionally, in some implementations, the contrast agent can optionally be gadolinium-based, iron-based, or manganese-based products. It should be understood that the contrast agent should not be limited to these examples.

Alternatively or additionally, in some implementations, the MRI sequence includes at least one of gradient echo, spin echo, gradient echo train, or spin echo train acquisition with or without magnetization preparation and/or specific tissue suppression. For example, fat saturation and/or CSF suppression.

Alternatively or additionally, in some implementations, the MRI sequence can be at least one of 2-dimensional acquisition or 3-dimensional acquisition.

An example method for suppressing leakage of contrast agent in an image is described herein. The method can include performing image processing to suppress leakage of the contrast agent into healthy tissue; or selecting a magnetic resonance imaging ("MRI") sequence to suppress leakage of the contrast agent into the healthy tissue. This disclosure contemplates that the method for suppressing leakage of contrast agent can be used with the methods of detecting lesion tissue using contrast agent magnetic resonance imaging ("MRI") described herein. In other words, the method for suppressing leakage of contrast agent can be used to suppress leakage of contrast agent in the image acquired after contrast agent administration.

Optionally, performing image processing to suppress leakage of the contrast agent into healthy tissue can include receiving a pre-contrast image and a post-contrast image; comparing the pre-contrast image and the post-contrast image to identify an enhanced healthy area; segmenting the enhanced healthy area in the pre-contrast image; extracting the segmented enhanced healthy area in the pre-contrast image as a marker; and applying the marker onto the post-contrast image to suppress the enhanced healthy area.

Alternatively or additionally, selecting a magnetic resonance imaging ("MRI") sequence to suppress leakage of the contrast agent into the healthy tissue can include at least one of modifying the MRI sequence to suppress leakage of the contrast agent into the healthy tissue; optimizing one or more imaging parameters to suppress leakage of the contrast agent into the healthy tissue; or optimizing an image acquisition time to suppress leakage of the contrast agent into the healthy tissue according to wash-in and wash-out of the contrast agent in the healthy tissue and the lesion tissue.

Optionally, modifying the MRI sequence can include determining a targeted MRI property based on a difference between enhanced healthy and lesion tissues; designing or modifying the MRI sequence based on the targeted MRI property; selecting one or more imaging parameters to null or reduce the enhanced healthy tissue; and acquiring the post-contrast image using the selected one or more imaging parameters. Optionally, the MRI parameter includes at least one of $T_1$, $T_2$, diffusion coefficient, chemical shift, Larmor frequency, or flow.

An example method for performing contrast agent magnetic resonance imaging ("MRI") is described herein. The example method can include receiving a time course of lesion enhancement or contrast agent concentration; receiving a magnetic resonance imaging ("MRI") sequence and one or more imaging parameters; selecting an image acquisition time for image acquisition after administration of contrast agent to match k-space sampling of the MRI sequence with the time course of lesion enhancement or contrast agent concentration; and acquiring a post-contrast image at the selected image acquisition time.

In some implementations, receiving a time course of lesion enhancement or contrast agent concentration includes measuring the time course of lesion enhancement or contrast agent concentration using an imaging modality; or retrieving the time course of lesion enhancement or contrast agent concentration from memory (e.g., based on published information). As described herein, the time course of lesion enhancement or contrast agent concentration can be retrieved by a computing device. Optionally, the imaging modality includes at least one of ultrasound, positron emission tomography, dynamic enhanced contrast MRI, or dynamic susceptibility contrast MRI.

In some implementations, the image acquisition time is selected based on at least one of a start time of k-space sampling; a duration of k-space sampling; or a time of k-space sampling for the low spatial frequency k-space data.

In some implementations, selecting an image acquisition time for image acquisition after administration of contrast agent to match k-space sampling of the MRI sequence with the time course of lesion enhancement or contrast agent concentration includes selecting a time of maximum contrast agent concentration or maximum signal intensity in lesion tissue to correspond to a time of k-space center acquisition; selecting a time of relatively higher contrast agent concentration and signal intensity in lesion tissue; or avoiding a time of relatively lower contrast agent concentration in lesion tissue. It should be understood that relatively higher contrast agent concentration and lesion enhancement correspond to relatively low spatial frequency k-space data acquisition, and relatively lower agent concentration and lesion enhancement correspond to relatively high spatial frequency k-space data acquisition.

An example method for combining a pre-contrast image and a post-contrast image is described herein. The example method can include receiving a pre-contrast image and a post-contrast image; co-registering the post-contrast image into the pre-contrast image; extracting a region of interest from the registered post-contrast image; and combining the extracted region of interest into the pre-contrast image at a corresponding image location to form a combined image. This disclosure contemplates that the method for combining a pre-contrast image and a post-contrast image can be used with the methods of detecting lesion tissue using contrast agent magnetic resonance imaging ("MRI") described herein.

Optionally, the region of interest includes at least one of a lesion, a landmark, a texture, or a feature of interest.

In some implementations, the region of interest can be extracted from the registered post-contrast image using a histogram-based, edge detection, region-growing, level clustering, or level set method.

In some implementations, the extracted region of interest can be combined into the pre-contrast image using at least one of Intensity-hue-saturation (IHS) transform based fusion, Principal component analysis based fusion, or multi scale transform based fusion. Optionally, multi scale transform based fusion includes at least one of High-pass filtering method, pyramid method, wavelet transforms, or curvelet transforms.

An example method for determining an optimal contrast agent concentration for contrast agent MRI imaging is described herein. The example method can include receiving a magnetic resonance imaging ("MRI") sequence; receiving a targeted image quality metric; simulating a plurality of relationships among the targeted image quality metric, one or more imaging parameters, and contrast agent concentration; selecting a set of imaging parameters and a contrast agent concentration to optimize a lesion enhancement metric or a detection sensitivity metric after administration of contrast agent; administrating a contrast agent at the selected contrast agent concentration; and acquiring a post-contrast image after administration of the contrast agent using the selected one or more imaging parameters. This disclosure contemplates that the user can select a desired MRI scanner and/or user-selectable MRI scanner parameter(s) and/or an MRI sequence. As discussed herein, the relationship among an image quality metric, imaging parameters, and contrast agent concentration can be estimated using Bloch equations or other numerical approximation, for example.

In some implementations, the targeted image quality metric can be determined diagnostically or according to requirements for the visualization of morphological, structural or pathological lesion tissue or modifications or alterations of the lesion tissue.

Optionally, the targeted image quality metric includes at least one of a contrast metric, lesion enhancement metric, contrast per concentration, or image artifact.

Alternatively or additionally, the one or more user-selectable parameters can be at least one of magnetization preparation, motion correction, parallel image acquisition, spatial-resolution, radiofrequency bandwidth, echo spacing time, echo time, or scan time.

In some implementations, the method further includes acquiring an image after administration of the optimal concentration of contrast agent to the subject. Optionally, the contrast agent can be administered at a reduced contrast agent concentration to achieve the targeted image quality metric.

Alternatively or additionally, in some implementations, the image acquisition time can optionally be a start time of acquisition and an acquisition duration time.

Alternatively or additionally, in some implementations, the lesion tissue can optionally be at least one of tumor, multiple sclerosis, inflammation disease, infection disease, stroke, traumatic nerve injury, stroke, vascular disease, musculoskeletal disease, or MR angiography.

Alternatively or additionally, in some implementations, the contrast agent can optionally be at least one physiologically acceptable paramagnetic substance, superparamagnetic substance, or ferromagnetic substance.

Alternatively or additionally, in some implementations, the contrast agent can optionally be at least one of a magnetic small-molecule-based compound, a magnetic large-molecule-based compound, or a magnetic nanoparticle-based compound. Optionally, the contrast agent is administered by injection or orally.

Alternatively or additionally, in some implementations, the contrast agent can optionally be gadolinium-based, iron-based, or manganese-based products. It should be understood that the contrast agent should not be limited to these examples.

Alternatively or additionally, in some implementations, the MRI sequence includes at least one of gradient echo, spin echo, gradient echo train, or spin echo train acquisition with or without magnetization preparation and/or specific tissue suppression. For example, fat saturation and/or CSF suppression.

Alternatively or additionally, in some implementations, the MRI sequence can be at least one of 2-dimensional acquisition or 3-dimensional acquisition.

It should be understood that the above-described subject matter may also be implemented as a computer-controlled apparatus, a computer process, a computing system, or an article of manufacture, such as a computer-readable storage medium.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

The components in the drawings are not necessarily to scale relative to each other. Like reference numerals designate corresponding parts throughout the several views.

FIGS. 11A-11B illustrates in vivo brain images acquired using the MP-RAGE sequence with different imaging parameters: optimized parameters for pre-contrast image (FIG. 11A) and post-contrast image (FIG. 11B) after the administration of 0.1 mmol/kg Gadavist.

DETAILED DESCRIPTION

Figure 1:
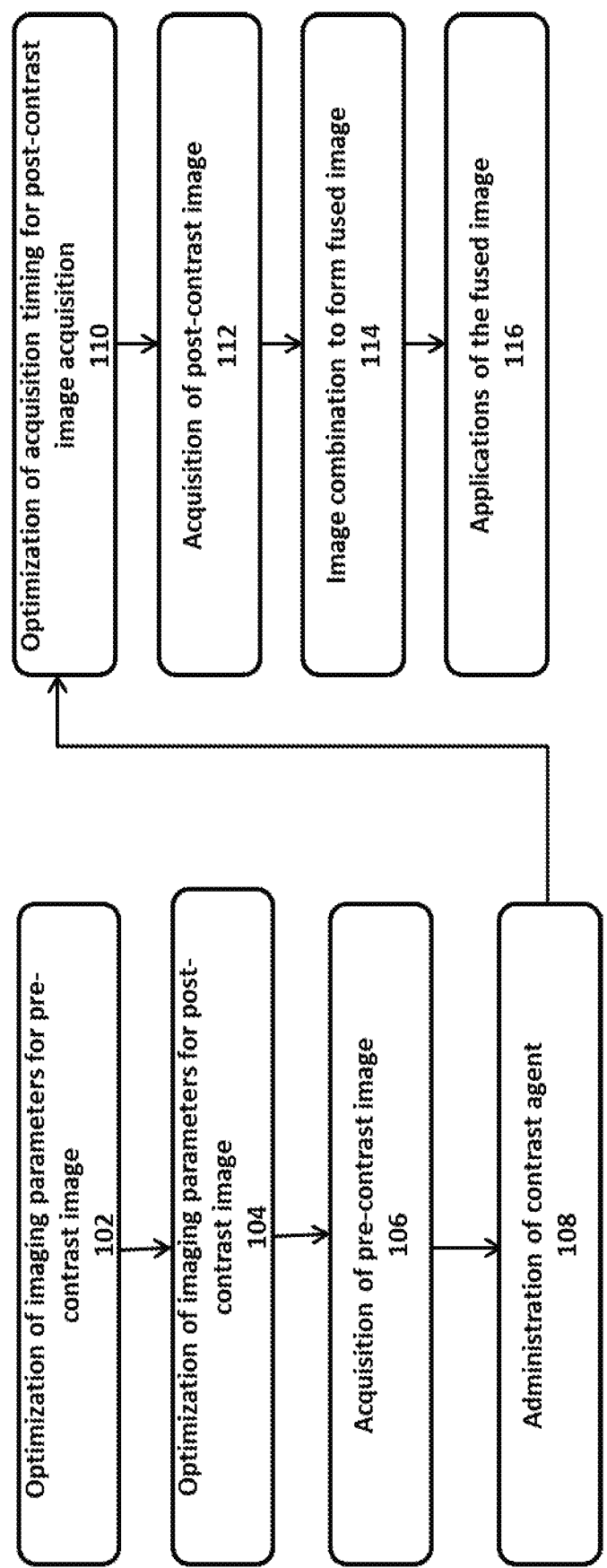
FIG. 1 is a flow chart illustrating example operations for optimization of contrast agent MRI acquisition according to one example of the present disclosure.

Unless defined otherwise, all technical and scientific terms used herein have the same meaning as commonly understood by one of ordinary skill in the art. Methods and materials similar or equivalent to those described herein can be used in the practice or testing of the present disclosure. As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms. The terms "optional" or "optionally" used herein mean that the subsequently described feature, event or circumstance may or may not occur, and that the description includes instances where said feature, event or circumstance occurs and instances where it does not. While implementations will be described for optimizing the imaging parameters for contrast agent MRI and/or administration contrast agent concentration with regard to MRI modalities, it will become evident to those skilled in the art that the implementations are not limited thereto, but are applicable to other image modalities such as, computed tomography, for example. Additionally, this disclosure contemplates that MRI modalities include MRI techniques with administration of contrast agents, for example, contrast enhanced MR angiography. This disclosure contemplates that the images obtained using the techniques described herein can be directly employed in at least one of diagnosing diseases, monitoring therapy responses, conducting treatment plans, and/or improving quantification of MRI. For example, the techniques described herein can be used for the diagnoses of specific diseases such as the standardization of the MRI protocol in brain tumor. Additionally, the techniques described herein are optionally applicable to a group of individuals in a similar pathphysiological situation.

Said contrast agent MRI includes contrast-enhanced MRI in which $T_1$ contrast agent is administered, and susceptibility contrast MRI in which $T_2$ contrast agent is administered. The contrast agents used for contrast-enhanced MRI are often gadolinium-based. Gadolinium injection causes the relaxation time to lesion, and therefore images acquired after gadolinium injection have higher signal. $T_1$-weighted MRI sequence is generally used to detect the lesion after the administration of $T_1$ contrast agent. $T_1$-weighted MRI sequence is one of the basic pulse sequences in MRI and generates image contrast of tissues based on the differences in the $T_1$ relaxation times of tissues. $T_1$-weighted sequence includes gradient echo-based and spin echo-based sequences. $T_1$-weighted gradient echo-based includes $T_1$-weighted gradient echo sequence with or without magnetization preparation, and their combination with any of saturation pulses. The saturation pulses include fat saturation pulses, flow saturation pulses, are not limit thereto. With regard to susceptibility contrast MRI, $T_2$-weighted and/or $T_2^*$-weighted MRI sequences are generally used to detect the lesion after the administration of $T_2$ contrast agent. $T_2$-weighted sequence includes spin echo and fast spin echo sequence with and/or without magnetization preparation and saturation pulses. $T_2^*$-weighted MRI sequence includes gradient echo and fast gradient echo at the relative long echo time with and/or without magnetization preparation and saturation pulses. While implementations and methodologies will be described for optimizing the imaging parameters and/or administered contrast agent concentration with regard to contrast-enhanced MRI, it will become evident to those skilled in the art that the implementations are applicable to the susceptibility contrast MRI.

Image Quality Metric for Contrast Agent MRI

The image quality metric for contrast agent MRI can include at least one of spatial resolution, slice thickness, signal intensity, signal-to-noise ratio (SNR), SNR efficiency, contrast, contrast-to-noise ratio (CNR), CNR efficiency, enhancement of lesion, enhancement of lesion efficiency, and/or image artifact. As described herein, contrast is the difference in signal intensity between different types of tissue in an image. The different types of tissue can be lesion (or tumor, diseased, pathological, etc.) tissue and non-lesion (or healthy, non-diseased, non-pathological, etc.) tissue. Optionally, the different types of tissue can be in proximity to each other or adjacent to one another. For example, non-lesion tissue can at least partially surround lesion tissue. As described herein, lesion enhancement (EL) (or lesion enhancement metric) is used to describe the change in signal intensity of a lesion (also referred to herein as lesion tissue) in images, for example, in images acquired before and after the administration of contrast agent, respectively (e.g., the first and second images). In some cases (e.g., for $T_1$ contrast agent), signal intensity increases after administration of contrast agent. In other cases (e.g., for $T_2^*$ contrast agent), signal intensity decreases after administration of contrast agent. Accordingly, the lesion enhancement metric is an absolute change in signal intensity of a lesion in images acquired before and after administration of contrast agent. The image artifact can include at least one of geometry distortion, signal inhomogeneity, chemical shift, motion, image blurring, and/or signal loss.

SNR is used in imaging as a physical measure of the sensitivity of an imaging system which is defined as:

$$SNR = \mu_{signal}/\sigma_{background} \quad (1)$$

where $\mu_{signal}$ is the average signal intensity of region of interest (ROI). $\sigma_{background}$ is the standard deviation of signal intensity of background region.

The SNR efficiency, $SNR_{eff}$, is used to quantitatively evaluate image quality and efficiency. It is defined as SNR per square root total scan time (TA), is given by Eq. 2 below.

$$SNR_{eff} = SNR/\sqrt{TA} \quad (2)$$

A single type of tissue may have different signal intensities because of signal inhomogeneity caused by non-uniform transmit field and receive sensitivity. Thus, SNR of the single tissue may not be the best metric to evaluate image quality sometimes. Instead, global SNR can be used as an indicator to evaluate the image quality at that case, avoiding the error caused by signal inhomogeneity.

As used herein, contrast is defined as:

$$Contrast = \mu_A - \mu_B, \quad (3)$$

where $\mu_A$ and $\mu_B$ are the average signal value of regions A and B, respectively. It should be understood that other definitions of contrast can also be used as the objective function, such as Weber contrast and Michelson contrast, for example.

CNR is used as a metric to determine image quality, and is defined as:

$$CNR = Contrast/\sigma_{background}; \quad (4)$$

The CNR efficiency is defined as CNR per square root of total scan time (TA) as given by Eq. 5 below:

$$CNR_{eff} = CNR/\sqrt{TA}; \quad (5)$$

The enhancement of lesion (EL) (also referred to herein as a lesion enhancement metric) is used to describe the change in signal intensity of a lesion (also referred to herein as lesion tissue) in images acquired before and after the administration of contrast agent, respectively. It is noted that Gd-related $T_2$-shortening generally reduces signal and works against the $T_1$-related signal enhancement. In order to simultaneously cover both $T_1$ contrast agent and $T_2^*$ contrast agent described herein, the lesion enhancement metric is absolute MR signal change before and after the administration of contrast agent, that is, the lesion enhancement metric (EL) is defined by Eq. 6 below:

$$EL[\%] = \left|\frac{S_a - S_b}{S_b}\right| \cdot 100; \quad (6)$$

$S_b$ and $S_a$ are the signal intensity of an lesion region of interest (ROI) before and after the administration of contrast agent, respectively. In order to describe the efficiency of contrast agent, the enhancement efficiency $EL_{eff}$ is introduced and it is defined as EL per square root of total scan time (TA) as given by Eq. 7 below:

$$EL_{eff} = EL/\sqrt{TA}, \quad (7)$$

Any of the image quality metrics defined above can be used as objective functions for the optimization for both pre-contrast imaging and post-contrast imaging. It should be understood that this disclosure is not limited to using the image quality metrics described herein. This disclosure contemplates that the method of data analysis will determine whether or not the objective functions for both pre-contrast and post-contrast imaging should be applied.

Early methods for optimizing imaging parameters focused on maximizing SNR, which resulted in SNRs far in excess of what is required to detect pathologies being investigated in current clinical MRI systems. In most cases, the contrast and/or its efficiency between normal and diseased tissues, not the SNR, is a better metric for diagnostic sensitivity and specificity of the disease. One goal for optimizing imaging parameters can therefore be maximizing tissue contrast, or contrast-to-noise ratio (CNR) and/or CNR efficiency instead of SNR-based metric for both pre-contrast image and post-contrast images. With the optimization of magnetization prepared rapid acquisition gradient echo (MPRAGE), k-space strategies [Wang J et al. U.S. Pat. No. 9,339,239 B2; Wang J et al. PLOS ONE. 2014; 9: e96899] and echo train acquisition [Wang J et al. WO 2016/145355 A1] can be optimized to improve the image quality and imaging efficiency. As described herein, the optimization method of imaging parameters is extended from non-contrast agent imaging to both pre-contrast and post-contrast imaging. As used herein, a pre-contrast image is an image acquired before administration of contrast agent (or without contrast agent administration), and a post-contrast image is an image acquired after administration of contrast agent (or with contrast agent). Though pre-contrast imaging is non-contrast agent imaging, the objective function for pre-contrast imaging can optionally be different from non-contrast agent imaging since the goals for two images acquired are different in clinical applications at most cases. Additionally, enhancement and/or enhancement efficiency which is an important quality metric for contrast agent MRI is added to objective function library. For non-contrast agent imaging, the objective function library can be estimated or simulated from different tissues in single image or the image itself, while enhancement and/or enhancement efficiency for contrast agent imaging are estimated or simulated from two images—both pre-contrast image and post-contrast image. That is, in present disclosure, the objective function or image quality metric can be determined by the image itself, other images, and/or their combination. Additionally, the optimization can be available without any change of both k-space strategies and echo train acquisition which is comprised of a series of radiofrequency refocusing pulses and/or bipolar readout gradient, for example 2D and/or 3D fast low angle shot (FLASH) sequences, while the excellent performance in the MPRAGE optimization mainly resulted from these two factors [Wang J et al. PLOS ONE. 2014; 9: e96899; Wang J et al. *Magnetic Resonance Imaging*. 2017; 38:224-232]. Additionally, the pre-contrast and post-contrast images can be acquired with different imaging or MRI sequences, each with different optimal imaging parameters, respectively. Alternatively, the pre-contrast and post-contrast images can be acquired with the same imaging or MRI sequences with the same optimal imaging parameters. For example, the pre-contrast image is able to be acquired with optimal MPRAGE sequence, but the post-contrast image is able to be acquired with 3D FSE with variable flip angles. Actually, a recent study shows that significantly more lesions are detected with $T_1$-weighted 3D FSE with variable flip angles compared to the MPRAGE for cerebral malignomas because it increases the contrast of lesions significantly and might therefore improve detection rates of small lesions in early stages of disease [Kammer N et al. European radiology. 2015:1-8]. This disclosure describes (a) how to apply sequence optimization for reducing the risk of safety, while the imaging or MRI sequence is optimized for reducing the administration dose of contrast agent; (b) combining post-contrast image with pre-contrast image to improve the efficacy in medical applications; (c) how to optimize acquisition timing for post-contrast imaging; (d) how to suppress the image artifacts, particularly non-lesion enhancement.

Generally, imaging parameters are usually iteratively optimized through multiple scans of a subject. Because the process is very time-consuming and cost-intensive, particularly in the case with very long acquisition time, the experimental approach is usually not practical in clinical settings. In the techniques described herein, signal intensities for interested tissues are numerically simulated, for example, using at least one of Bloch Equation and/or quantum mechanics, extended phase graph (EPG)-algorithm and their approximations with known tissue and lesion MR parameters (such as $T_1$, $T_2$, proton density) that are either measured or obtained from the literatures. Further, the relationship between an objective function and imaging parameters can be estimated from the signal intensity. The initial optimized image parameters can be determined based on optimized objective function and minimizing artifacts as well as noise.

While implementations will be described for optimizing the imaging parameters for contrast agent MRI and/or administration contrast agent concentration with regard to MRI modalities, it will become evident to those skilled in the art that the implementations are not limited thereto, but are applicable to other image modalities such as, computed tomography, for example.

1. MRI Sequence for Contrast Agent MRI

An MRI sequence is combination of a set of defined RF and gradient pulses. All MRI sequences, including gradient echo-based and spin echo-based sequences, can be used for contrast agent MRI. A gradient echo is generated by using a pair of bipolar gradient pulses. The gradient echo-based sequences include at least one of spoiled gradient echo, balanced steady state free precession, unbalanced steady state gradient echo, echo planar with and/or without magnetization preparation (such as MPRAGE). A spin echo is generated by using a refocusing radiofrequency pulse. Spin echo-based sequences include spin echo, fast spin echo, spin echo planar, with and/or without magnetization preparation (such as fluid-attenuated inversion recovery sequence, short inversion-time recovery sequence) acquisitions. Contrast agent MRI is also applicable for hybrid gradient echo and spin echo sequences (such as gradient- and spin-echo sequence).

These sequences are able to combine with any fast imaging techniques, including at least one of parallel imaging, simultaneously multi-slice, simultaneously multi-slab, k-space under-sampling technique (such as compressive sensing, compressive sampling, or sparse sampling). The signal intensity for a given sequence can be estimated from at least one of Bloch Equation and/or quantum mechanics, extended phase graph (EPG)-algorithm and their approximation solutions of spin evolution. In the present disclosure, these algorithms can be used to optimize imaging parameters for a given sequence with and/or without the administration of contrast agent. For examples:

a). MP-RAGE (or MPRAGE) Sequence

The MP-RAGE sequence is composed of 3D-inversion recovery α and N equally-spaced readout RF pulses of flip angle θ and echo spacing τ. Repetition time TR is defined as the time interval between two successive inversion recovery pulses as shown by Eq. 8 below.

$$TR = TI + N \cdot \tau + TD, \qquad (8)$$

where $\tau$ is echo spacing time, N is the total number of readout RF pulses, TI is the time interval between the inversion recovery pulse and the first RF readout pulse, and TD is delay time. In order to simplify the formula for signal intensity, $\gamma = \exp(-TI/T_1)$, $\delta = \exp(-\tau/T_1)$, $\rho = \exp(-TR/T_1)$, $\varphi = \exp(-TD/T_1)$, and $\mu = \delta \cdot \cos(\theta)$ are defined. For successive excitations in the MP-RAGE sequence, signal intensity from the $i^{th}$ read-out pulse is given by Eq. 9 below.

$$s_i \propto M_i^- \cdot \sin(\theta) = \qquad (9)$$
$$M_0 \cdot \sin(\theta) \cdot \left\{ \frac{(1-\delta)[1-\mu^{i-1}]}{1-\mu} + (\mu)^{i-1} \cdot (1-\gamma) - \gamma \cdot \mu^{i-1} \cdot \frac{M_{eq}}{M_0} \right\},$$

where the steady state magnetization $M_{eq}$ after several TRs is given by Eq. 10 below [Wang J et al. U.S. Pat. No. 9,339,239 B2; Wang J et al. PLOS ONE. 2014; 9: e96899].

$$M_{eq} = \frac{1 - \varphi + \frac{\varphi \cdot \cos(\theta) \cdot (1-\delta)[1-\mu^{N-1}]}{1-\mu} + }{1 - \rho \cdot \cos(\alpha) \cdot \cos^N(\theta)} \cdot M_0, \qquad (10)$$

b). 2D & 3D FLASH Sequences

The FLASH sequence is composed of a series of N equally-spaced readout RF pulses of flip angle $\theta$ and the repetition time. N is the total number of readout RF pulses, TI is inversion recovery time, and TD is delay time. In order to simplify the formula of signal intensity, $\alpha = \exp(-TR/T_1)$, and $\beta = \alpha \cdot \cos(\theta)$. For successive excitations in FLASH sequence, the signal intensity after the $i^{th}$ excitation pulse is given using Eq. 11 below.

$$s_i \propto M_i \cdot \sin(\theta) \approx M_0 \cdot \sin(\theta) \cdot \frac{(1-\alpha)[1-\beta^{i-1}]}{1-\beta}. \qquad (11)$$

where $M_0$ is the equilibrium magnetization at the location x. It is very difficult to simulate the noise exactly because noise in MRI includes not only white noise but also physiological noise. Additionally, white noise is relatively stable in MR experiments. Thus, it is assumed that noise is dominant and stable at the different imaging parameters in the simulation. The tissue type 1-tissue type 2 CNR efficiency ($CNReff_{tissue\ 1-tissue2}$) at a total scan time TA is given by Eq. 12 below.

$$CNReff_{tissue\ 1-tissue\ 2}(x) \propto \qquad (12)$$
$$\left[ M_{tissue\ 1} \cdot \frac{1-\alpha_{tissue\ 1}}{1-\beta_{tissue\ 1}} - M_{GM} \cdot \frac{1-\alpha_{tissue\ 2}}{1-\beta_{tissue\ 2}} \right] \cdot \sin(\theta(x)) \cdot \frac{1}{\sqrt{TA}} \propto$$
$$\left[ M_{tissue\ 1} \cdot \frac{1-\alpha_{tissue\ 1}}{1-\beta_{tissue\ 1}} - M_{GM} \cdot \frac{1-\alpha_{tissue\ 2}}{1-\beta_{tissue\ 2}} \right] \cdot \sin(\theta(x)) \cdot \frac{1}{\sqrt{TR}},$$

where $M_{tissue\ 1}$ and $M_{tissue\ 2}$ are the equilibrium magnetization of tissue type 1-tissue type 2, respectively. $\alpha_{tissue1} = \exp(-TR/T_{1,tissue1})$, $\alpha_{tissue2} = \exp(-TR/T_{1,tissue2})$, $\beta_{tissue1} = \alpha_{tissue1} \cdot \cos(\theta(x))$ and $\beta_{tissue2} = \alpha_{tissue2} \cdot \cos(\theta(x))$. $T_{1,tissue1}$ and $T_{1,tissue2}$ are the longitudinal relaxation times of tissue type 1-tissue type 2. One objective of the optimization procedure is to maximize the contrast efficiency between tissue type 1-tissue type 2, and reduce signal inhomogeneity using optimal imaging parameters (TR, $\theta$) at a relatively short scan time.

c). 2D and 3D Fast Spin Echo-Based Sequences

Spin-echo-based sequences are used widely in clinical MRI because they provide a variety of image contrasts that highlight pathology and reduced image artifacts from susceptibility difference and static field inhomogeneity. Both 2D and 3D fast spin echo sequences are also widely used for contrast agent MRI. Various analytic and numerical algorithms [Weigel M et al. Magnetic resonance in medicine. 2010; 63(1):230-234; Lukzen N et al. Journal of Magnetic Resonance. 2009; 196(2):164-169; Hennig J et al. Magnetic resonance in medicine. 2004; 51(1):68-80; Alsop D C. Magnetic resonance in medicine. 1997; 37(2):176-184; Hennig J. Concepts in Magnetic Resonance. 1991; 3(4):179-192; Busse R F. Magnetic resonance in medicine. 2004; 51(5):1031-1037], including extended phase graph (EPG)-algorithm [Hennig J. Concepts in Magnetic Resonance. 1991; 3(4):179-192; Busse R F. Magnetic resonance in medicine. 2004; 51(5):1031-1037] and pseudo-steady state solution algorithm [Alsop D C. Magnetic resonance in medicine. 1997; 37(2):176-184], have been used to describe the signal intensity of spin echo-based acquisition. Generally, conventional 3D fast spin echo sequences take several tens minutes for sizeable volume coverage and limits their clinical application. Most recent years, 3D fast spin echo (or SPACE in Siemens, VISTA in Philips, CUBE in GE) have been optimized in clinically acceptable acquisition times through shortening the echo spacing, suppressing blurring with variable flip angles refocusing radio-frequency pulses, and increasing the useable duration of the spin-echo train. 3D fast spin echo sequences are growing in clinical application, including non-contrast agent and contrast agent MRI. Since these techniques apply relatively high, constant flip angles for the refocusing RF pulses for the lower k-space acquisition, there are subtle contrast differences between 2D and 3D fast spin echo. In present disclosure, a technique is described to optimize 3D fast spin echo-based sequence for contrast agent MRI with the use of one or more method for optimizing image quality metric. The technique uses at least one of analytic solution [Lukzen N et al. Journal of Magnetic Resonance. 2009; 196(2):164-169;], extended phase graph (EPG)-algorithm [Hennig J. Concepts in Magnetic Resonance. 1991; 3(4):179-192; Busse R F. Magnetic resonance in medicine. 2004; 51(5):1031-1037], pseudo-steady-state solution algorithm [Alsop D C. Magnetic resonance in medicine. 1997; 37(2):176-184], or windowed ramp approach [Busse R F. Magnetic resonance in medicine. 2004; 51(5):1031-1037]. For example, the signal of a spin-echo sequence can be obtained by solving the Bloch's equation as follows:

$$SI(x) \propto M_0 \frac{\sin\alpha_{SE}(x) \cdot [1-\cos(\beta_{SE}(x))] \cdot \left[ 1 - \cos\beta_{SE}(x) \cdot E_1 - (1-\cos\beta_{SE}(x)) \cdot E_1 \cdot e^{\frac{TE}{2T_1}} \right]}{1 - \cos\alpha_{SE}(x) \cdot \cos\beta_{SE}(x) \cdot E_1} \cdot e^{-\frac{TE}{T_2}} \qquad (13)$$

where $\alpha_{SE}(x)$ and $\beta_{SE}(x)$ are the corrected flip angles of the excitation and refocusing pulses at position x, where $E_1 = \exp(-TR/T_1)$, $T_1$ is the longitudinal relaxation time. When $T_1 \gg TE$ and $TR \gg T_1$, Eq. (14) can be simplified to:

$$SI(x) \propto \sin\alpha_{SE}(x) \cdot \sin^2 \frac{\beta_{SE}(x)}{2}. \qquad (14)$$

Generally, at least one of image quality metric described above can be used as an objective function of protocol or sequence for computer simulation which generates the relationship between the objective function and the imaging parameters. That is, at least one of equations 1-14 can be used for computer simulation, for example. It is noted that there is no analytic solution for Bloch Equation for complex sequences. For example, 3D fast spin echo with variable flip angle sequences (such as SPACE in Siemens, CUBE in GE, and VISTA in Phillips), signal intensity are described using one of approximation solution, numerical solution, and EPG algorithm (or coherence pathway). Here complex sequences comprise of at least one of variable TR, flip angle, bandwidth, echo time, echo number, and phase of radiofrequency pulses.

2. Simulation of Contrast Agent MRI

FIG. 1 shows a flow diagram of optimization of contrast agent MRI acquisition and data processing according to one example in the present disclosure. It should be understood that the technique of FIG. 1 can be used to detect lesion tissue. The optimization can include simulating a plurality of relationships between an image quality metric and one or more imaging parameters. In some implementations, the simulation can be based on MRI scanner setting(s) and/or MR parameter(s) for lesion tissue. The optimization can include the following steps: (a) Optimization of imaging parameters (e.g., the first set of imaging parameters) for acquiring a pre-contrast image (e.g., to optimize the image quality metric) at 102; (b) Optimization of imaging parameters (e.g., the second set of imaging parameters) for acquiring a post-contrast image (e.g., to optimize a lesion enhancement metric or a detection sensitivity metric) at 104; (c) Acquisition of pre-contrast image (e.g., a first image) using the first set of imaging parameters at 106; (d) administration of contrast agent to the subject at 108; (e) Optimization of acquisition timing for post-contrast image acquisition (e.g. to optimize a lesion enhancement metric or a detection sensitivity metric) at 110; (f) Acquisition of post-contrast image (e.g., a second image) at the selected image acquisition time using the second set of imaging parameters at 112; and (g) Image combination to form fused image (e.g., generating a combined image from the pre-contrast image and the post-contrast image) at 114. Optionally, the technique can include medical applications of the fused image at 116. As described herein, the imaging parameters can be selected by optimizing an objective function (e.g., an image quality metric, a lesion enhancement metric, a detection sensitivity metric) using an analytic solution, an EPG algorithm, a pseudo-steady-state algorithm, a windowed ramp function, or Bloch equations, for example.

a). Optimization of Imaging Parameters for Pre-Contrast

Figure 2:
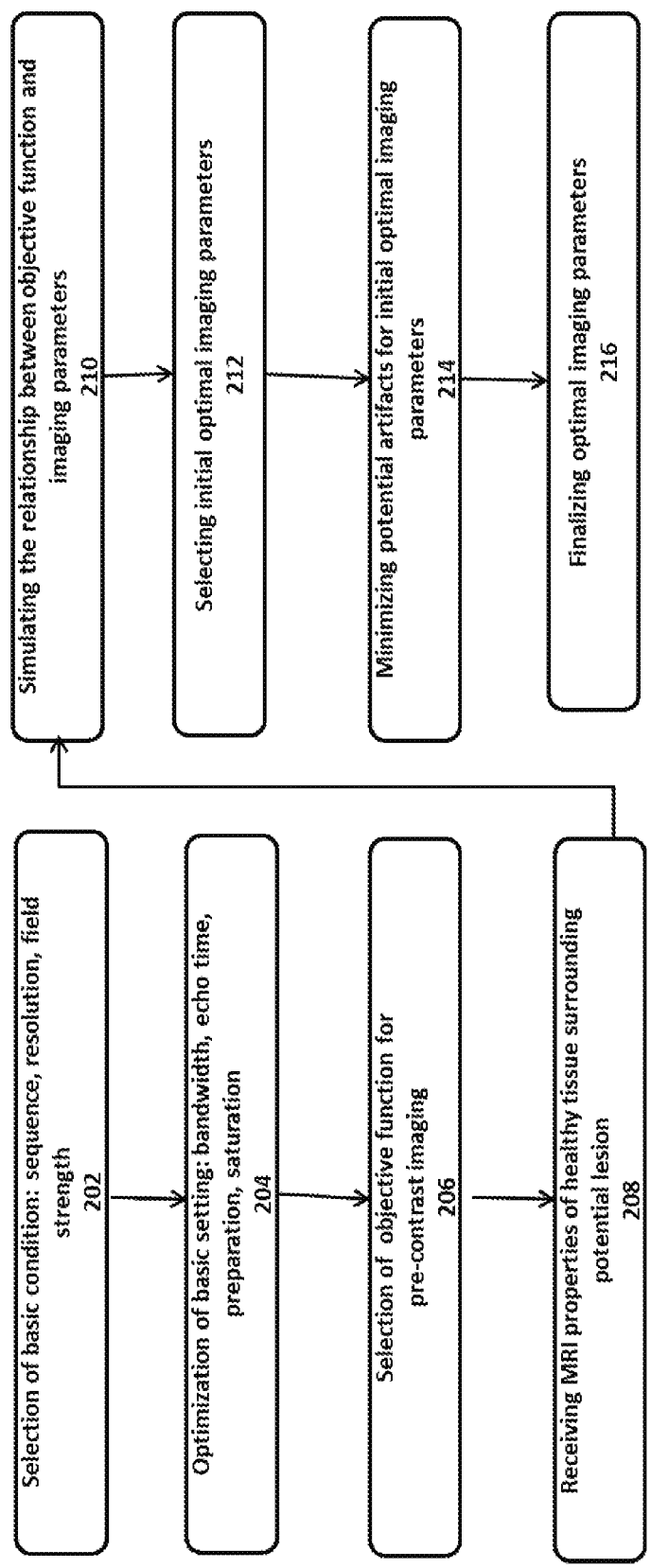
FIG. 2 is a flow chart illustrating example operations for optimizing imaging parameters of pre-contrast imaging according to one example of the present disclosure.

FIG. 2 shows a flow chart for optimizing imaging parameters of pre-contrast imaging according to one example in the present disclosure. The optimization can include the following steps: (a) Selection of basic conditions, e.g.: sequence, resolution, and field strength at 202; (b) Optimization of basic settings, e.g.: bandwidth, echo time, preparation, saturation at 204; (c) Selection of objective function for pre-contrast imaging at 206; (d) Receiving MRI properties of healthy tissue surrounding potential lesion at 208; (e) Simulating the relationship between objective function and imaging parameters at 210; (f) Selecting initial optimal imaging parameters at 212; (g) Minimizing potential artifacts for initial optimal imaging parameters at 214; (f) finalizing optimal imaging parameters at 216. As described herein, the imaging parameters can be selected by optimizing an objective function (e.g., an image quality metric, a lesion enhancement metric, a detection sensitivity metric) using an analytic solution, an EPG algorithm, a pseudo-steady-state algorithm, a windowed ramp function, or Bloch equations, for example. It should be understood that MRI properties of healthy tissue can be obtained by measurements and/or from literatures. For example, the MRI properties can optionally be stored in a memory of a computing device (e.g., computing device 1700 of FIG. 17B) and/or retrieved by a computing device (e.g., computing device 1700 of FIG. 17B) from a storage location over a network (e.g., the Internet).

Generally, high signal intensity and high resolution will better characterize structure and lesion in an image. High static field strength and high resolution is always expected. For example, SIEMENS 3T SKYRA scanner of SIEMENS AG of MUNICH, GERMANY that was equipped with a 32-channel head coil can be optimized for detecting brain tumor. 3D MPRAGE can be chosen for acquisition because 3D $T_1$-weighted images with high spatial resolution can minimize the partial volume effect and then improve the detection of small enhancing tumor tissue. The shortened acquisition train, optimal k-space strategies and bandwidth has excellent image quality of brain structure. Here partial slice Fourier acquisition of 6/8 is used to minimize acquisition train length for a given spatial resolution of 1 mm. Receive bandwidth of 140 Hz/pixel is minimized to reduce the noise. The echo space time $\tau$ of 8.9 ms is selected. Pre-contrast image is generally used as a reference to determine lesion enhancement for diagnosis and monitoring response-to-therapy. Additionally, pre-contrast image is also expected to improve the location of lesion throughout the comparison with post-contrast image. Good image contrast, particularly for tissue around lesion is very important for exact location of lesion. Therefore, contrast efficiency of GM-WM is selected for objective function for pre-contrast images.

Figure 3A:
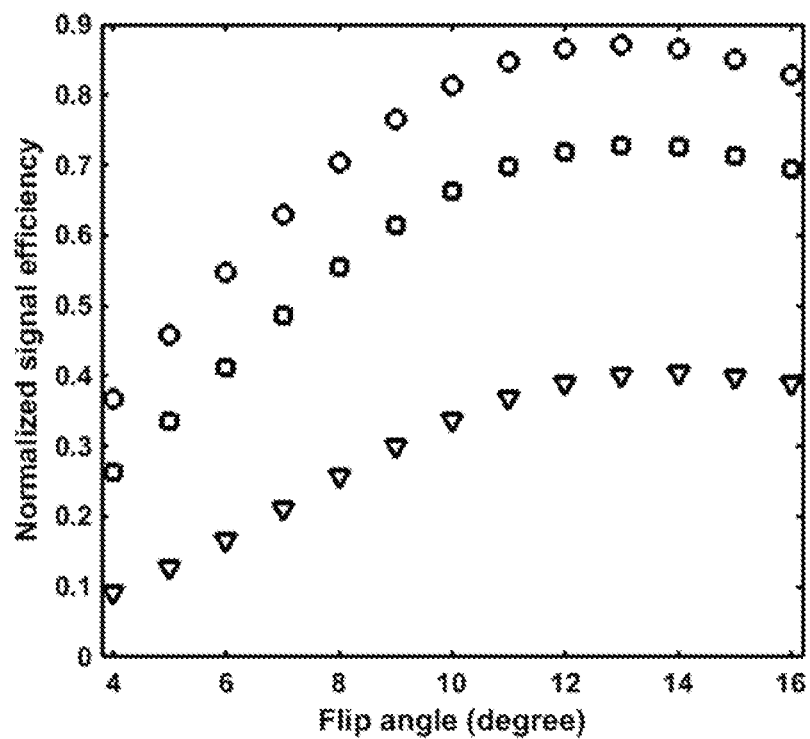
FIGS. 3A-3B illustrate relationships between simulated signal intensity efficiency (FIG. 3A) and WM-GM contrast efficiency (FIG. 3B) of healthy brain tissues (e.g., the gray matter (GM), white matter (WM), and cerebrospinal fluid (CSF)) and flip angle at an interval time between readout RF pulses of 8.9 ms before the administration of contrast agent.
Figure 3B:
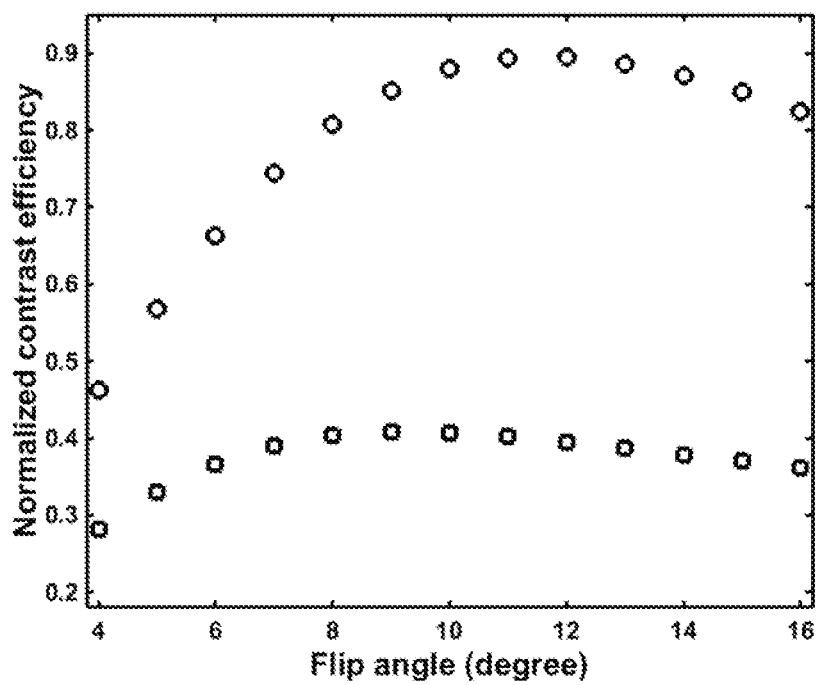

Effects of the major imaging parameters (e.g., flip angle, $\tau$, and TI,) on signal efficiency and contrast efficiency are simulated using Bloch's equation based on the values of $T_1$, $T_2$, and proton density of the gray matter (WM), white matter (WM) and cerebrospinal fluid (CSF) of the human brain, which at 3.0 T are 1300/900/3500 ms, 100/90/300 ms, and 0.75/0.65/1.0, respectively, without the administration of contrast agent. In vivo experiments confirmed that slice number N is chosen to be 176 in image domain for whole brain coverage at a slice thickness of 1 mm on the example scanner. Generally, 176 slice in image domain corresponding to 176 space line along slice direction. With the slice partial Fourier of 6/8 acquisition, the real acquisition k-space data is 132. Though the method for the shortened acquisition train is confirmed for non-contrast agent, it is applicable for contrast agent MRI. Thus, the simulated effects of flip angle on GM, WM and cerebrospinal fluid CSF signal intensities and GM-WM and GM-CSF contrast efficiencies at $\tau$=8.9 ms, effective TI of 750 ms, and total k-space line of 132 without the administration of contrast agent are shown in FIGS. 3A and 3B, respectively. Signal intensity and contrast efficiencies first increase and then decrease with increasing FA. Signal intensity reaches its maximum at the flip angle around 13° for the WM (represented by circles in FIG. 3A) and GM (represented by squares in FIG. 3A), and around 14° for the CSF (represented by triangles in FIG. 3A). After reaching their maximum values, signal intensities decline slightly with increasing flip angle. The GM-WM contrast efficiency (represented by circles in FIG. 3B) starts to approach their asymptotic values at the flip angle around 8°, reaching their maxima at the flip angle of around 12° and declining slightly at the flip angle from 12 to around 14°. The GM-WM contrast efficiency curve is almost flat when the flip angle increased from 10° to 13°. That is, variations of the flip angles would have a small impact on the GM-WM contrast efficiency when the flip angle is in the range from 9 to 14°. Similarly, GM-CSF contrast efficiency (represented by squares in FIG. 3B) starts to approach their asymptotic values at the flip angle around 8°, reaching their maxima at the flip angle of around 9° and declining slightly at the flip angle from 9° to around 14°. The GM-CSF contrast efficiency curve is almost flat when the flip angle increased from 7° to 13°. That is, variations of the flip angles would have a small impact on the GM-WM contrast efficiency when the flip angle is in the range from 7° to 13°. The signal intensities and contrast efficiencies reach their maximum values at different flip angles. Since maximizing contrast efficiency is more important than maximizing signal efficiency for diagnosis and tissue segmentation, the optimal flip angle is selected to be 12°. With this flip angle, GM-WM contrast efficiency achieves maximal values and is insensitive to non-uniform flip angle in different regions of the brain or across brains.

Figure 4:
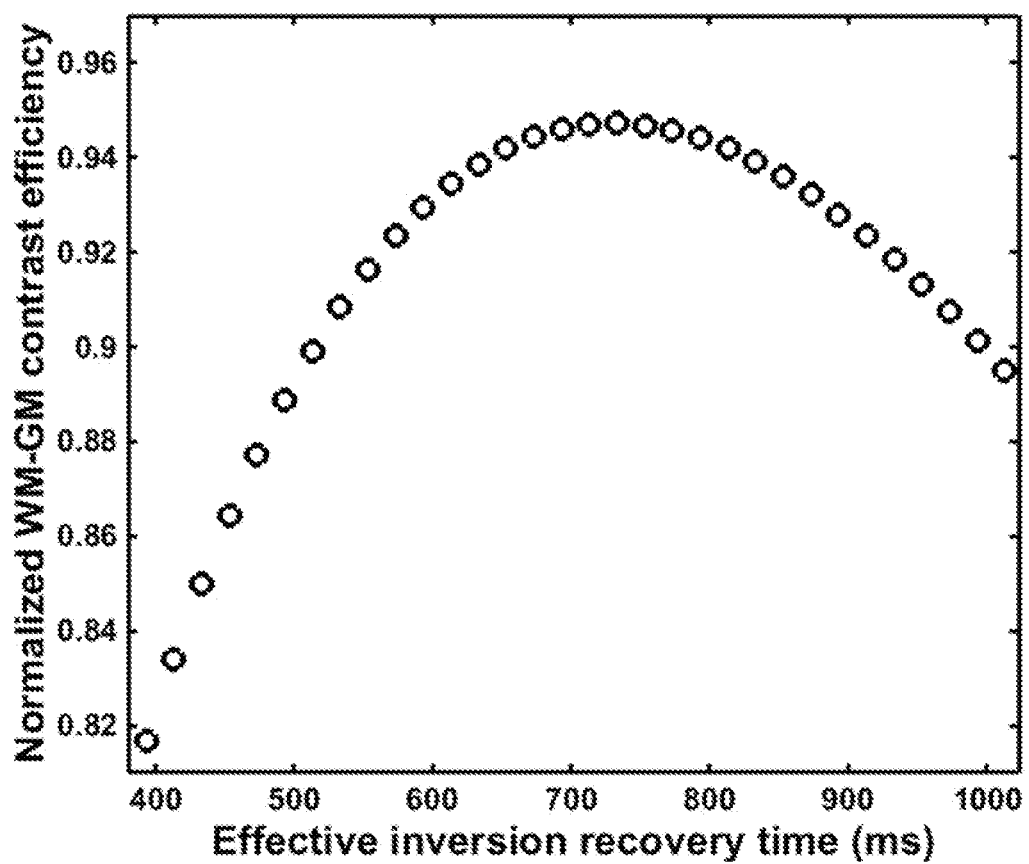
FIG. 4 illustrates simulated contrast efficiency between the GM and WM as functions of inversion recovery time (TI) at an interval time between readout RF pulses of 8.9 ms and flip angle of 12° before the administration of contrast agent.
Figure 10A:
FIGS. 10A-10B illustrate in vivo brain images acquired using the MP-RAGE sequence with different imaging parameters: optimized parameters for pre-contrast image (FIG. 10A) and post-contrast image (FIG. 10B) before the administration of contrast agent.

Due to limited options in the product MP-RAGE sequence, the continuous changes in total k-space acquisition are not available for the scanner. With regard to a nominal total slice number of 176 in image domain, total number of k-space acquisition with slice partial Fourier of off, 7/8, and 6/8 are 176, 156, and 132 respectively. The simulated GM-WM contrast efficiency vs effective TI curve are shown in FIG. 4. The maximal GM-WM contrast efficiency can be reached at the effective TI of 740 ms. But the GM-WM contrast efficiency changes less than 5% at TI changing from 550 ms to 1000 ms. Thus, the initial optimal parameters of adult brain imaging without the administration of contrast agent are flip angle of 12°, the effective TI of 740 ms, slice partial Fourier of 6/8, and total slice number of 176. In brain, fat-saturation is not important issue since little fat exists around GM and WM. But fat-saturation becomes very important issue in spine imaging. It is well known that susceptibility difference between air and brain strongly generates signal loss and geometry distortion in brain echo planar imaging. But with regards to MPRAGE sequence, susceptibility artifacts are very small and can be ignorable because TE is much less than $T_2^*$ of brain tissue around 50 ms at 3.0 T. The final optimal parameters of adult brain imaging without the administration of contrast agent are flip angle of 12°, the effective TI of 740 ms, slice partial Fourier of 6/8, total slice number of 176, and TE<10 ms. The brain image acquired with the final optimal pre-contrast imaging parameters are shown in FIG. 10A.

b). Optimization of Imaging Parameters for Post-Contrast

Figure 5:
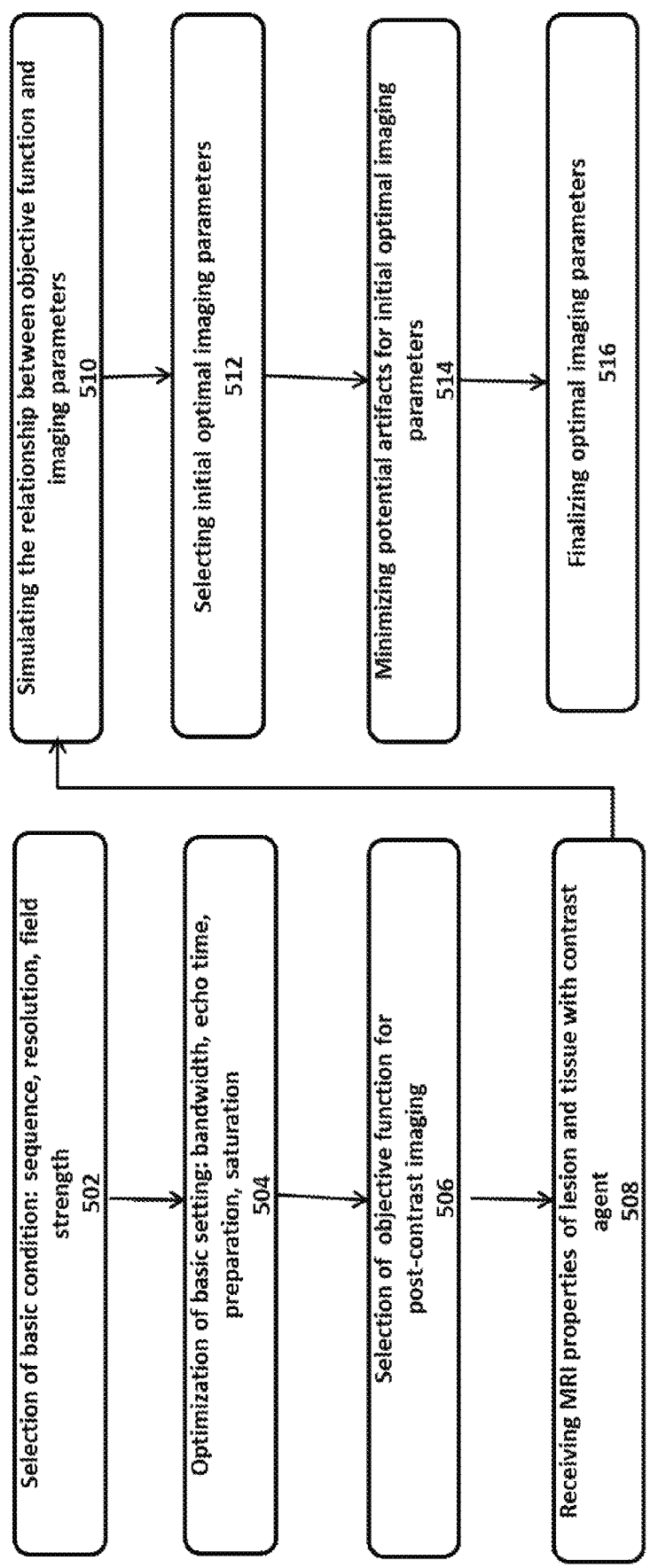
FIG. 5 is a flow chart illustrating example operations for optimizing imaging parameters of post-contrast imaging according to one example of the present disclosure.

Similarly to FIG. 2 for pre-contrast imaging, FIG. 5 shows a flow chart for optimizing imaging parameters of post-contrast imaging. The optimization can include the following steps: (a) Selection of basic conditions, e.g.: sequence, resolution, and field strength at 502; (b) Optimization of basic settings, e.g.: bandwidth, echo time, preparation, saturation at 504; (c) Selection of objective function for post-contrast imaging at 506; (d) Receiving MRI properties of healthy tissue surrounding potential lesion at 508; (e) Simulating the relationship between objective function and imaging parameters at 510; (f) Selecting initial optimal imaging parameters at 512; (g) Minimizing potential artifacts for initial optimal imaging parameters at 514; and (f) finalizing optimal imaging parameters at 516. As described herein, the imaging parameters can be selected by optimizing an objective function (e.g., an image quality metric, a lesion enhancement metric, a detection sensitivity metric) using an analytic solution, an EPG algorithm, a pseudo-steady-state algorithm, a windowed ramp function, or Bloch equations, for example. It should be understood that MRI properties of healthy tissue can be obtained by measurements and/or from literatures. For example, the MRI properties can optionally be stored in a memory of a computing device (e.g., computing device 1700 of FIG. 17B) and/or retrieved by a computing device (e.g., computing device 1700 of FIG. 17B) from a storage location over a network (e.g., the Internet).

Figure 6A:
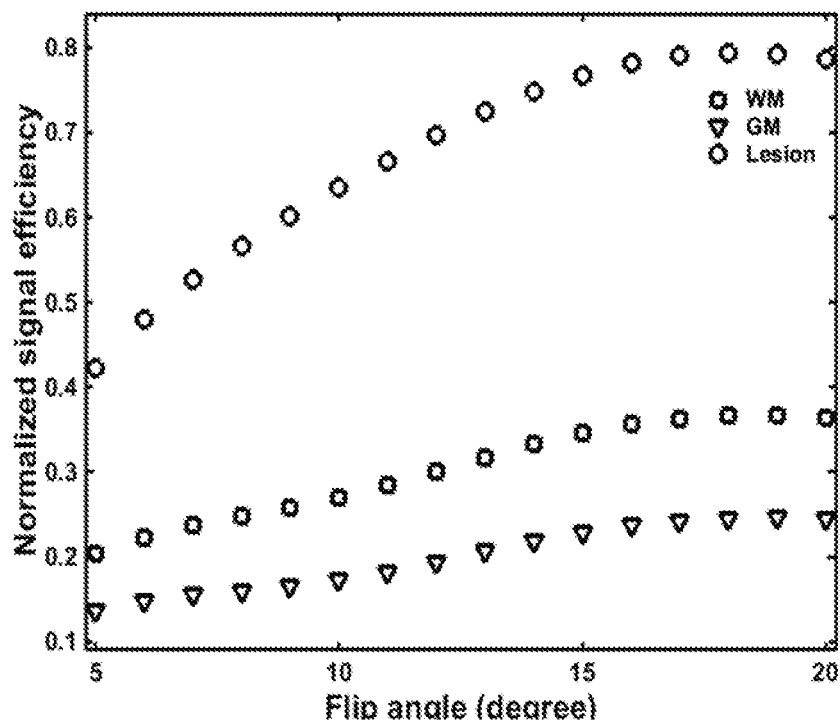
FIGS. 6A-6B illustrate relationships between simulated signal intensity efficiency (FIG. 6A) and WM-GM contrast efficiency (FIG. 6B) of brain tissues (lesion, GM and WM) and flip angle at an interval time between readout RF pulses of 8.9 ms after the administration of contrast agent.
Figure 6B:
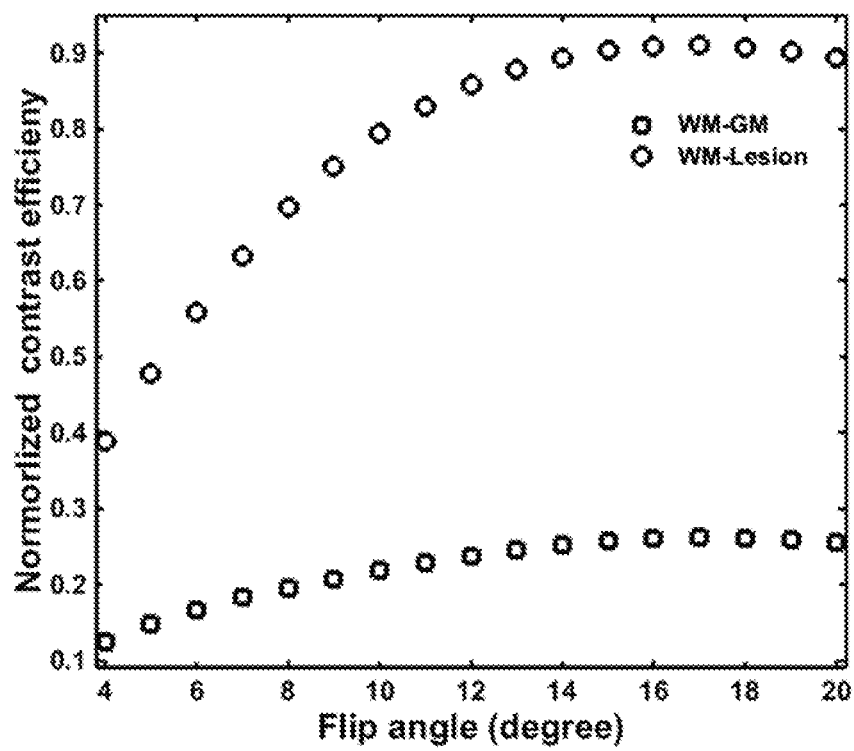
Figure 7:
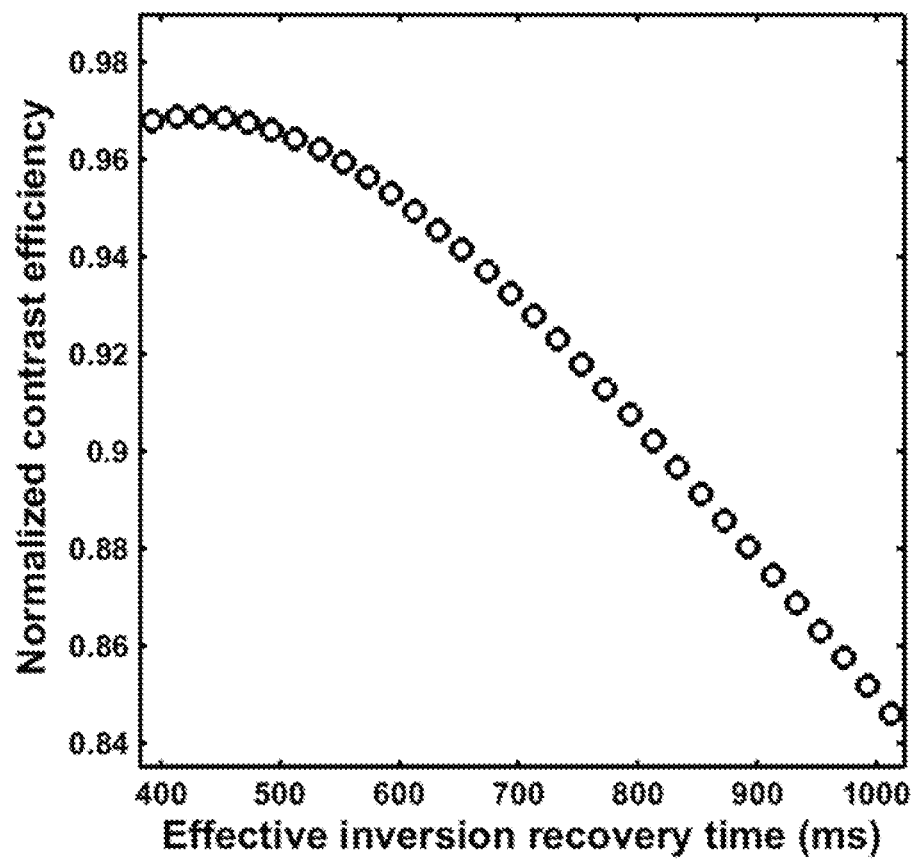
FIG. 7 illustrates simulated lesion-WM and GM-WM contrast efficiencies as functions of TI at an interval time between readout RF pulses of 8.9 ms and flip angle of 19° after the administration of contrast agent.

Generally, most post-contrast image has identical imaging condition to pre-contrast image, including resolution, field strength, sequence, even imaging parameters. In this case, the imaging condition is difficult to optimize for both pre-contrast image and post-contrast imaging. In present disclosure, all imaging condition can be changed to maximize the detection sensitivity of lesion, excluding the scanner or field strength. To simplify the problem, the MPRAGE sequence is still selected for acquiring post-contrast image. Additionally, the shortened acquisition train, optimal k-space strategies and bandwidth has excellent image quality of brain structure for MPRAGE sequence [Wang J et al. U.S. Pat. No. 9,339,239 B2; Wang J et al. WO 2016/145355 A1]. Partial slice Fourier acquisition, receive bandwidth and τ are selected to be identical to these for pre-contrast image. Post-contrast image is to determine lesion enhancement for diagnosis and monitoring response-to-therapy. Therefore lesion enhancement (EL) become an important metric and is selected for objective function of optimizing imaging parameters for post-contrast image. After the administration of contrast agent, $T_1$ contrast agent, such as Gd-based contrast agent, will leak into brain tissue and strongly reduces the $T_1$ relaxation. The reduced $T_1$ relaxation is dependent on static field strength, contrast agent concentration, and lesion tissue. The $T_1$ relaxation of lesion tissue can be reduced to less than 500 ms, even to 200 ms. In order to optimize the imaging parameters, an averaged relaxation time of 400 ms is selected in the simulation. While effects of the major imaging parameters (flip angle, τ, and TI) on WM-lesion contrast efficiency and/or lesion enhancement were simulated using Bloch's equation based on the values of $T_1$, $T_2$, and proton density of the WM, GM and lesion of the human brain, which at 3.0 T are 1300/900/400 ms, 100/90/200 ms, and 0.75/0.65/1.0, respectively, with the administration of contrast agent. The simulated effects of flip angle on GM, WM and lesion signal intensities and GM-WM and WM-lesion contrast efficiencies at τ=8.9 ms, effective TI of 50 ms, total k-space line of 132 with the administration of contrast agent, are shown in FIGS. 6A and 6B, respectively. Normalized signal intensity and contrast efficiencies first increase to maximum value and then decrease with increasing flip angles. Normalized signal intensity efficiencies reach their maximum at the flip angle around 19° for the WM and GM, and around 18° for enhanced lesion, respectively. Normalized contrast efficiencies reach their maximal value at the flip angle of 17° for WM-Lesion and 16° for GM-WM, respectively. The simulated contrast agent lesion enhancement efficiency vs effective TI curve are shown in FIG. 7. The maximal lesion enhancement efficiency can be reached at the effective TI of 450 ms, and then reduce with the increasing TI. But the lesion enhancement efficiency reduces about 10% at TI changing from 450 ms to 900 ms. Thus, the initial optimal parameters of adult brain imaging after the administration of contrast agent are flip angle of 17°, the effective TI of 450 ms, slice partial Fourier of 6/8, and total slice number of 176.

In order to simultaneously maximize image efficiency and efficacy before and after the administration of contrast agent, pre-contrast and post-contrast images can be acquired with different imaging parameters as shown in FIGS. 6A-6B. In other words, in the present disclosure, the pre-contrast and post-contrast images can optionally be acquired with different optimal imaging parameters. And then, the lesion can be extracted from post-contrast image and combined with pre-contrast image to form a combined image, which has excellent structural information of the tissues around lesion from pre-contrast image and lesion information from post-contrast image. This is as opposed to current clinical applications, where the imaging parameters for pre-contrast and post-contrast images are identical so that the lesion enhancement or lesion enhancement efficiency can be easy to estimate. In the present disclosure, the different protocols and imaging parameters can be optimized to acquire pre-contrast and post-contrast images. For example, the imaging parameters can be traded off according to FIGS. 6A-6B. The optimized imaging parameters should be around flip angle of 16° and effective TI of 550 ms. The use of these parameters is expected to balance lesion detection and structural information.

3. Optimization of Acquisition Timing

Despite contrast agent MRI having been widely used in clinical practice, there is little consensus regarding acquisition timing of protocol [Lee V S et al. Radiology 1999; 211: 69-77; Maravilla K R et al. Radiology. 2006; 240(2):389-400; Schmidt M A et al. Radiology. 2008; 249(1):178-186; Weng J C et al. Journal of Magnetic Resonance Imaging. 2010; 31(6):1323-1330; Maki J H et al. Journal of Magnetic Resonance Imaging. 2016; 43(1):249-260.]. Most discussions focus on the acquisition timing in MR angiographic examinations [Gross P et al. U.S. 20130274589 A1; Liu K et al. U.S. Pat. No. 6,505,064 B1]. The ideal scan timing for contrast agent MRI allows for maximal contrast concentration in region of interests (ROIs) and/or lesions. However, the contrast concentration in ROIs strongly depend on contrast agent characteristics, infusion rate, administered contrast concentration, administered method (oral or intravenous injection), transmit time of contrast agent, and ROI characteristics. Optimal acquisition timing will improve the detection and delineation of lesion [Kushnirsky M et al. Journal of neurosurgery. 2016; 124(2):489-495.] to avoid two situations which strongly lead to low contrast agent concentration in the ROIs and affect the performance of contrast agent MRI: (1) few contrast agent reaches ROI; (2) most contrast agent has cleared or washed out.

Figure 8:
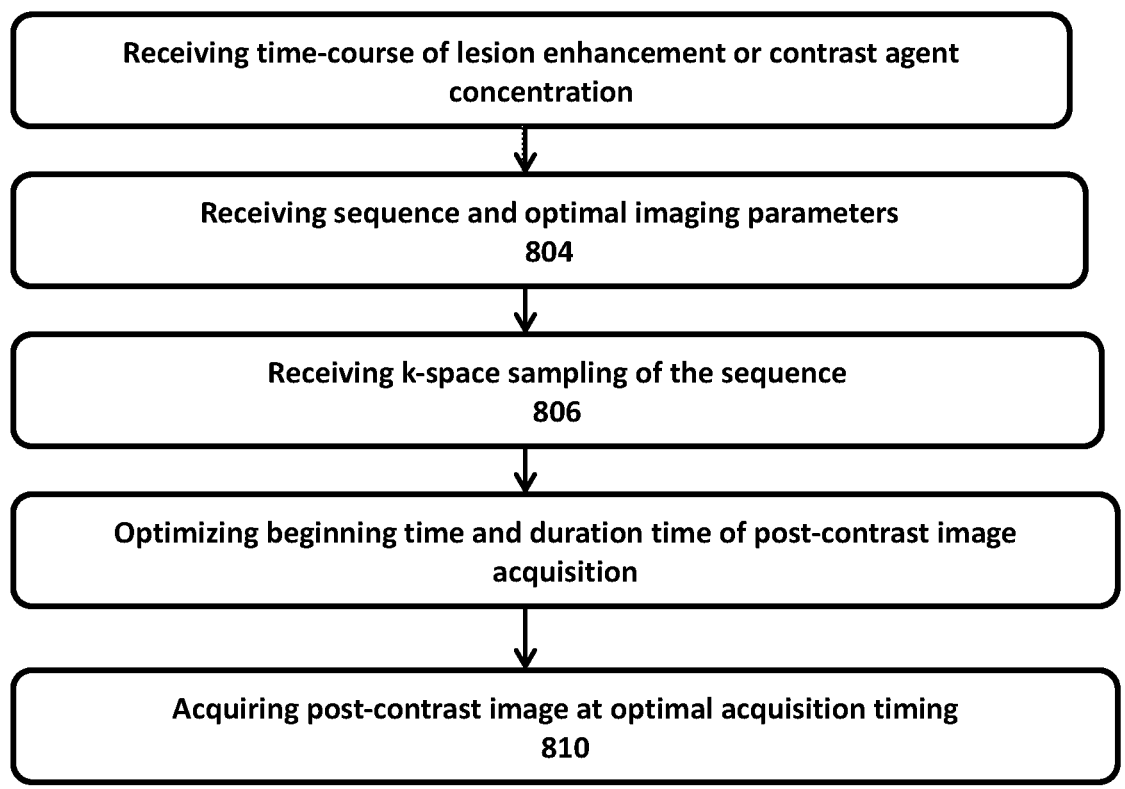
FIG. 8 is a flow chart illustrating example operations for acquisition timing optimization of post-contrast imaging according to one example of the present disclosure.
Figure 9:
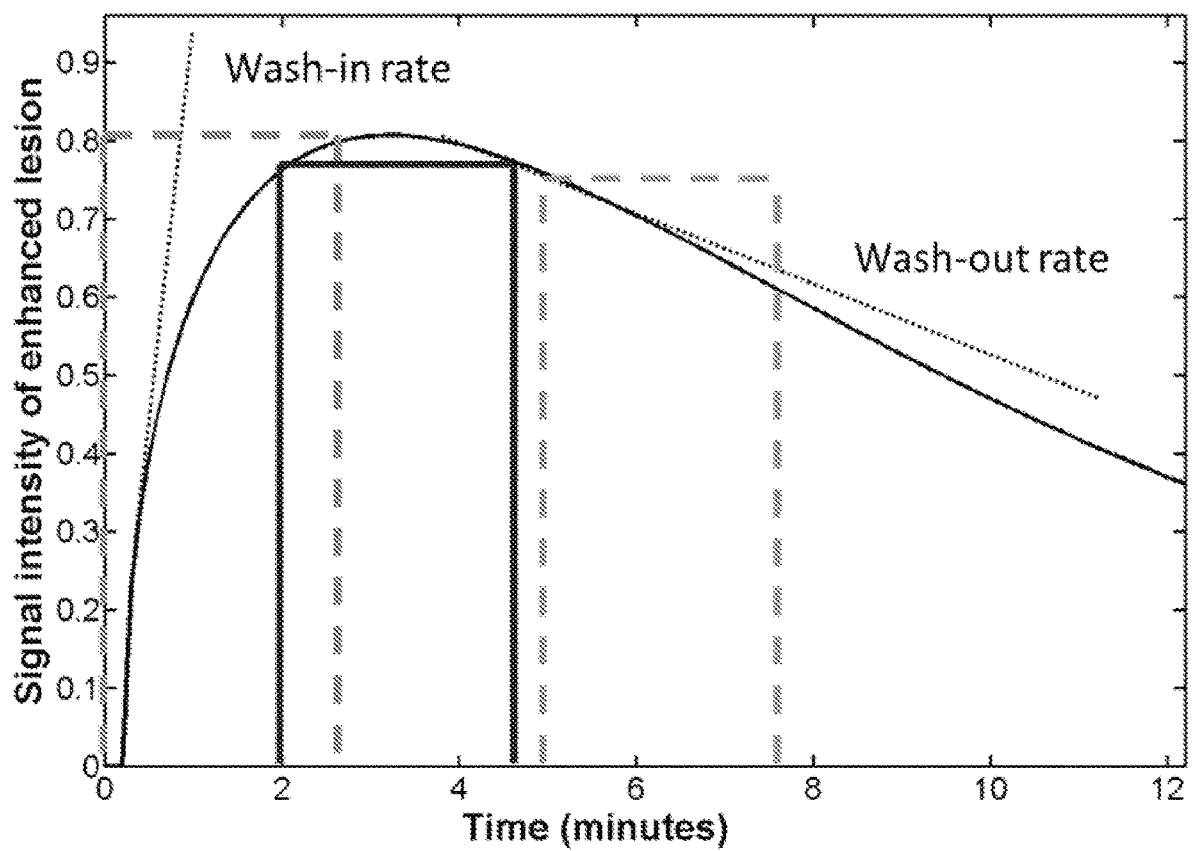
FIG. 9 is a time course of normalized signal intensity of enhanced lesion after the administration of contrast agent.

FIG. 8 is a flow chart for acquisition timing optimization of post-contrast image acquisition time in one example described in the present disclosure. The optimization can include the following steps: (a) receiving time-course of lesion enhancement or contrast agent concentration at 802; (b) receiving imaging or MRI sequence and optimal imaging parameters for post-contrast imaging at 804; (c) receiving k-space sampling of the sequence at 806; (d) optimizing beginning time and duration time of post-contrast image acquisition at 808; (e) acquiring post-contrast image with optimal acquisition timing at 810. It should be understood that k-space sample of the MRI sequence can be obtained by measurements and/or from literatures. For example, the k-space sampling of the MRI sequence can optionally be stored in a memory of a computing device (e.g., computing device 1700 of FIG. 17B) and/or retrieved by a computing device (e.g., computing device 1700 of FIG. 17B) from a storage location over a network (e.g., the Internet). The time course of signal intensity or contrast agent concentration in lesion can be estimated by various imaging techniques or obtained from literatures. The various techniques include ultrasound [Gross P et al. U.S. 20130274589 A1], dynamic contrast enhanced MRI, positron emission tomography ("PET"), computed tomography ("CT"), or dynamic susceptibility contrast MRI. In present disclosure, the focus is on the technique used to optimize the acquisition time after known the time course of contrast agent. While the disclosure [Gross P et al. U.S. 20130274589 A1] focuses on the method which ultrasound is used to determine timing of contrast agent inflow and/or outflow. Moreover, dynamic contrast-enhanced MRI can also provide the time-course of contrast agent concentration (or signal intensity). For example, a number of dynamic contrast-enhanced MRI in brain tumor show time course of enhanced tumor signal intensity as FIG. 9: the maximal signal intensity of enhanced tumor occurs 3 minutes after the administration of Gd-based contrast agent. Since peak of enhanced tumor signal intensity is not flat or smooth, the shortest image acquisition is expected to achieve maximal lesion enhancement and improve the detection as well as delineation of tumor for a given spatial resolution. For example, optimized 3D MPRAGE for post-contrast is selected. The total scan time for the optimized MPRAGE is around 2 minutes 30 seconds. According to the time-course in FIG. 9, the interval (the delayed time) between intravenous administration and the start of the post-contrast $T_1$-weighted image acquisition was carefully timed to achieve the best performance of contrast agent MRI. Without any delay time, the post-contrast image is acquired immediately after the administration of contrast agent. That is, the acquisition window is covered by left most dash line in FIG. 9. Additionally, with the delay time of 5 minutes [Maravilla K R et al. Radiology. 2006; 240(2): 389-400], the acquisition is covered by right most dash line in FIG. 9. At these acquisition timings, the acquisition has the following disadvantages which affect the detection sensitivity of lesion: (1) data acquisition at the k-space center does not coincide with the peak signal intensity within ROIs; (2) Similar to 2D $T_2$-weighted FSE with long train length, signal intensities in whole k-space have a very big dynamic range. It is very difficult to achieve that k-space data of both high and low spatial frequencies k-space data have identical signal intensity. It has to balance imaging parameters for high contrast (low spatial frequency) and burring artifacts (high spatial frequency). The optimal acquisition is covered by solid line and the delay time should be 2 minutes in FIG. 9. At this acquisition timing, k-space center can be selected to be acquisition center at around 3 minutes. Data acquisition at the k-space center coincides with the peak signal intensity within the ROIs. Additionally, signal intensity of ROIs is very smooth during whole acquisition. There is not burring artifacts in post-contrast image. Therefore, optimal acquisition time is the delay time of 2 minutes.

With regard to 2D and 3D $T_1$-weighted FSE, data acquisition at the k-space center is expected to coincide with the peak signal intensity or the peak contrast agent concentration within the ROIs. Generally, the k-space center is determined by effective TE, and does not match the peak contrast agent concentration. In application, the k-space sampling of conventional 2D and 3D $T_1$-weighted FSE with a constant refocusing flip angle can be adjusted to the time-course of signal intensity for post-contrast image acquisition. That is, the k-space line with the shortest effective TE should be in the center of k-space which coincides with the peak signal intensity or the peak contrast agent concentration within the ROIs. Similarly, the k-space sampling in 2D and 3D $T_1$-weighted FSE with variable flip angles can also be adjusted to the time-course of signal intensity for post-contrast image acquisition. That is, the k-space line with the largest refocusing flip angle and the shortest effective TE should be in the center of k-space which coincides with the peak signal intensity or the peak contrast agent concentration within the ROIs, and the other k-space lines with the larger refocusing flip angles should correspond to low spatial frequencies k-space date.

4. In Vivo Experiments

Figure 10B:
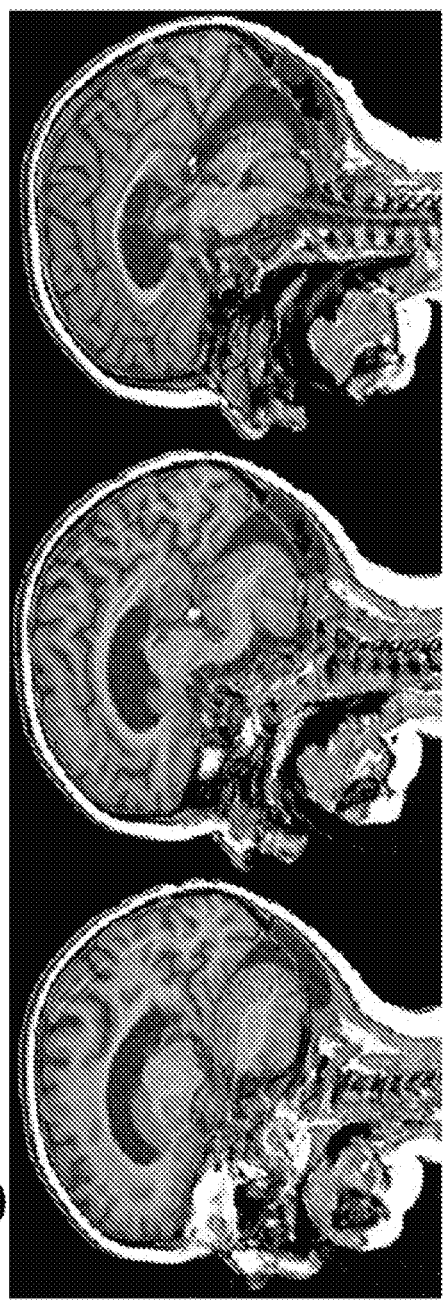

FIGS. 10A-10B show in vivo brain images acquired with MPRAGE sequence at optimal imaging parameters for pre-contrast image (FIG. 10A) and for post-contrast image (FIG. 10B) before the administration of gadobutrol (e.g., Gadavist of Bayer AG, Leverkusen, Germany). As discussed above, gadobutrol or Gadavist is an example contrast agent used in the examples herein. This disclosure contemplates the techniques described herein can be used with other contrast agents. Visually, image quality of brain image acquired with optimal imaging parameters for pre-contrast image is much higher than that with optimal imaging parameters for post-contrast image. Though later one has a high global signal intensity, WM-GM contrast is much lower than former one. FIGS. 11A-11B show in vivo brain images acquired with MPRAGE sequence at optimal imaging parameters for pre-contrast image (FIG. 11A) and for post-contrast image (FIG. 11B) after the administration of Gadavist. The size of enhanced lesion appears larger in the images acquired using optimal imaging parameters for post-contrast image (FIG. 11B) than those acquired using optimal imaging parameters for pre-contrast image (FIG. 11A). Further quantitative analysis indicates that the size of detected enhanced tumor using optimal imaging parameters for post-contrast image is 4% more than that using optimal imaging parameters for pre-contrast image. That is, the protocol could detect smaller and bigger enhanced lesion and showed high detection sensitivity for tumor lesion. In addition, lesion enhancement produced by optimal imaging parameters for post-contrast image was 326% which was comparable to that of 328% produced by optimal imaging parameters for pre-contrast image.

5. Image Combination

Example objectives of image combination or image fusion are to reduce the amount of data, to retain important information, and/or to create a new image that is more suitable for the purposes of human/machine perception or for further processing tasks. Various techniques for image fusion including intensity-hue-saturation (IHS) transform based fusion, principal component analysis based fusion, and multi scale transform based fusion, are known in the art. The multi scale transform based fusion comprises at least one of high-pass filtering method, pyramid method, wavelet transforms, and curvelet transforms.

In medical diagnostics and treatment, image fusion is the process of registering and overlaying multiple images of a patient into a single image [James A P et al. Information Fusion. 2014; 19:4-19; Sperling D S. U.S. Pat. No. 8,472,684]. The fused imaged (also referred to herein as a combined image) may be created from multiple images from the single or multiple imaging modalities and can be more informative than any of the input images alone. The to-be fused images typically serve different purposes, for example, in radiology and radiation oncology, CT images are used to ascertain differences in tissue density while MRI images are used to diagnose brain tumors. Similar strategies are applied in present disclosure. Unlike conventional procedure of applying same imaging protocol for acquiring both pre- and post-contrast images, in this disclosure, imaging or MRI protocols can be optimized for pre-contrast image to maximize tissue contrast and for post-contrast images to maximize tissue to lesion contrast, respectively.

In present clinical applications of contrast agent MRI, imaging parameters are optimized for maximizing the ability of detecting lesion after the administration of contrast agent, that is, the imaging parameters are optimized to maximize tissue-to-lesion contrast. But, these same imaging parameters are not typically optimal in the absence of the contrast agent, that is, these same imaging parameters are not typically optimal for use in acquiring pre-contrast agent images. Thus, according to conventional pre- and post-contrast imaging with the identical imaging parameters, it is difficult to achieve the two goals simultaneously. As a result, this greatly reduces the efficiency of both pre-contrast and post-contrast imaging in present clinical applications. Post-contrast imaging improves the detection sensitivity of lesion with penalty of worse structure using identical imaging parameters which are optimized for lesion detection. In practices, most pre- and post-contrast images are acquired by the identical imaging parameters which are not optimized for either pre-contrast image or post-contrast agent. The reason is because of the lack of exact understanding of both protocol and relaxation time before and after the administration of contrast agent.

Figure 12:
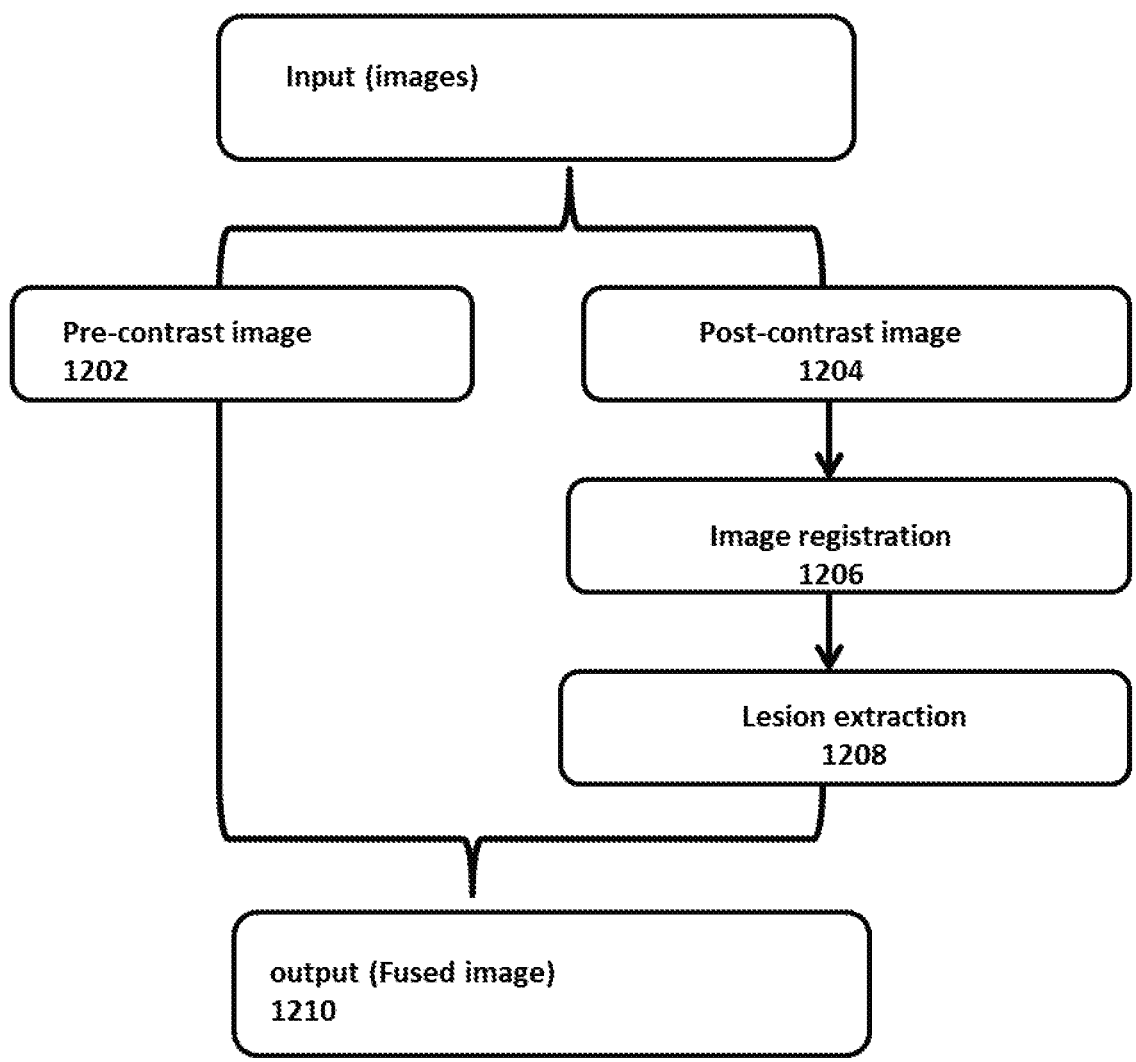
FIG. 12 is a flow chart illustrating example operations for image fusion according to one example of the present disclosure.
Figure 13:
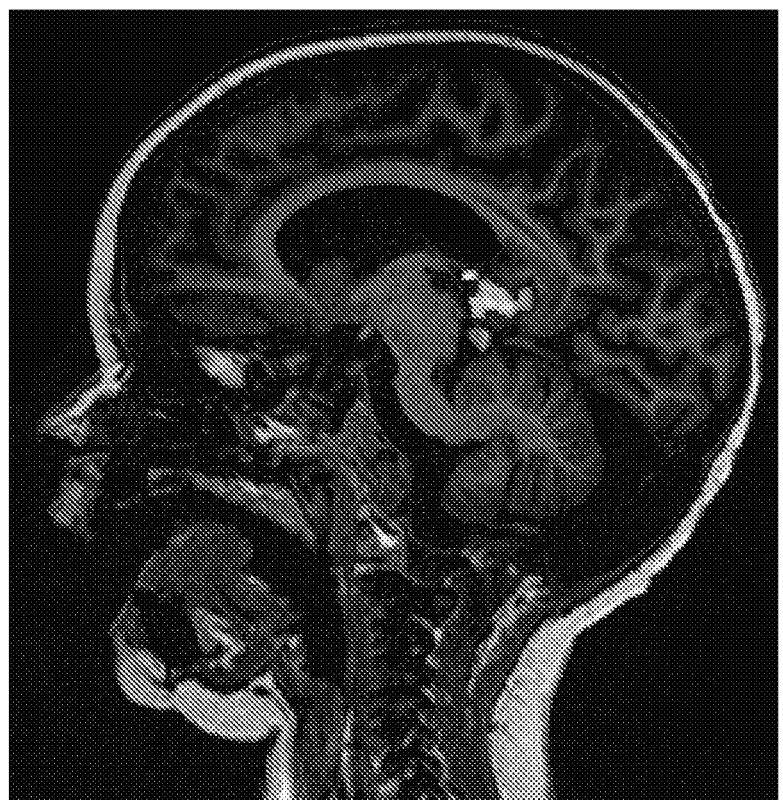
FIG. 13 is a fused image which is combined segmented brain tumor from FIG. 11B and FIG. 10A.

Therefore, image fusion can be used to combine structural and anatomical information from a pre-contrast image and lesion information from a post-contrast image into a single image to improve detection, localization and characterization of the lesion. The flow chart that shows image fusion according to one example of the present disclosure is shown in FIG. 12. The image fusion technique can include the following steps: (a) Receive a pre-contrast image at 1202; (b) Receive a post-contrast image at 1204 and Detect a lesion from post-contrast image; (c) register a pre-contrast image onto the post-contrast image at 1206; (d) Extract the lesion from the post-contrast image at 1208 and (e) overlay detected lesion onto the pre-contrast image to form a fused image at 1210. Various registration techniques known in the art are applicable for registering the pre-contrast and post-contrast images [Bond S et al. U.S. Pat. No. 8,818,057 B2; Oliveira F P et al. Computer methods in biomechanics and biomedical engineering. 2014; 17(2):73-93]. Pre-processing of images highly impacts the accuracy of the segmentation results and lesion detection. The pre-processing includes inhomogeneity signal correction, normalization of features, motion correction, etc. In post-contrast image, the lesion exhibits either hyper-signal or hypo-signals in $T_1$-weighted or $T_2$-weighted MRI with respect to normal tissue surrounding the lesions. Various segmentation methods, including histogram-based, edge detection, region-growing, level clustering, and level set methods, can be applied to detect the lesion [Pham D L et al. Annual review of biomedical engineering. 2000; 2(1):315-37; Setarehdan et al. Advanced algorithmic approaches to medical image segmentation: state-of-the-art applications in cardiology, neurology, mammography and pathology: Springer Science & Business Media; 2012].

It is noted that n conventional contrast-enhanced MRI, sequence for pre-contrast image is the same as that for post-contrast image. However, after the administration of contrast agent, the contrast agent may cross blood-brain barrier (BBB) and enter into the human tissue if the BBB is dysfunctional because of the concentration gradient and leaks through the vessel walls, eventually accumulating in the extravascular space. As a result, accumulated contrast agent in human tissue can shorten both longitudinal and transverse relaxation time apparently. MRI relaxation time of lesion and/or tissues is different before and after the administration of contrast agent, therefore, it may not be prudent to use the same imaging sequence for both pre-contrast and post-contrast image acquisitions. The sequence for pre-contrast image is expected to provide a reference image with the optimal description of spatial environment surrounding lesion. While the sequence for post-contrast image is expected to provide the optimal detection sensitivity of lesion in size, shape and morphometric. Moreover, unlike conventional approach, in the present disclosure, pre-contrast and post contrast images can be respectively acquired with their optimal imaging parameters. As a result, the contrast agent MRI efficiency can be maximized. Finally, the structural and spatial information from the optimized pre-contrast image with the lesion information from the optimized post-contrast image are combined to form a fused image which has a better visualization of the location, size and shape of lesion for diagnosis, disease staging, treatment planning, monitoring treatment and response-to-therapy.

6. Non-Lesion Enhancement and Artifacts Suppression

Figure 14:
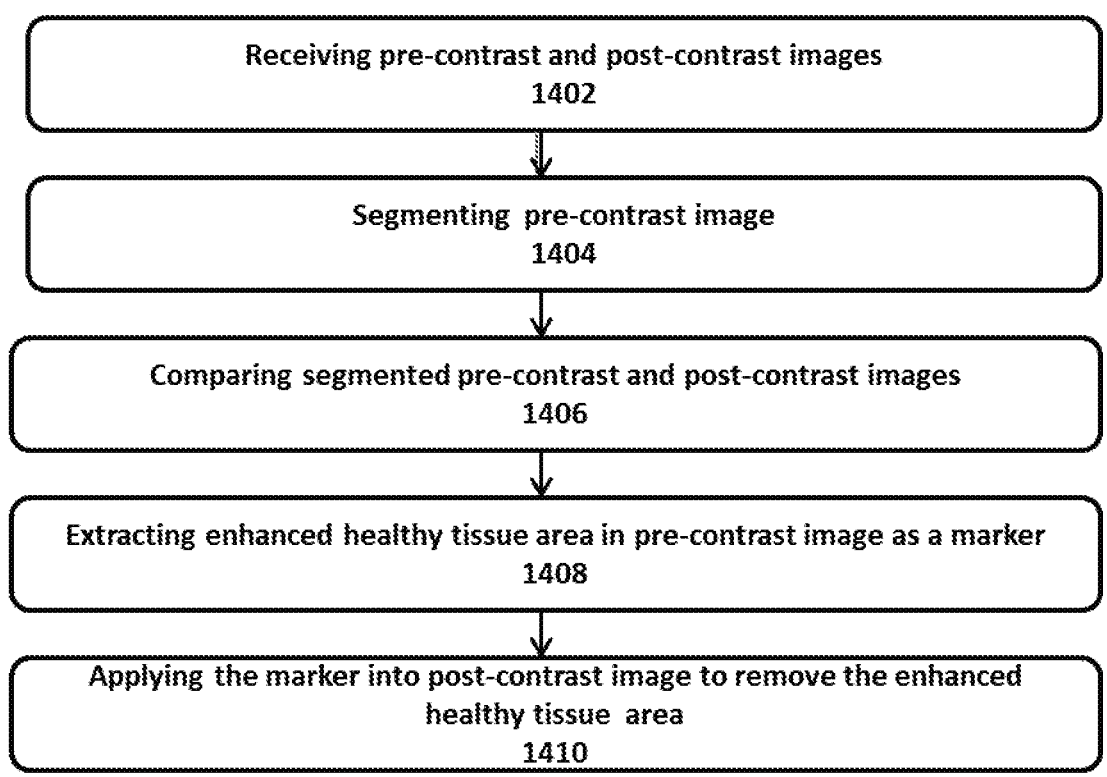
FIG. 14 is a flow chart illustrating example operations for suppression of non-lesion areas using post-processing method according to one example of the present disclosure.
Figure 15:
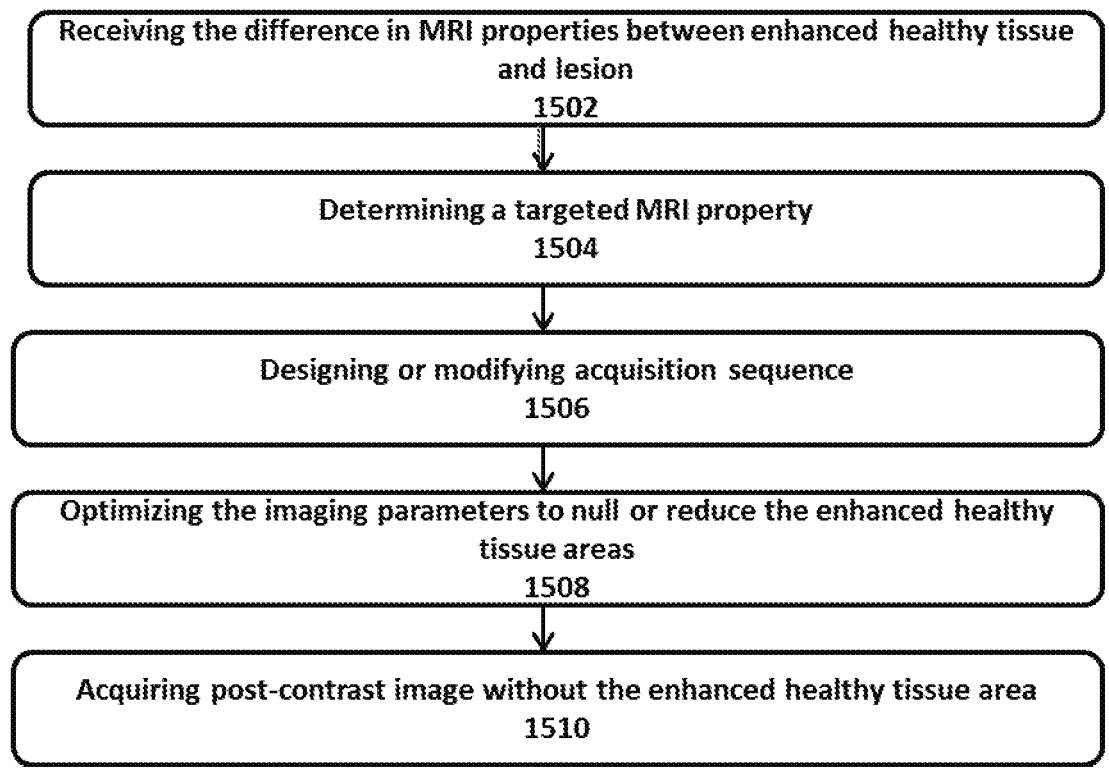
FIG. 15 is a flow chart illustrating example operations for modifying the imaging sequence to suppress leakage of the contrast agent in the non-lesion areas according to one example of the present disclosure.

It is important to suppress artifacts because some artifacts affect the quality of the MRI examination, while others do not affect the diagnostic quality but may be confused with pathology. Conventional MRI techniques include susceptibility artifacts, geometry distortion, signal inhomogeneity, cross excitation, cross-talk artifact, motion, chemical shift artifact, etc. Contrast agent MRI not only includes all artifacts mention above, but also includes artifacts which are caused by leakage of the contrast agent into a non-lesion area. For example, there exist contrast agent leakages in CSF and increase signal intensity of CSF after the administration of contrast agent in FIG. 11B. Present disclosure focuses on techniques to suppress or remove leakage of the contrast agent in the non-lesion area. The techniques include a post-process method (e.g., image processing) and an image acquisition method. FIG. 14 shows a flow chart for an example post-process method (e.g., imaging processing) to suppress leakage of the contrast agent in the non-lesion area. It should be understood that the post-process method can be used to remove leakage of the contrast agent in a non-lesion area. The procedure can include: (a) receiving pre-contrast and post-contrast images at 1402; (b) segmenting the pre-contrast image at 1404; (c) comparing the segmented pre-contrast image and post-contrast image to identify an enhanced non-lesion area at 1406; (d) extracting the segmented enhanced non-lesion area in pre-contrast image as a marker at 1408; and (e) applying the marker into post-contrast image at 1410. After applying the marker, it is possible to suppress or remove the enhanced non-lesion area from the post-contrast image. Because the enhanced non-lesion area is not related to the lesion, it can be suppressed or removed without affecting the diagnosis. Here pre-contrast and post-contrast images are able to be acquired with any (e.g., the same or different) sequence and/or imaging parameters. That is, both sequence and imaging parameters could be either optimal or non-optimal. Various segmentation methods, including thresholding method, clustering methods, histogram-based methods, edge detection, region-growing, can be applicable in the pre-processing of the pre-contrast image to obtain a segmented pre-contrast image [Pham D L et al. Annual review of biomedical engineering. 2000; 2(1):315-37; Setarehdan et al. Advanced algorithmic approaches to medical image segmentation: state-of-the-art applications in cardiology, neurology, mammography and pathology: Springer Science & Business Media; 2012]. Segmented pre-contrast and post-contrast images are compared to find the specific features or tissues which correspond to the non-lesion areas in post-contrast image. For example, part of CSF in FIG. 11B is enhanced and there does not exist tumor in CSF. Segmented CSF in pre-contrast image is used as a marker to remove enhanced CSF in post-contrast image. Of course, non-enhanced CSF in post-contrast image is also removed to improve detection sensitivity of the lesion tissue. Because CSF is not related to lesion, removed CSF cannot affect any diagnostic analysis. Alternatively or additionally, an image acquisition method can be used to suppress leakage of the contrast agent. The method can include optimizing the one or more imaging parameters to suppress leakage of the contrast agent in the non-lesion area according to the relaxation time difference in enhanced non-lesion tissue and enhanced lesion tissue after the administration of contrast agent. For example, inversion recovery pulse can be used to achieve this goal when their $T_1$ relaxation time is difference in enhanced non-lesion tissue and enhanced lesion tissue. Alternatively or additionally, the method can include optimizing the timing of image acquisition to suppress the leakage according to the difference of wash-in and wash-out time of the contrast agent in healthy tissue and the lesion tissue. The post-contrast image can be acquired before or after contrast agent enters into non-lesion areas. Alternatively or additionally, the method can include modifying the imaging sequence to suppress leakage of the contrast agent in the non-lesion area. FIG. 15 shows a flow chart for modifying the imaging sequence to suppress leakage of the contrast agent in the non-lesion area according to one example of the present disclosure. The procedure includes (a) Receiving the difference in MRI properties between enhanced non-lesion and lesion at 1502. MRI properties include at least one of $T_1$, $T_2$, diffusion coefficient, chemical shift, larmor frequency, and flow. The procedure also includes (b) determining a targeted MRI property which is easily used to differentiate enhanced non-lesion and lesion at 1504. For example, the diffusion coefficient of enhanced CSF in FIG. 11B is about three folder as much as that in tumor. The diffusion coefficient can be a good metric to differentiate enhanced non-lesion and lesion. In order to achieve this goal, the procedure can include (c) designing or modifying acquisition sequence at 1506. That is, a diffusion gradient should be added to the acquisition sequence to differentiate enhanced non-lesion and lesion. The procedure can also include (d) optimizing the imaging parameters to null the enhanced non-lesion areas at 1508. It should be understood that MRI properties between enhanced non-lesion and lesion tissue can be obtained by measurements and/or from literature. For example, the MRI properties can optionally be stored in a memory of a computing device (e.g., computing device 1700 of FIG. 17B) and/or retrieved by a computing device (e.g., computing device 1700 of FIG. 17B) from a storage location over a network (e.g., the Internet). The b-value is a factor that reflects the strength and timing of the gradients used to generate diffusion-weighted images. The higher the b-value, the stronger the diffusion effect. As a result, it is easy to differentiate enhanced CSF and tumor in FIG. 11B. But the high b-value also reduces the signal intensity of enhanced tumor. It is important to select the b-value to suppress enhanced non-lesion areas using diffusion sequence. Finally, the enhanced non-lesion areas can be reduced or removed with modification of image acquisition used to acquire the post-contrast image at 1510.

7. Optimization of Administered Contrast Agent Concentration

MRI contrast agent may make certain tissues, abnormalities, or diseases more clearly visible when it is administered by injection or orally in MRI examinations. When used in MRI, contrast agent expands the range of signal intensities detected during the examination and permits the detection of a wide variety of pathologic processes, including inflammation, infection, and malignancy, that would otherwise be undetectable with unenhanced MR imaging or other imaging modalities. MRI contrast agent comprises at least one of physiologically acceptable paramagnetic substance (Gd-chelates), superparamagnetic substance (such as superparamagnetic iron oxide), or ferromagnetic substance, which could be one of a magnetic small-molecule-based compound, a magnetic large-molecule-based compound, or a magnetic nanoparticle-based compound. Generally, MRI contrast agent is generally very safe and side effects or reactions are uncommon but may occur. Gadolinium-based MRI contrast agents are the most commonly used. To date, nine GBCAs have been commercialized and widely applied in the central nervous system, vasculature, and whole body. The safety issue of Gadolinium-based contrast agents in patients with end-stage renal disease was first proposed by Dr. T. Grobner in the early of 2006 [Grobner T. Nephrol Dial Transplant 2006; 21:1104-1108]. He found that correlation between administration of Gadolinium-containing agents and development of nephrogenic systemic fibrosis (NSF) a rare but potentially fatal disorder in patients with end-stage disease. And then the U.S. Food and Drug Administration (FDA) released a Public Health Advisory notification. The worldwide surveillance studies indicated extremely low incidence of adverse drug reactions to gadolinium contrast agents: (1) Immediate hypersensitivity reactions, such as allergies and asthma occur in approximately 0.1% cases. (2) Moderately severe hypersensitivity reactions, such as bronchospasm, facial edema, or widespread urticarial, occur in about 0.02% cases. (3) Worldwide, a number of severe reactions, including death, is about 2.5 in 1 million. Thus the gadolinum-based MR contrast agents are extremely safe. After being administered, Gadolinium-containing agents are mostly eliminated from the body through the kidneys. Although patients have traditionally been told that the contrast agent clears from body in 24 hours, small amounts of gadolinium possibly stay in the body long-term. However, recent papers have demonstrated that gadolinium accumulation with concomitant $T_1$ shortening have been observed in the brains of patients who have received multiple doses of gadolinium contrast [Kanda T et al. Radiology. 2014; 270: 834-841; Errante Y et al. Invest Radiol. 2014; 49: 685-690; McDonald R J et al. Radiology. 2015; 275: 772-782; Quattrocchi C C et al. Invest Radiol. 2015; 50: 470-472; Radbruch A et al. Radiology. 2015; 275: 783-791; Kanda T et al. Radiology. 2015; 275: 803-809; Adin M E et al. AJNR Am J Neuroradiol. 2015; 36: 1859-1865; Radbruch A et al. Radiology 2015; 275:783-791]. The magnitude of the effect is proportional to the cumulative lifetime dose administered and occurs without renal or hepatic dysfunction. Preliminary results indicate that the phenomenon is more common in linear agents with weaker chemical binding to free gadolinium than to macrocyclic agents with stronger binding. Visible changes on $T_1$-weighted images may be present after as few as 4 exposures. The reported incidence of NSF is decreasing, possibly attributable to a greater awareness of at-risk patients, lower dosing of contrast agents and the more widespread use of macrocyclic agents. Subsequent autopsy studies verified the accumulation of gadolinium in the enhanced brain structures [McDonald R J et al. Radiology. 2015; 275: 772-782; Adin M E et al. AJNR Am J Neuroradiol. 2015; 36: 1859-1865.]. Further findings suggest that intravenous administration of gadolinum-based MR contrast agent is associated with dose-dependent deposition in neuronal tissues that is unrelated to renal function, age, or interval between exposure and death. The clinical consequences of gadolinium crossing the blood-brain barrier and being deposited in neuronal tissues is not yet clear, and further investigation into the bio-distribution of gadolinium is warranted. Additionally, it is unknown whether these gadolinium deposits are harmful or can lead to adverse health effects. Therefore, The Food and Drug Administration suggested that doctors limit use of the contrast agents seeks to make sure the "additional information provided by the contrast is necessary." Additionally, Optimal contrast agent performance is of great importance and given the number of MRI contrast agent options today [Khan R. Topics in magnetic resonance imaging: TMRI. 2016; 25(4):157-161].

While contrast agent MRI can provide a lot of important diagnostic information, it's not perfect. Risks and benefits always have to be weighed. The higher the dose (including cumulative dose), the higher the risk. The higher the dose (including cumulative dose), the higher the severity side effect. Before the mechanisms of gadolinium sequestration, deposition, and nonuniform uptake in certain neuroanatomic locations remain fully understood, efforts have been made to reduce the contrast agent concentration for MRI examination, including optimization of imaging protocol, optimization of acquisition timing after administration of contrast agent, an application of a contrast agent with a higher relaxivity, and imaging acquisition with a higher tesla scanner. These techniques and methodologies can be used not only to lower the contrast agent concentration, but also to generate more signal at equivalent doses without the penalty of detection sensitivity, potentially lowering toxicity and/or improving detection or delineation of lesions.

Generally, $T_2$ or $T_2^*$ reduces with the decreasing $T_1$ for human tissue when contrast agent is injected. With the administration of $T_1$ contrast agent, some of lesion $T_1$ will decrease and its signal intensity for $T_1$-weighted image will be enhanced. Simultaneously, the contrast agent will lead to the reduction of signal intensity for $T_2$-weighted image or $T_2^*$ weighted image. Therefore, optimization of acquisition sequence and imaging parameters are very important for contrast agent MRI. This disclosure describes an optimization of echo time to reduce the effect from $T_2$ or $T_2^*$ on signal intensity. The technique described can be extended to other sequence and non-contrast agent MRI.

In the presence of the contrast agent, the observed longitudinal relaxation rate $R_{1,obs}$ originate with the contribution from an intrinsic tissue and the contrast agent, according to $$R_{1,obs} = R_{1,tissue} + R_{1,ca} \tag{15}$$

where $R_{1,tissue}$ is the intrinsic longitudinal relaxation rate of the tissue without the contrast agent, and $R_{1,ca}$ is longitudinal relaxation rate which is proportional to the concentration of the contrast agent:

$$\frac{1}{T_{1,obs}} = \frac{1}{T_{1,tissue}} + r_1 \cdot M \tag{16}$$

where $r_1$ is the longitudinal relaxivity (in $mM^{-1}s^{-1}$) and [CA] the concentration of the contrast agent. The contrast in the MR images can be enhanced either by using a contrast agent with a high relaxivity $r_1$ and/or by increasing the local contrast agent concentration. For example, $r_1$ for Gd-contrast agent is about 3.7-5 $mM^{-1}s^{-1}$ at 3.0 Tesla.

Similarly, the observed relaxation rate $R_{2,obs}*$ originate with the contribution from an intrinsic tissue and the contrast agent, according to $$R_{2,obs}* = R_{2,tissue}* + R_{2,ca}* \quad (17)$$

where $R_{2,tissue}*$ is the intrinsic transverse relaxation rate of the tissue without the contrast agent, and $R_{2,ca}*$ is transverse relaxation rate which is proportional to the concentration of the contrast agent:

$$\frac{1}{T_{2,obs}^*} = \frac{1}{T_{2,tissue}^*} + r_2 \cdot M \quad (18)$$

where $r_2$ is the transverse relaxivity (in $mM^{-1}s^{-1}$) and [CA] the concentration of the contrast agent. The contrast in the MR images can be enhanced either by using a contrast agent with a high relaxivity $r_2$ and/or by increasing the local contrast agent concentration. In present disclosure, the observed longitudinal and transverse relaxation times are applied in the computer simulation to optimize imaging parameters after the administration of contrast agent.

Figure 16:
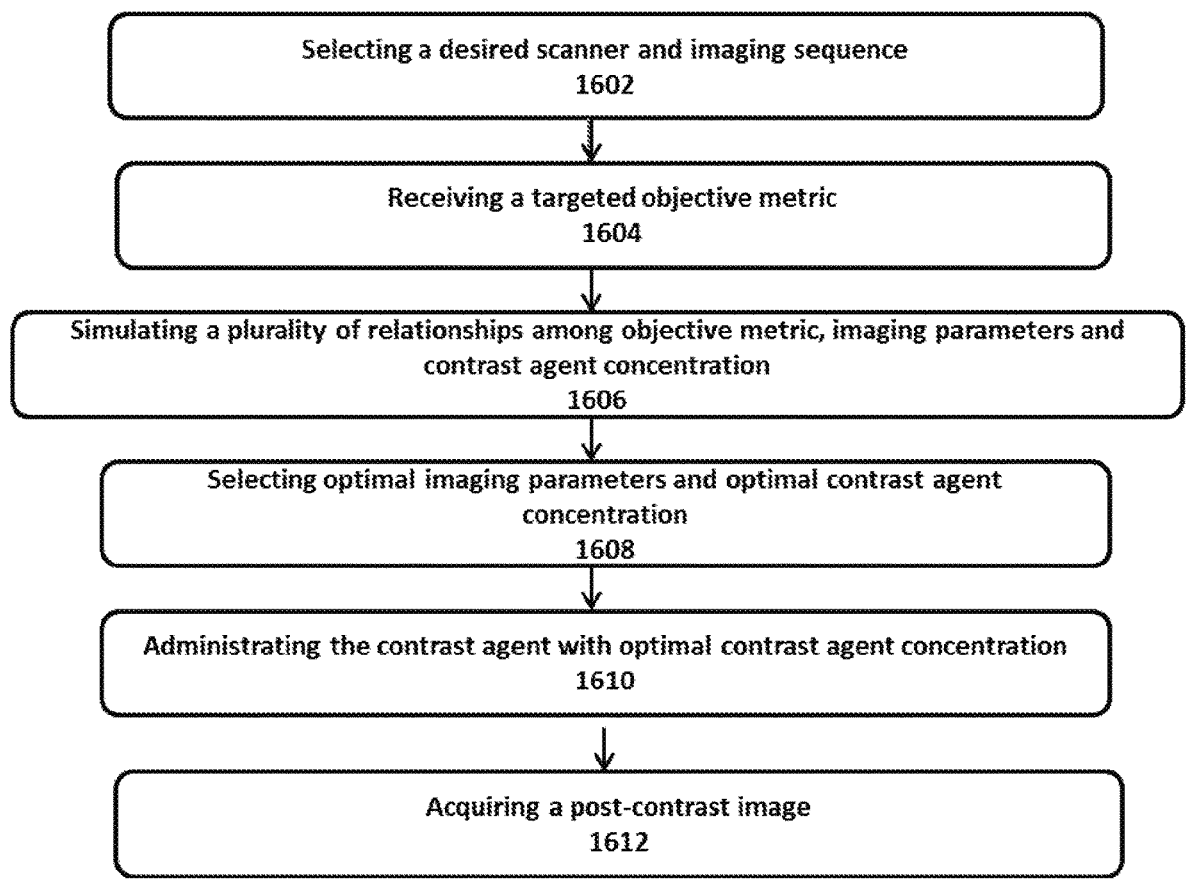
FIG. 16 is a flow chart illustrating example operations for optimizing contrast agent concentration according to one example of the present disclosure.

FIG. 16 shows a flow chart for optimizing contrast agent concentration. The optimization of contrast agent for repeated examination will include the following procedure: (a) selecting a desired scanner, user-selectable parameters and imaging sequence at 1602; (b) receiving a targeted objective metric or image quality metric at 1604; (c) simulating a plurality of relationships among an image quality metric, imaging parameters, and contrast agent concentration at 1606; (d) selecting optimal imaging parameters and optimal contrast agent concentration to optimize a lesion enhancement metric or a detection sensitivity metric after administration of contrast agent at 1608; (e) administrating the contrast agent with optimal contrast agent concentration at 1610; (f) acquiring a post-contrast image with optimal imaging parameters at 1612. It is known that the higher static fields lead to higher signal intensity and detection sensitivity. Thus, it is a desired scanner with higher static field strength because it has higher detection sensitivity after the administration of contrast agent with an identical concentration. A targeted objective metric (e.g., the image quality metric) is determined by a diagnostic method and/or physician (radiologist) requirements for the visualization of morphological/structural or pathological lesions, modifications and/or alterations of the lesion tissues. As discussed above, the targeted objective metric (e.g., the image quality metric) includes at least one of contrast, contrast-to-noise, contrast efficiency, or contrast-to-noise efficiency, lesion enhancement, lesion enhancement efficiency, and artifacts. Compared with the objective metric the preliminary contrast agent MRI examination, the targeted objective metric can be estimated. The most of selected imaging parameters should be at least one of sequence, resolution, bandwidth, echo space time, etc. Generally, the Bloch equation only includes image quality metric, the relaxation time, proton density, and imaging parameters. But the relaxation time after the administration of contrast agent is associated with a concentration of the contrast agent using the Eqs. 16 and 18. Therefore, the indirect relationship among image quality metric, contrast agent concentration and imaging parameters can be obtained. The image quality metric can be regarded as multivariate function of imaging parameters and contrast agent concentration.

Mathematic Procedure for Optimizing Concentration of Contrast Agent

The concentration of contrast agent is used as a single variable function of a targeted objective metric (e.g., the image quality metric) when all imaging parameters are determined by experience and previous optimization. The experience in imaging parameters for a given sequence for repeated examination results from preliminary examination. Additionally, the imaging parameters can also be determined using the solution of Bloch Equation which includes at least one of analytic solution, numerical solution and approximation solution. The targeted objective metric (e.g., the image quality metric) is determined by a diagnostic method and/or physician (radiologist) requirements for the visualization of morphological/structural or pathological lesions, modifications and/or alterations of the lesion tissues. The targeted image quality metric includes at least one of contrast, contrast-to-noise, contrast efficiency, or contrast-to-noise efficiency, lesion enhancement, lesion enhancement efficiency, and artifacts. The optimized concentration can be determined using extreme single variable function theorem.

Moreover, the concentration of contrast agent is also used as one of multiple variables [Reeder S B et al. Magn Reson Med. 2016; 75(4):1556-1564.], that is a targeted image quality metric is multivariate function of concentration of contrast agent, imaging parameters. Similarly, the targeted image quality metric is identical to that before where the concentration of contrast agent is also used as a single variable. And then the optimized concentration can be determined using local extreme multivariate function theorem. The optimal concentration of each contrast agent must be lower than its concentration that is permitted by government. For example, in the United States of America, standard dose (mmol/kg) for gadobutrol (Gadavist) of 0.1 was approved by the U.S. Food and Drug Administration (FDA).

Example MRI System

An example MRI system is described in U.S. Pat. No. 8,502,538 to Dannels et al., entitled "B1 and/or B0 mapping in MRI system using k-space spatial frequency domain filtering with complex pixel by pixel off-resonance phase in the B0 map," issued Aug. 6, 2013, the disclosure of which is hereby incorporated by reference in its entirety. The example MRI system is described below with reference to FIG. 17A. This disclosure contemplates that the techniques for detecting lesion tissue using contrast agent MRI and/or suppressing contrast agent leakage can optionally be implemented using the example MRI system. For example, the MRI system shown in FIG. 17A has a static magnetic field generating unit 12 and a gradient magnetic field generating unit 14 for generating respective magnetic fields in proximity to an object 18. The MRI system also includes a transmitting and receiving unit 16 for irradiating RF pulses to the object and receiving MR signals, a patient table on which the object 18 is placed, and a patient table moving system for moving the table in the body axis direction (e.g., z-axis direction) of the object. The MRI system can also include one or more computing devices such as the example computing device of FIG. 17B. A computing device can be operably coupled to the MRI system, for example, using by any medium that facilitates data exchange between the MRI system and the computing device including, but not limited to, wired, wireless and optical links. For example, a computing device can be configured to convert the MR signals received by the transmitting and receiving unit 16 into k-space data. A computing device can also be configured to generate MR image data from the k-space data by image reconstruction processing. Further, the MRI system can optionally include a workflow setting unit, an imaging operation determining unit, a display unit, an input unit, and a controller system.

The workflow setting unit sets a first workflow relating to the MRI examination by estimating an imaging time of each of the imaging methods in the performing order initially set by a scan plan. Further, the workflow setting unit sets a second workflow relating to the MRI examination by estimating a shortest performing order, by which an examination time necessary to sequentially perform a plurality of imaging methods constituting the imaging method group set by the input unit is minimized, an imaging time of each imaging method in the shortest performing order, and the like. The imaging operation determining unit determines whether an imaging operation during a main imaging according to the workflow. This disclosure contemplates that the workflow setting unit and/or the imaging operation unit can be implemented using hardware, software, and or a combination thereof. The display unit displays image data such as local image data, diagnosis image data using display, printer and other displayer. The input unit is manipulated by an operator to input signals to the MRI apparatus to set the imaging method group, the performing order, the imaging condition, and the like. The controller system is composed of a processor and integrally controls the respective units of the MRI system described above.

The static magnetic field generating unit 12 includes a main magnet to generate a strong static magnetic field in proximity to the object. The gradient magnetic field generating unit 14 includes gradient magnetic field coils for generating gradient magnetic fields in an x-axis direction, a y-axis direction, and a z-axis direction, which are orthogonal to each other. The transmitting and receiving unit 16 includes a transmission coil and a transmitter unit for irradiating the RF pulses to the object and a receiving coil and a receiver unit for receiving MR signals generated by the object. Optionally, a transceiver coil having the functions of both the transmission coil and the receiving coil can be used. The receiving coil may be composed of, for example, a so-called array coil in which, for example, a plurality of coil elements are disposed to detect the MR signals generated by the object.

The image reconstruction unit includes an MR signal storage unit, a signal processing unit, and an image data storage unit. The MR signal storage unit (e.g., memory) stores the MR signals, which are collected by the receiver unit of the transmitting and receiving unit 16. The signal processing unit has an image reconstruction processing unit and an image processing unit. The image reconstruction processing unit generates image data from the MR signal storage unit by image reconstruction processing, for example, performed by a Fourier transformation such as 2D FFT. When the MR signals to a three-dimensional region are collected, the image reconstruction processing unit of the signal processing unit generates volume data. Subsequently, the image processing unit generates three-dimensional image data such as volume rendering image data, surface rendering image data and the like or two-dimensional image data, multi planar reconstruction image data, and the like, because predetermined image processing is performed for the volume data generated by the image reconstruction processing unit. Then, the image data described above obtained by the signal processing unit are stored to the respective storage regions of the image data storage unit.

Example Computing Device

It should be appreciated that the logical operations described herein with respect to the various figures may be implemented (1) as a sequence of computer implemented acts or program modules (i.e., software) running on a computing device (e.g., the computing device described in FIG. 17B), (2) as interconnected machine logic circuits or circuit modules (i.e., hardware) within the computing device and/or (3) a combination of software and hardware of the computing device. Thus, the logical operations discussed herein are not limited to any specific combination of hardware and software. The implementation is a matter of choice dependent on the performance and other requirements of the computing device. Accordingly, the logical operations described herein are referred to variously as operations, structural devices, acts, or modules. These operations, structural devices, acts and modules may be implemented in software, in firmware, in special purpose digital logic, and any combination thereof. It should also be appreciated that more or fewer operations may be performed than shown in the figures and described herein. These operations may also be performed in a different order than those described herein.

Figure 17A:
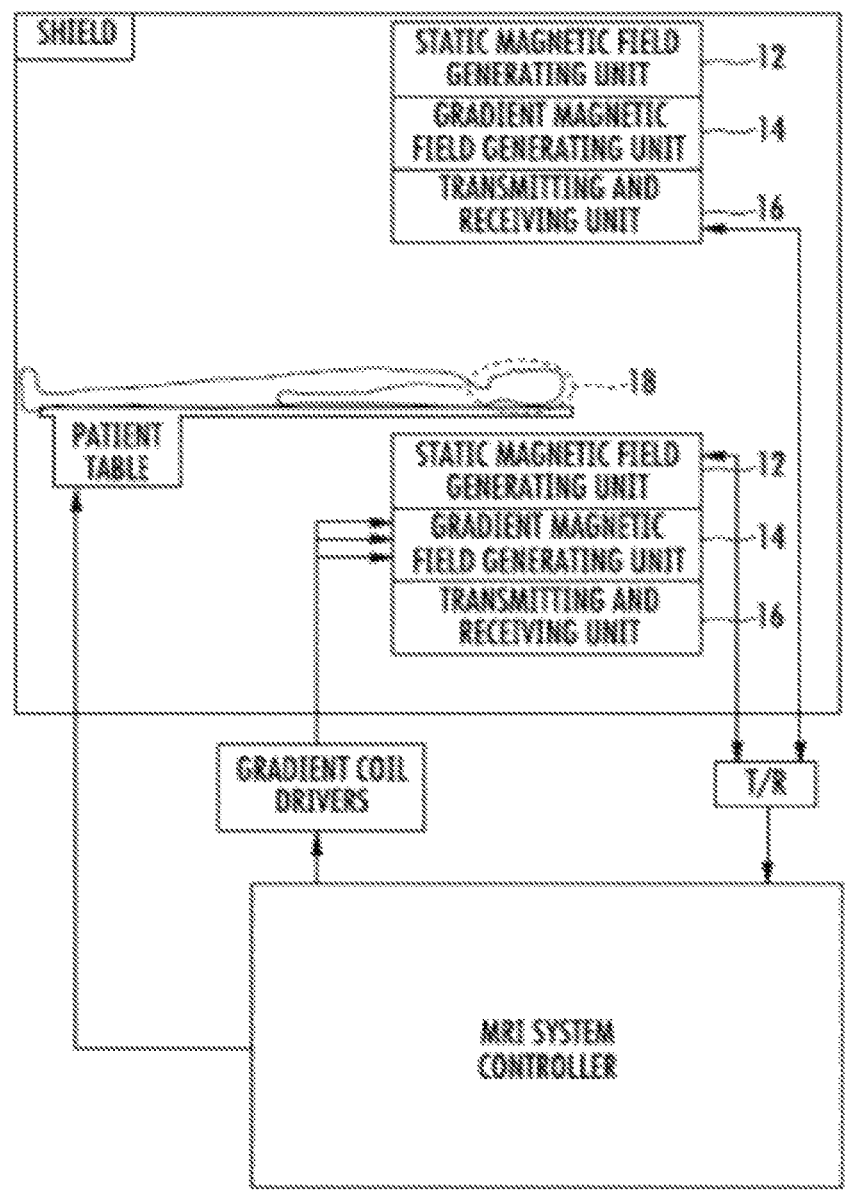
FIG. 17A is a diagram illustrating an example MRI system.
Figure 17B:
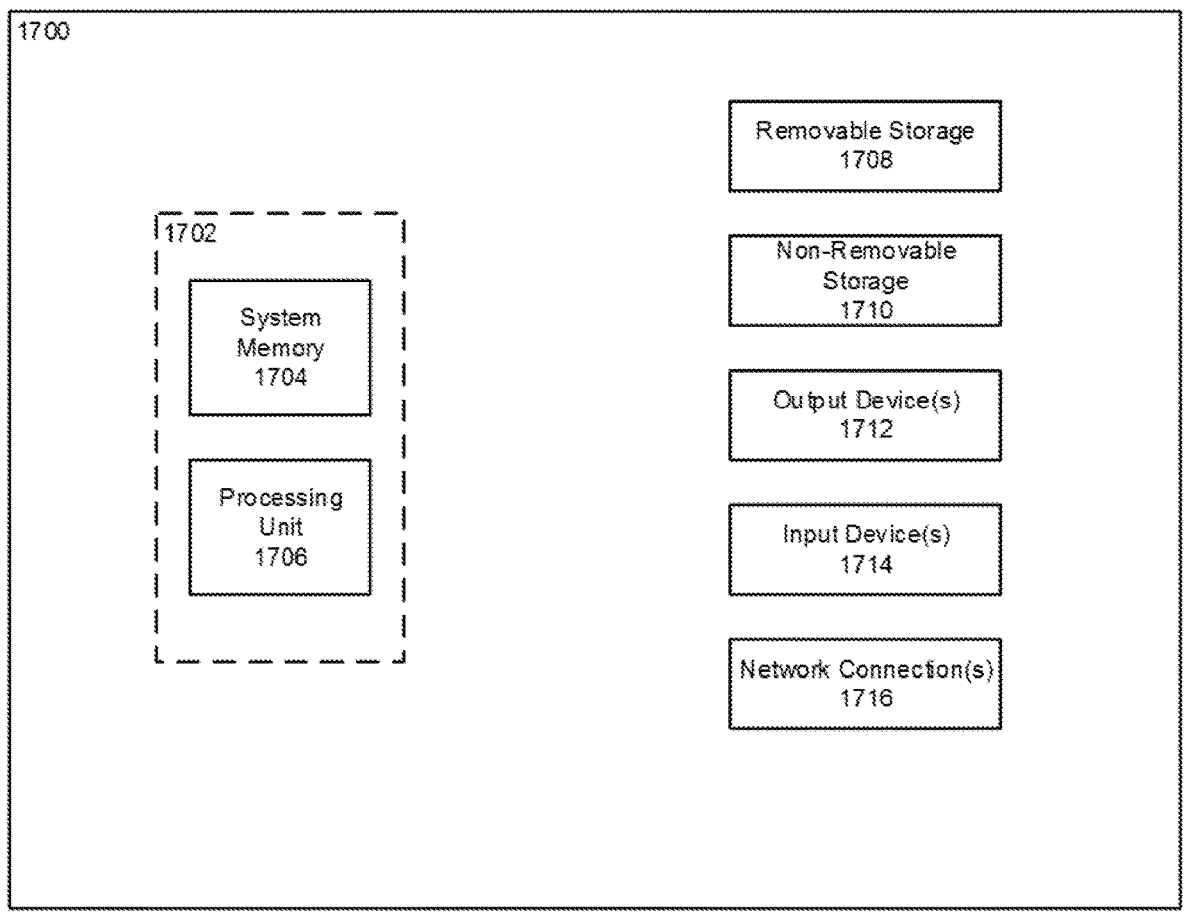
FIG. 17B is an example computing device.

Referring to FIG. 17B, an example computing device 1700 upon which embodiments of the invention may be implemented is illustrated. It should be understood that the example computing device 1700 is only one example of a suitable computing environment upon which embodiments of the invention may be implemented. Optionally, the computing device 1700 can be a well-known computing system including, but not limited to, personal computers, servers, handheld or laptop devices, multiprocessor systems, microprocessor-based systems, network personal computers (PCs), minicomputers, mainframe computers, embedded systems, and/or distributed computing environments including a plurality of any of the above systems or devices. Distributed computing environments enable remote computing devices, which are connected to a communication network or other data transmission medium, to perform various tasks. In the distributed computing environment, the program modules, applications, and other data may be stored on local and/or remote computer storage media.

In its most basic configuration, computing device 1700 typically includes at least one processing unit 1706 and system memory 1704. Depending on the exact configuration and type of computing device, system memory 1704 may be volatile (such as random access memory (RAM)), non-volatile (such as read-only memory (ROM), flash memory, etc.), or some combination of the two. This most basic configuration is illustrated in FIG. 17B by dashed line 1702. The processing unit 1706 may be a standard programmable processor that performs arithmetic and logic operations necessary for operation of the computing device 1700. The computing device 1700 may also include a bus or other communication mechanism for communicating information among various components of the computing device 1700.

Computing device 1700 may have additional features/functionality. For example, computing device 1700 may include additional storage such as removable storage 1708 and non-removable storage 1710 including, but not limited to, magnetic or optical disks or tapes. Computing device 1700 may also contain network connection(s) 1716 that allow the device to communicate with other devices. Computing device 1700 may also have input device(s) 1714 such as a keyboard, mouse, touch screen, etc. Output device(s) 1712 such as a display, speakers, printer, etc. may also be included. The additional devices may be connected to the bus in order to facilitate communication of data among the components of the computing device 1700. All these devices are well known in the art and need not be discussed at length here.

The processing unit 1706 may be configured to execute program code encoded in tangible, computer-readable media. Tangible, computer-readable media refers to any media that is capable of providing data that causes the computing device 1700 (i.e., a machine) to operate in a particular fashion. Various computer-readable media may be utilized to provide instructions to the processing unit 1706 for execution. Example tangible, computer-readable media may include, but is not limited to, volatile media, non-volatile media, removable media and non-removable media implemented in any method or technology for storage of information such as computer readable instructions, data structures, program modules or other data. System memory 1704, removable storage 1708, and non-removable storage 1710 are all examples of tangible, computer storage media. Example tangible, computer-readable recording media include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices.

In an example implementation, the processing unit 1706 may execute program code stored in the system memory 1704. For example, the bus may carry data to the system memory 1704, from which the processing unit 1706 receives and executes instructions. The data received by the system memory 1704 may optionally be stored on the removable storage 1708 or the non-removable storage 1710 before or after execution by the processing unit 1706.

It should be understood that the various techniques described herein may be implemented in connection with hardware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations.

For example, a method for detecting lesion tissue using contrast agent MRI can be implemented using the MRI system and/or computing device described with regard to FIGS. 17A and 17B. The method can include simulating a plurality of relationships between an image quality metric and one or more imaging parameters. As discussed herein, relationships between the image quality metric and imaging parameters can be numerically simulated, for example, using Bloch Equations or other approximation (e.g., an analytic solution, an EPG algorithm, a pseudo-steady-state algorithm, a windowed ramp function). In addition, the method can include selecting a first set of imaging parameters to optimize an image quality metric of a first image that is acquired before administration of contrast agent; selecting a second set of imaging parameters to optimize a lesion enhancement metric or a detection sensitivity metric of a second image that is acquired after administration of contrast agent; and selecting an image acquisition time for the second image to maximize contrast agent concentration or the lesion enhancement metric or a detection sensitivity metric. As described herein, the image acquisition time can be selected, for example, as described with regard to FIGS. 8 and 9. The method can further include acquiring the first image before administration of contrast agent using the selected first set of imaging parameters; acquiring the second image after administration of contrast agent at the selected image acquisition time using the selected second set of imaging parameters; and generating a combined image from the first image and the second image.

In some implementations, the method can further include receiving one or more MRI scanner settings, and receiving one or more magnetic resonance ("MR") parameters for lesion tissue with and/or without contrast agent. The numerical simulation of the relationships between the image quality metric and the one or more imaging parameters can be performed using at least one of the one or more MRI scanner settings or the one or more MR parameters. In other words, the MRI scanner setting(s) and/or the MR parameter(s) can be input into the numerical simulation.

Alternatively or additionally, a method for detecting lesion tissue using contrast agent MRI can be implemented using the MRI system and/or computing device described with regard to FIGS. 17A and 17B. The method can include simulating a plurality of relationships between an image quality metric and one or more imaging parameters. As discussed herein, relationships between the image quality metric and imaging parameters can be numerically simulated, for example, using Bloch Equations or other approximation (e.g., an analytic solution, an EPG algorithm, a pseudo-steady-state algorithm, a windowed ramp function). In addition, the method can include selecting a set of imaging parameters to optimize a lesion enhancement metric or a detection sensitivity metric of an image that is acquired after administration of contrast agent; and selecting an image acquisition time for the image to maximize the lesion enhancement metric or a detection sensitivity metric. As described herein, the image acquisition time can be selected, for example, as described above with regard to FIGS. 8 and 9. The method can further include acquiring the image after administration of contrast agent at the selected image acquisition time using the selected set of imaging parameters.

In some implementations, the method can further include receiving one or more MRI scanner settings, and receiving one or more magnetic resonance ("MR") parameters for lesion tissue with contrast agent. The numerical simulation of the relationships between the image quality metric and the one or more imaging parameters can be performed using at least one of the one or more MRI scanner settings or the one or more MR parameters. In other words, the MRI scanner setting(s) and/or the MR parameter(s) can be input into the numerical simulation.

Alternatively or additionally, a method for suppressing leakage of contrast agent in an image can be implemented using the MRI system and/or computing device described with regard to FIGS. 17A and 17B. The method can include performing image processing to suppress leakage of the contrast agent into healthy tissue; or selecting a magnetic resonance imaging ("MRI") sequence to suppress leakage of the contrast agent into the healthy tissue. Example methods for suppressing leakage using image process are described herein, for example, with regard to FIG. 14. Example methods for suppressing leakage by selecting or modifying an MRI sequence are described herein, for example, with regard to FIG. 15. This disclosure contemplates that the method for suppressing leakage of contrast agent can be used with the methods for detecting lesion tissue using contrast agent magnetic resonance imaging ("MRI") described herein. In other words, the method for suppressing leakage of contrast agent can be used to suppress leakage of contrast agent in the image acquired after contrast agent administration.

Alternatively or additionally, a method for performing contrast agent MRI can be implemented using the MRI system and/or computing device described with regard to FIGS. 17A and 17B. The method can include receiving a time course of lesion enhancement or contrast agent concentration; receiving a magnetic resonance imaging ("MRI") sequence and one or more imaging parameters; selecting an image acquisition time for image acquisition after administration of contrast agent to match k-space sampling of the MRI sequence with the time course of lesion enhancement or contrast agent concentration; and acquiring a post-contrast image at the selected image acquisition time. As described herein, the image acquisition time can be selected, for example, as described above with regard to FIGS. 8 and 9.

Alternatively or additionally, a method for combining a pre-contrast image and a post-contrast image can be implemented using the MRI system and/or computing device described with regard to FIGS. 17A and 17B. The example method can include receiving a pre-contrast image and a post-contrast image; co-registering the post-contrast image into the pre-contrast image; extracting a region of interest from the registered post-contrast image; and combining the extracted region of interest into the pre-contrast image at a corresponding image location to form a combined image. Example methods of combining pre- and post-contrast images are described herein, for example, with respect to FIG. 12. This disclosure contemplates that the method for combining a pre-contrast image and a post-contrast image can be used with the methods of detecting lesion tissue using contrast agent magnetic resonance imaging ("MRI") described herein.

Alternatively or additionally, a method for determining an optimal contrast agent concentration for contrast agent MRI imaging can be implemented using the MRI system and/or computing device described with regard to FIGS. 17A and 17B. The method can include receiving a magnetic resonance imaging ("MRI") sequence; receiving a targeted image quality metric; simulating a plurality of relationships among the targeted image quality metric, one or more imaging parameters, and contrast agent concentration; selecting a set of imaging parameters and a contrast agent concentration to optimize a lesion enhancement metric or a detection sensitivity metric after administration of contrast agent; administrating a contrast agent with the selected contrast agent concentration; and acquiring a post-contrast image after administration of the contrast agent using the selected one or more imaging parameters. This disclosure contemplates that the user can select a desired MRI scanner and/or user-selectable MRI scanner parameter(s) and/or an MRI sequence. As discussed herein, relationships between the image quality metric and imaging parameters can be numerically simulated, for example, using Bloch Equations or other approximation (e.g., an analytic solution, an EPG algorithm, a pseudo-steady-state algorithm, a windowed ramp function).

REFERENCES

1. Fakhran S et al. Assessment of rates of acute adverse reactions to gadobenate dimeglumine: review of more than 130,000 administrations in 7.5 years. AJR Am J Roentgenol. 2015; 204:703-706
2. Aronen H J et al. (1998). The effect of paramagnetic contrast media on T1 relaxation times in brain tumors. Acta Radiol 39:474-481
3. van der Molen A J, Bellin M F. Extracellular gadolinium-based contrast media: differences in diagnostic efficacy. Eur J Radiol. 2008; 66(2):168-74.
4. Jeon J-Y et al. Effect of Imaging Time in the Magnetic Resonance Detection of Intracerebral Metastases Using Single Dose Gadobutrol. Korean Journal of Radiology. 2014; 15(1):145-50.
5. De Stasio G et al. Gadolinium in human glioblastoma cells for gadolinium neutron capture therapy. Cancer research. 2001; 61(10):4272-7.
6. Biswas J et al. Brain tumor enhancement in magnetic resonance imaging: comparison of signal-to-noise ratio (SNR) and contrast-to-noise ratio (CNR) at 1.5 versus 3 tesla. Invest Radiol. 2005; 40(12):792-7.
7. Essig M. MR imaging of CNS tumors: are all contrast agents created the same? Neuroradiology. 2006; 48 Suppl 1:3-8.
8. Shah K B et al. Comparison of gadolinium-enhanced fat-saturated T1-weighted FLAIR and fast spin-echo MRI of the spine at 3 T for evaluation of extradural lesions. AJR Am J Roentgenol. 2011; 197(3):697-703.
9. Wang J, Lu Z L. Methods and apparatus for optimization of MRI protocol. (U.S. 2015/0071514 A1).
10. Wang J, He L, Lu Z L. Optimization of Magnetization-prepared Rapid Gradient-echo (MP-RAGE) Sequence at 3.0 T. PLOS ONE. 2014; 9: e96899.
11. Wang J, Parikh N A, Lu Z L, He L. Methods and apparatus for optimization of MRI protocol (U.S. Prov. App. No. 62/131,737).
12. He L, Wang J, Lu Z L, and Parikh N A. Optimization of Neonatal Magnetization-Prepared Rapid Gradient Echo (MP-RAGE) Sequence with Shorter Acquisition Train Length. (submitted to Journal)
13. Kammer N et al. Comparison of contrast-enhanced modified T1-weighted 3D TSE black-blood and 3D MP-RAGE sequences for the detection of cerebral metastases and brain tumours. European radiology. 2015:1-8.
14. Weigel M, Helms G, Hennig J. Investigation and modeling of magnetization transfer effects in two-dimensional multislice turbo spin echo sequences with low constant or variable flip angles at 3 T. Magnetic resonance in medicine. 2010; 63(1):230-4.
15. Lukzen N et al. The generating functions formalism for the analysis of spin response to the periodic trains of RF pulses. Echo sequences with arbitrary refocusing angles and resonance offsets. Journal of Magnetic Resonance. 2009; 196(2):164-9.
16. Hennig J, Weigel M, Scheffler K. Calculation of flip angles for echo trains with predefined amplitudes with the extended phase graph (EPG)-algorithm: principles and applications to hyperecho and TRAPS sequences. Magnetic resonance in medicine. 2004; 51(1):68-80.
17. Alsop D C. The sensitivity of low flip angle RARE imaging. Magnetic resonance in medicine. 1997; 37(2): 176-84.
18. Hennig J. Echoes—how to generate, recognize, use or avoid them in MR-imaging sequences. Part II: Echoes in imaging sequences. Concepts in Magnetic Resonance. 1991; 3(4):179-92.
19. Busse R F. Reduced RF power without blurring: correcting for modulation of refocusing flip angle in FSE sequences. Magnetic resonance in medicine. 2004; 51(5): 1031-7.
20. Lee V S et al. Single-dose breath-hold gadolinium-enhanced three-dimensional MR angiography of the renal arteries. Radiology 1999; 211: 69-77.
21. Maravilla K R et al. Contrast Enhancement of Central Nervous System Lesions: Multicenter Intraindividual Crossover Comparative Study of Two MR Contrast Agents 1. Rdiology. 2006; 240(2):389-400.
22. Schmidt M A, Morgan R. Renal Contrast-enhanced MR Angiography: Timing Errors and Accurate Depiction of Renal Artery Origins1. Radiology. 2008; 249(1):178-186.
23. Weng J C et al. Pulse sequence and timing of contrast-enhanced MRI for assessing blood-brain barrier disruption after transcranial focused ultrasound in the presence of hemorrhage. Journal of Magnetic Resonance Imaging. 2010; 31(6):1323-30.
24. Maki J H et al. Patient-specific timing for bolus-chase peripheral MR angiography. Journal of Magnetic Resonance Imaging. 2016; 43(1):249-60.
25. Gross P et al. System Scan Timing by Ultrasound Contrast Agent Study. US20130274589 A1
26. Liu K, Margosian P M. Diagnostic imaging systems and methods employing temporally resolved intensity tracing. U.S. Pat. No. 6,505,064 B1
27. James A P, Dasarathy B V. Medical image fusion: A survey of the state of the art. Information Fusion. 2014; 19:4-19.
28. Sperling D S. System and method for using medical image fusion. U.S. Pat. No. 8,472,684, 2013.
29. Bond S, Kadir T. Methods and apparatus for registration of medical images. U.S. Pat. No. 8,818,057 B2
30. Oliveira F P, Tavares J M R. Medical image registration: a review. Computer methods in biomechanics and biomedical engineering. 2014; 17(2):73-93.
31. Pham D L, Xu C, Prince J L. Current methods in medical image segmentation 1. Annual review of biomedical engineering. 2000; 2(1):315-37.
32. Setarehdan S K, Singh S. Advanced algorithmic approaches to medical image segmentation: state-of-the-art applications in cardiology, neurology, mammography and pathology: Springer Science & Business Media; 2012.
33. Sussman, M. S., et al., Optimizing contrast agent concentration and spoiled gradient echo pulse sequence parameters for catheter visualization in MR-guided interventional procedures: an analytic solution. Magn Reson Med, 2013. 70(2): p. 333-40.
34. Grobner T. Gadolinium—a specific trigger for the development of nephrogenic fibrosing dermopathy and nephrogenic systemic fibrosis? Nephrol Dial Transplant 2006; 21:1104-1108.
35. Kanda T, Ishii K, Kawaguchi H, et al. High signal intensity in the dentate nucleus and globus pallidus on unenhanced T1-weighted MR images: relationship with increasing cumulative dose of a gadolinium-based contrast material. Radiology. 2014; 270: 834-841.
36. Errante Y, Cirimele V, Mallio C A, et al. Progressive increase of T1 signal intensity of the dentate nucleus on unenhanced magnetic resonance images is associated with cumulative doses of intravenously administered gadodiamide in patients with normal renal function, suggesting dechelation. Invest Radiol. 2014; 49: 685-690.
37. McDonald R J, McDonald J S, Kallmes D F, et al. Intracranial gadolinium deposition after contrast-enhanced MR imaging. Radiology. 2015; 275: 772-782.
38. Quattrocchi C C et al. Gadodiamide and dentate nucleus T1 hyperintensity in patients with meningioma evaluated by multiple follow-up contrast-enhanced magnetic resonance examinations with no systemic interval therapy. Invest Radiol. 2015; 50: 470-472.
39. Radbruch A et al. Gadolinium retention in the dentate nucleus and globus pallidus is dependent on the class of contrast agent. Radiology. 2015; 275: 783-791
40. Kanda T et al. High signal intensity in dentate nucleus on unenhanced T1-weighted MR images: association with linear versus macrocyclic gadolinium chelate administration. Radiology. 2015; 275: 803-809.
41. Adin M E et al. Hyperintense dentate nuclei on T1-weighted MRI: relation to repeat gadolinium administration. AJNR Am J Neuroradiol. 2015; 36: 1859-1865.
42. Radbruch A et al. Gadolinium retention in the dentate nucleus and globus pallidus is dependent on the class of contrast agent. Radiology 2015; 275:783-91.
43. Ramalho J et al. High signal intensity in globus pallidus and dentate nucleus on unenhanced T1-weighted MR images: evaluation of two linear gadolinium-based contrast agents.
Radiology 2015 Jun. 16: 150872
44. Robert P et al. T1-weighted hypersignal in the deep cerebellar nuclei after repeated administrations of gadolinium-based contrast agents in healthy rats: difference between linear and macrocyclic agents. Invest Radiol 2015 Jun. 22 [Epub ahead of print].
45. Kanda T et al. Gadolinium-based Contrast Agent Accumulates in the Brain Even in Subjects without Severe Renal Dysfunction: Evaluation of Autopsy Brain Specimens with Inductively Coupled Plasma Mass Spectroscopy. Radiology. (2015) Volume: 276, Issue: 1, pp. 228-232
46. Weinmann H-J, Brasch R C, Press W-R, Wesbey G E. Characteristics of gadolinium-DTPA complex: a potential NMR contrast agent. American Journal of Roentgenology. 1984; 142(3):619-24.
47. Schörner W et al. Time-dependent changes in image contrast in brain tumors after gadolinium-DTPA. American journal of neuroradiology. 1986; 7(6):1013-20.
48. Sze G et al. Multicenter study of gadodiamide injection as a contrast agent in MR imaging of the brain and spine. Radiology. 1991; 181(3):693-9.
49. Runge V M, Bronen R A, Davis K R. Efficacy of gadoteridol for magnetic resonance imaging of the brain and spine. Invest Radiol. 1992; 27 Suppl 1:S22-32.
50. Mugler J P, 3rd, Brookeman J R. Theoretical analysis of gadopentetate dimeglumine enhancement in T1-weighted imaging of the brain: comparison of two-dimensional spin-echo and three-dimensional gradient-echo sequences. J Magn Reson Imaging. 1993; 3(5):761-9.
51. Chappell P M et al. Comparison of lesion enhancement on spin-echo and gradient-echo images. AJNR Am J Neuroradiol. 1994; 15(1):37-44.
52. Yuh W et al. The effect of contrast dose, imaging time, and lesion size in the MR detection of intracerebral metastasis. American journal of neuroradiology. 1995; 16(2):373-80.
53. Elster A. How much contrast is enough? Eur Radiol. 1997; 7(5 S 276):280.
54. Su M Y, Mühler A, Lao X, Nalcioglu O. Tumor characterization with dynamic contrast-enhanced MRI using mr contrast agents of various molecular weights. Magnetic resonance in medicine. 1998; 39(2):259-69.
55. Knauth M, Aras N, Wirtz C R, Dörfler A, Engelhorn T, Sartor K. Surgically induced intracranial contrast enhancement: potential source of diagnostic error in intraoperative MR imaging. American journal of neuroradiology. 1999; 20(8):1547-53.
56. Steen R G et al. Effect of a gadodiamide contrast agent on the reliability of brain tissue T1 measurements. Magn Reson Imaging. 1999; 17(2):229-35.
57. Roberts T P, Chuang N, Roberts H C. Neuroimaging: do we really need new contrast agents for MRI? Eur J Radiol. 2000; 34(3):166-78.
58. Landis C S et al. Determination of the MRI contrast agent concentration time course in vivo following bolus injection: effect of equilibrium transcytolemmal water exchange. Magnetic resonance in medicine. 2000; 44(4): 563-74.
59. Padhani A R, Husband J E. Dynamic contrast-enhanced MRI studies in oncology with an emphasis on quantification, validation and human studies. Clinical radiology. 2001; 56(8):607-20.
60. Colosimo C et al. Detection of intracranial metastases: a multicenter, intrapatient comparison of gadobenate dimeglumine-enhanced MRI with routinely used contrast agents at equal dosage. Investigative radiology. 2001; 36(2):72-81.
61. Nobauer-Huhmann I M et al. Magnetic resonance imaging contrast enhancement of brain tumors at 3 tesla versus 1.5 tesla. Invest Radiol. 2002 37(3):114-9.
62. Yamada K et al. Effect of intravenous gadolinium-DTPA on diffusion-weighted images: evaluation of normal brain and infarcts. Stroke. 2002; 33(7):1799-802.
63. Weinmann H-J et al. Tissue-specific MR contrast agents. European journal of radiology. 2003; 46(1):33-44.
64. Trattnig S et al. MR contrast agent at high-field MRI (3 Tesla). Top Magn Reson Imaging. 2003; 14(5):365-75.
65. Louie A. Magnetic resonance imaging contrast agents in the study of development. Current topics in developmental biology. 2005; 70:35-56.
66. Masi J N et al. Optimization of gadodiamide concentration for MR arthrography at 3 T. American Journal of Roentgenology. 2005; 184(6):1754-61.
67. Krautmacher C et al. Brain tumors: full- and half-dose contrast-enhanced MR imaging at 3.0 T compared with 1.5 T—Initial Experience. Radiology. 2005; 237(3):1014-9.
68. Biswas J et al. Brain tumor enhancement in magnetic resonance imaging: comparison of signal-to-noise ratio (SNR) and contrast-to-noise ratio (CNR) at 1.5 versus 3 tesla. Invest Radiol. 2005; 40(12):792-7.
69. Colosimo C et al. Comparison of gadobenate dimeglumine (Gd-BOPTA) with gadopentetate dimeglumine (Gd-DTPA) for enhanced MR imaging of brain and spine tumours in children. Pediatr Radiol. 2005; 35(5):501-10.
70. Colosimo C, Cianfoni A, Di Lella G M, Gaudino S. Contrast-enhanced MR imaging of the spine: when, why and how? How to optimize contrast protocols in MR imaging of the spine. Neuroradiology. 2006; 48 Suppl 1:18-33.
71. Caravan P. Strategies for increasing the sensitivity of gadolinium based MRI contrast agents. Chemical Society Reviews. 2006; 35(6):512-23.
72. Atri M. New technologies and directed agents for applications of cancer imaging. Journal of Clinical Oncology. 2006; 24(20):3299-308.
73. Trattnig S, Pinker K, Ba-Ssalamah A, Nobauer-Huhmann I M. The optimal use of contrast agents at high field MRI. Eur Radiol. 2006; 16(6):1280-7.
74. Essig M et al. Contrast-enhanced magnetic resonance imaging of central nervous system tumors: agents, mechanisms, and applications. Topics in Magnetic Resonance Imaging. 2006; 17(2):89-106.
75. Bellin M-F. MR contrast agents, the old and the new. Eur J Radiol. 2006; 60(3):314-23.
76. Essig M. Protocol design for high relaxivity contrast agents in MR imaging of the CNS. Eur Radiol. 2006; 16 Suppl 7:M3-7.
77. Strijkers G J, Mulder W J, van Tilborg G A, Nicolay K. MRI contrast agents: current status and future perspectives. Anticancer Agents Med Chem. 2007; 7(3):291-305.
78. Sardanelli F et al. The value of chemical fat-saturation pulse added to $T_1$-weighted spin-echo sequence in evaluating gadolinium-enhancing brain lesions in multiple sclerosis. Radiol Med. 2007; 112(8):1244-51.
79. Lin S P, Brown J J. MR contrast agents: physical and pharmacologic basics. Journal of Magnetic Resonance Imaging. 2007; 25(5):884-99.
80. Pedersen M. Safety update on the possible causal relationship between gadolinium-containing MRI agents and nephrogenic systemic fibrosis. J Magn Reson Imaging. 2007; 25(5):881-3.
81. Yi C A et al. Non-Small Cell Lung Cancer Staging: Efficacy Comparison of Integrated PET/CT versus 3.0-T Whole-Body MR Imaging. Radiology. 2008; 248(2):632-42.
82. Martin D R. Nephrogenic system fibrosis: a radiologist's practical perspective. Eur J Radiol. 2008; 66(2):220-4.
83. Shellock F G, Spinazzi A. MRI safety update 2008: part 1, MRI contrast agents and nephrogenic systemic fibrosis. AJR Am J Roentgenol. 2008; 191(4):1129-39.
84. Bellin M-F, Van Der Molen A J. Extracellular gadolinium-based contrast media: An overview. Eur J Radiol. 2008; 66(2):160-7.
85. Prastawa M, Bullitt E, Gerig G. Simulation of brain tumors in MR images for evaluation of segmentation efficacy. Medical image analysis. 2009; 13(2):297-311.
86. Warmuth-Metz M, Bison B, Leykamm S. Neuroradiologic review in pediatric brain tumor studies. Clinical Neuroradiology. 2009; 19(4):263-73.
87. Giesel F L, Mehndiratta A, Essig M. High-relaxivity contrast-enhanced magnetic resonance neuroimaging: a review. Eur Radiol. 2010; 20(10):2461-74.
88. Natalin R A et al. Contemporary applications and limitations of magnetic resonance imaging contrast materials. J Urol. 2010; 183(1):27-33.
89. Hamilton B E et al. Comparative analysis of ferumoxytol and gadoteridol enhancement using T1- and T2-weighted MRI in neuroimaging. AJR Am J Roentgenol. 2011; 197(4):981-8.

90. Bogdanov A, Jr., Mazzanti M L. Molecular magnetic resonance contrast agents for the detection of cancer: past and present. Semin Oncol. 2011; 38(1):42-54.
91. Thomsen H S. Contrast media safety—an update. Eur J Radiol. 2011; 80(1):77-82.
92. Vargas H A, Wassberg C, Akin O, Hricak H. MR imaging of treated prostate cancer. Radiology. 2012; 262(1):26-42.
93. Lim H et al. MR diagnosis of facial neuritis: diagnostic performance of contrast-enhanced 3D-FLAIR technique compared with contrast-enhanced 3D-T1-fast-field echo with fat suppression. American journal of neuroradiology. 2012; 33(4):779-83.
94. Essig M et al. MR imaging of neoplastic central nervous system lesions: review and recommendations for current practice. American journal of neuroradiology. 2012; 33(5):803-17.
95. Essig M, Dinkel J, Gutierrez J E. Use of Contrast Media in Neuroimaging. Magnetic resonance imaging clinics of North America. 2012; 20(4):633-48.
96. Gutierrez J E, Koenig S, Breuer J. Overview on the efficacy and safety of gadobutrol: an MRI contrast agent for the CNS, body and vessels. Imaging in Medicine. 2012; 4(1):25-40.
97. Hao D, Ai T, Goerner F, Hu X, Runge V M, Tweedle M. MRI contrast agents: basic chemistry and safety. J Magn Reson Imaging. 2012; 36(5):1060-71.
98. Kanal E. Gadolinium-based magnetic resonance contrast agents for neuroradiology: an overview. Magn Reson Imaging Clin N Am. 2012; 20(4):625-31.
99. Kim B-s, Gutierrez J E. Contrast-Enhanced MR Imaging in Neuroimaging. Magn Reson Imaging Clin N Am. 2012; 20(4):649-85.
100. Ferré J-C, Shiroishi M S, Law M. Advanced Techniques Using Contrast Media in Neuroimaging. Magn Reson Imaging Clin N Am. 2012; 20(4):699-713.
101. Abernethy L, Avula S, Hughes G, Wright E, Mallucci C. Intra-operative 3-T MRI for paediatric brain tumours: challenges and perspectives. Pediatric radiology. 2012; 42(2):147-57.
102. Sourbron S P, Buckley D L. Classic models for dynamic contrast-enhanced MRI. NMR Biomed. 2013; 26(8):1004-27.
103. Obermeier B, Daneman R, Ransohoff R M. Development, maintenance and disruption of the blood-brain barrier. Nature medicine. 2013; 19(12):1584-96.
104. Shokrollahi H. Contrast agents for MRI. Mater Sci Eng C Mater Biol Appl. 2013; 33(8):4485-97.
105. Anzalone N et al. Optimizing contrast-enhanced magnetic resonance imaging characterization of brain metastases: relevance to stereotactic radiosurgery. Neurosurgery. 2013; 72(5):691-701.
106. Runge V M. Current technological advances in magnetic resonance with critical impact for clinical diagnosis and therapy. Investigative radiology. 2013; 48(12):869-77.
107. Guglielmo F F, Mitchell D G, Roth C G, Deshmukh S. Hepatic MR Imaging Techniques, Optimization, and Artifacts. Magn Reson Imaging Clin N Am. 2014; 22(3):263-82.
108. Hendrick R E. High-quality breast MRI. Radiol Clin North Am. 2014; 52(3):547-62.
109. Gruber S et al. Dynamic contrast-enhanced magnetic resonance imaging of breast tumors at 3 and 7 T: a comparison. Invest Radiol. 2014; 49(5):354-62.
110. Warntjes J B, Tisell A, Landtblom A M, Lundberg P. Effects of gadolinium contrast agent administration on automatic brain tissue classification of patients with multiple sclerosis. AJNR Am J Neuroradiol. 2014; 35(7):1330-6.
111. Castillo M. History and evolution of brain tumor imaging: insights through radiology. Radiology. 2014; 273(2 Suppl):S111-25.
112. Guglielmo F F, Mitchell D G, Gupta S. Gadolinium contrast agent selection and optimal use for body MR imaging. Radiol Clin North Am. 2014; 52(4):637-56.
113. Ledger A E, Borri M, Pope R J, Scurr E D, Wallace T, Richardson C, et al. Investigating the influence of flip angle and k-space sampling on dynamic contrast-enhanced MRI breast examinations. Acad Radiol. 2014; 21(11):1394-401.
114. Mitsumori L M, Bhargava P, Essig M, Maki J H. Magnetic resonance imaging using gadolinium-based contrast agents. Top Magn Reson Imaging. 2014; 23(1):51-69.
115. Zakaria R et al. The role of magnetic resonance imaging in the management of brain metastases: diagnosis to prognosis. Cancer Imaging. 2014; 14(1):8.
116. Lavdas E et al. Evaluation of fat saturation and contrast enhancement on T1-weighted FLAIR sequence of the spine at 3.0 T. Clin Imaging. 2014; 38(4):428-33.
117. Lescher S et al. Time window for postoperative reactive enhancement after resection of brain tumors: less than 72 hours. Neurosurgical focus. 2014; 37(6):E3.
118. Gutierrez J E et al. Safety and Efficacy of Gadobutrol for Contrast-enhanced Magnetic Resonance Imaging of the Central Nervous System: Results from a Multicenter, Double-blind, Randomized, Comparator Study. Magnetic resonance insights. 2015; 8:1.
119. Majigsuren M et al. Comparison of Brain Tumor Contrast-enhancement on T-CUBE and 3D-SPGR Images. Magn Reson Med Sci. 2015.
120. Noebauer-Huhmann I M et al. Brain tumours at 7T MRI compared to 3T—contrast effect after half and full standard contrast agent dose: initial results. Eur Radiol. 2015; 25(1):106-12.
121. Grosu A-L, Oehlke O, Nieder C. Brain Tumors. Target Volume Definition in Radiation Oncology: Springer; 2015. p. 1-21.
122. Lohrke, Jessica, et al. "25 Years of Contrast-Enhanced MRI: Developments, Current Challenges and Future Perspectives." Advances in therapy 33.1 (2016): 1-28.
123. Knopp M et al. Colon contrast enhanced imaging. U.S. Pat. No. 6,505,064 B1 (2003).
124. Armitage P A, Behrenbruch C P, Brady J M. Dynamic contrast enhanced magnetic resonance imaging. WO2003007010 A1 (2003).
125. Bjornerud A, Johansson L. Method of magnetic resonance imaging. US20030125617 A1 (2003).
126. Brady J, Armitage P, Behrenbruch C. Dynamic contrast enhanced magnetic resonance imaging. US20040242994 A1 (2004).
127. Axelsson O et al. Multimeric magnetic resonance contrast agents US 2009/0238768 A1 (2006).
128. Thaning M, Zandt R I T. Mr imaging method for the discrimination between healthy and tumour tissue. WO2006114738 A2 (2006).
129. Willard N P et al. Mri0 involving contrast agent with time modulated contrast enhancement. WO2006114765 A2 (2006).
130. Degani H, Stein D. Mri Contrast Agents for Diagnosis and Prognosis of Tumors. US 2008/0305049 A1 (2006).

131. Iwadate Y, Nozaki A, Tsukamoto T, Kabasawa H. Breath holding mr imaging method, mri apparatus, and tomographic imaging apparatus. US20070073141 A1 (2006).
132. Hoffmann R. Contrast agents for detecting prostate cancer. US 2010/0215581 A1 (2007).
133. Ewing J R, Bagher-Ebadian H. Mri estimation of contrast agent concentration using a neural network approach. US20100198054 A1 (2008).
134. Willard N P et al. Responsive Mri Contrast Agents. US20080193384 A1 (2008)
135. Warmuth C, Reinhardt M, Weinmann H J. Magnetic resonance method for recording images of bone with positive contrast. WO2008138822 A1 (2008).
136. Willard N P et al. Mri Involving Contrast Agent With Time Modulated Contrast Enhancement. US20080200799 A1 (2008).
137. Fossheim S L et al. Use of particulate contrast agents in diagnostic imaging for studying physiological parameters. US20090191131 A1 (2009).
138. Schmainda K M et al. MRI method for measuring tumor hemodynamic parameters in the presence of contrast agent extravasation. U.S. Pat. No. 7,567,832 B2 (2009).
139. Colborn R E, Bonitatibus J P J, Tones A S, Marino M E, Butts M D, Kulkarni A, et al. Nanoparticle contrast agents for diagnostic imaging. WO2010125088 A2 (2010).
140. Cahill N D et al. Abnormality detection in medical images. U.S. Pat. No. 7,738,683 B2 (2010).
141. Wadsworth H J et al. Chelators, paramagnetic chelates thereof and their use as contrast agents in magnetic resonance imaging (mri). US20110200536 A1 (2011).
142. Helm P A, Shi S. Method and Apparatus for Reconstructing Image Projections. US 2012/0099768 A1 (2012).
143. Kowalevicz A. Methods and apparatus for image fusion. US 2014/0169658 A1 (2012).
144. Vija A H, Rempel T D. Systems and methods for localized image registration and fusion. U.S. Pat. No. 8,090,429 B2 (2012).
145. Sikma E A S et al. Contrast agents. U.S. Pat. No. 8,337,813 B2 (2012).
146. Dahnke H, Schaeffter T. Multiple contrast agent injection for imaging. U.S. Pat. No. 8,175,678 B2 (2012).
147. Gross P et al. System Scan Timing by Ultrasound Contrast Agent Study. US2013/0279785 A1 (2012).
148. Kim S M et al. Method of processing medical image of blood vessel using image fusion method. U.S. Pat. No. 8,428,323 B2 (2013).
149. Lamerichs R M J N, Wegh R T, Pikkemaat J A. Elimination of contrast agent concentration dependency in MRI. U.S. Pat. No. 8,463,358 B2 (2013).
150. Balbi L et al. Biomedical image reconstruction method. US2013/0310678A1 (2013).
151. Periaswamy S. Systems and methods for generating fused medical images from multi-parametric, magnetic resonance image data. U.S. Pat. No. 8,472,684 B1 (2013).
152. Caravan P et al. Manganese-based magnetic resonance contrast agents. WO2014107722 A1 (2014).
153. Dale B. Methods and systems for determining the concentration of a contrast agent. US20140064589 A1 (2014).
154. Fan H et al. Multivalent constructs for therapeutic and diagnostic applications. U.S. Pat. No. 9,056,138 B2 (2015).
155. Riederer S J, Campeau N G, Haider C R. System and method for combined time-resolved magnetic resonance angiography and perfusion imaging. U.S. Pat. No. 9,002,430 B2 (2015).
156. Wawro M. Method and apparatus for determining a contrast agent enhancement. US Patent 2015/0247909. (2015).
157. Wenzel F, Thiele F O, Young S. Interactive optimization of scan databases for statistical testing. US2015/0036948 A1 (2015).

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed:

1. A method for detecting lesion tissue using contrast agent magnetic resonance imaging ("MRI"), comprising:
   simulating a plurality of relationships between an image quality metric and one or more imaging parameters;
   selecting a first set of imaging parameters to optimize the image quality metric of a first image that is acquired before administration of contrast agent;
   selecting a second set of imaging parameters to optimize a lesion enhancement metric or a detection sensitivity metric of a second image that is acquired after administration of contrast agent;
   selecting an image acquisition time for the second image to maximize the lesion enhancement metric or the detection sensitivity metric;
   acquiring the first image before administration of contrast agent using the selected first set of imaging parameters;
   acquiring the second image after administration of contrast agent at the selected image acquisition time using the selected second set of imaging parameters, wherein the first set of imaging parameters are different than the second set of imaging parameters; and
   generating a combined image from the first image and the second image.

2. The method of claim 1, wherein the first image and the second image are acquired using the same MRI sequence, or wherein the first image and the second image are acquired using different MRI sequences.

3. The method of claim 2, wherein the MRI sequence comprises at least one of gradient echo, spin echo, gradient echo train, or spin echo train acquisition with or without magnetization preparation and/or specific tissue suppression.

4. The method of claim 2, wherein the MRI sequence comprises at least one of 2-dimensional acquisition or 3-dimensional acquisition.

5. The method of claim 1, wherein the one or more imaging parameters comprise at least one of a repetition time ("TR"), echo time ("TE"), variable flip angle, variable refocusing angle, magnetization preparation pulses, fat saturation pulses, inversion times, radiofrequency ("RF") bandwidth, echo train length, echo space time, slab number, or readout radiofrequency ("RF") number.

6. The method of claim 1, further comprising estimating the image quality metric from at least one image.

7. The method of claim 1, further comprising:
   receiving one or more MRI scanner settings; and
   receiving one or more magnetic resonance ("MR") parameters for lesion tissue with and/or without contrast agent, wherein simulating the plurality of relationships between the image quality metric and the one or more imaging parameters is based on at least one of the one or more MRI scanner settings or the one or more MR parameters.

8. The method of claim 7, wherein the one or more MRI scanner settings comprise at least one of MRI sequence, static field strength, spatial-resolution, radiofrequency ("RF") bandwidth, echo space time, parallel acquisition, saturation, or magnetization preparation.

9. The method of claim 1, wherein the image quality metric comprises at least one of lesion location, lesion border delineation, lesion morphology, contrast or contrast efficiency between lesion tissue and healthy tissue, contrast-to-noise ratio ("CNR") or CNR efficiency between lesion tissue and healthy tissue, signal intensity, signal intensity efficiency, or image artifact.

10. The method of claim 1, wherein optimizing the image quality metric comprises at least one of:
optimizing a contrast metric between lesion tissue and healthy tissue;
minimizing image artifact; or
optimizing a signal intensity of lesion tissue.

11. The method of claim 1, wherein the lesion enhancement metric comprises a change in signal intensity of lesion tissue between the first image and the second image.

12. The method of claim 1, wherein optimizing the lesion enhancement metric comprises maximizing the lesion enhancement metric.

13. The method of claim 1, further comprising optimizing a k-space strategy for acquiring the first image or the second image.

14. The method of claim 1, further comprising optimizing an acquisition train length of an MRI sequence for acquiring the first image or the second image.

15. The method of claim 1, further comprising using the combined image for medical diagnostics or medical treatment.

16. The method of claim 15, wherein the combined image is used for medical treatment, the method further comprising providing a visualization and localization of healthy tissue adjacent to lesion tissue to avoid damaging the healthy tissue during the medical treatment.

17. The method of claim 1, wherein the image acquisition time comprises a start time of acquisition and an acquisition duration time.

18. The method of claim 1, wherein the lesion tissue comprises at least one of tumor, multiple sclerosis, inflammation disease, infection disease, stroke, traumatic nerve injury, stroke, vascular disease, or musculoskeletal disease.

19. The method of claim 1, wherein the contrast agent comprises at least one physiologically acceptable paramagnetic substance, superparamagnetic substance, or ferromagnetic substance, or wherein the contrast agent comprises at least one of a magnetic small-molecule-based compound, a magnetic large-molecule-based compound, or a magnetic nanoparticle-based compound.

20. The method of claim 1, wherein the combined image is generated by:
detecting a lesion in the second image,
registering the first image and the second image,
extracting the detected lesion from the second image, and
overlaying the detected lesion onto the first image to form the combined image.

* * * * *